(12) United States Patent
Stephan

(10) Patent No.: US 11,566,061 B2
(45) Date of Patent: Jan. 31, 2023

(54) SYSTEMS AND METHODS TO IMPROVE VACCINE EFFICACY

(71) Applicant: Fred Hutchinson Cancer Center, Seattle, WA (US)

(72) Inventor: Matthias Stephan, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 583 days.

(21) Appl. No.: 16/474,503

(22) PCT Filed: Jan. 5, 2018

(86) PCT No.: PCT/US2018/012507
§ 371 (c)(1),
(2) Date: Jun. 27, 2019

(87) PCT Pub. No.: WO2018/129270
PCT Pub. Date: Jul. 12, 2018

(65) Prior Publication Data
US 2020/0123219 A1 Apr. 23, 2020

Related U.S. Application Data

(60) Provisional application No. 62/442,903, filed on Jan. 5, 2017.

(51) Int. Cl.
| *A61K 39/39* | (2006.01) |
| *A61P 35/00* | (2006.01) |
| *C07K 14/725* | (2006.01) |
| *A61K 47/69* | (2017.01) |
| *A61K 47/68* | (2017.01) |
| *A61K 39/00* | (2006.01) |
| *A61K 9/00* | (2006.01) |

(52) U.S. Cl.
CPC ........ *C07K 14/7051* (2013.01); *A61K 9/0019* (2013.01); *A61K 39/001168* (2018.08); *A61K 39/39* (2013.01); *A61K 47/6849* (2017.08); *A61K 47/6931* (2017.08); *A61P 35/00* (2018.01); *A61K 2039/555* (2013.01); *A61K 2039/852* (2018.08)

(58) Field of Classification Search
None
See application file for complete search history.

(56) References Cited

U.S. PATENT DOCUMENTS

| 4,078,052 A | 3/1978 | Papahadjopoulos |
| 4,224,179 A | 9/1980 | Schneider |
| 4,229,360 A | 10/1980 | Schneider et al. |
| 4,235,871 A | 11/1980 | Papahadjopoulos et al. |
| 4,241,046 A | 12/1980 | Papahadjopoulos et al. |
| 4,501,728 A | 2/1985 | Geho et al. |
| 4,737,323 A | 4/1988 | Martin et al. |
| 4,837,028 A | 6/1989 | Allen |
| 5,270,163 A | 12/1993 | Gold et al. |
| 5,756,122 A | 5/1998 | Thierry et al. |
| 6,491,916 B1 | 12/2002 | Bluestone et al. |
| 7,332,586 B2 | 2/2008 | Franzen et al. |
| 7,498,177 B2 | 3/2009 | De La Fuente et al. |
| 7,531,624 B2 | 5/2009 | Banes et al. |
| 7,550,650 B2 | 6/2009 | Rapp et al. |
| 8,008,438 B2 | 8/2011 | Boulter et al. |
| 8,440,431 B2 | 5/2013 | Voytas et al. |
| 8,663,599 B1 | 3/2014 | Sung et al. |
| 10,174,095 B2 | 1/2019 | Brogdon et al. |
| 10,188,749 B2 | 1/2019 | Stephan et al. |
| 10,189,906 B2 | 1/2019 | Lipp et al. |
| 2002/0045235 A1 | 4/2002 | Karin et al. |
| 2003/0072794 A1 | 4/2003 | Boulikas |
| 2003/0166601 A1 | 9/2003 | Woodle et al. |
| 2004/0043401 A1 | 3/2004 | Sadelain et al. |
| 2004/0067587 A1 | 4/2004 | Trubetskoy et al. |
| 2004/0071654 A1 | 4/2004 | Anderson et al. |
| 2005/0142114 A1 | 6/2005 | Gieseler et al. |
| 2007/0281897 A1 | 12/2007 | Karaolis |
| 2008/0171061 A1 | 7/2008 | Nixon et al. |
| 2009/0104229 A1 | 4/2009 | Voss |
| 2009/0136917 A1 | 5/2009 | Szalay et al. |
| 2011/0189209 A1 | 8/2011 | Neville et al. |
| 2011/0229556 A1 | 9/2011 | Irvine et al. |
| 2012/0156135 A1 | 6/2012 | Farokhzad et al. |
| 2012/0192298 A1 | 7/2012 | Weinstein et al. |
| 2012/0207783 A1 | 8/2012 | Donnelly et al. |

(Continued)

FOREIGN PATENT DOCUMENTS

| CN | 102851304 A | 1/2013 |
| WO | WO9601126 | 1/1996 |
| WO | WO2000702880 A2 | 12/2000 |
| WO | WO2008109806 A2 | 9/2008 |
| WO | WO2009146867 A1 | 12/2009 |
| WO | WO2011005799 A2 | 1/2011 |
| WO | WO2012079000 A1 | 6/2012 |
| WO | WO2012093258 A2 | 7/2012 |
| WO | WO2014153114 A1 | 9/2014 |
| WO | WO2014191527 A1 | 12/2014 |

(Continued)

OTHER PUBLICATIONS

Stauss et al. WT1-specific T cell receptor gene therapy: Improving TCR function in transduced T cells. Blood Cells, Molecules, and Diseases 40 (2008) 113-116.*
Office Action dated Nov. 9, 2021 for Chinese Application No. 201780023532.9, 6 pages.
Office Action dated Nov. 1, 2021 for Israeli Application No. 262361, 12 pages.
Office Action dated Oct. 15, 2021 in Korean Application No. 10-2018-7032542, 3 pages.

(Continued)

*Primary Examiner* — Nianxiang Zou
(74) *Attorney, Agent, or Firm* — C. Rachal Winger; Lee & Hayes PC

(57) ABSTRACT

Systems and methods to increase the efficacy of vaccines that require or are rendered more effective with T cell mediated immunity are described. The systems and methods utilize polynucleotides that genetically modify T cells to express a T cell receptor specific for an administered vaccine antigen.

28 Claims, 9 Drawing Sheets

Specification includes a Sequence Listing.

(56) References Cited

U.S. PATENT DOCUMENTS

| | | |
|---|---|---|
| 2013/0195881 A1 | 8/2013 | Singh et al. |
| 2014/0227186 A1 | 8/2014 | Rademacher et al. |
| 2014/0309177 A1 | 10/2014 | Perez-Pinera et al. |
| 2015/0110858 A1 | 4/2015 | DeRosa et al. |
| 2015/0246959 A1 | 9/2015 | Robbins et al. |
| 2015/0283178 A1 | 10/2015 | June et al. |
| 2016/0008399 A1 | 1/2016 | Stephan |
| 2016/0083449 A1 | 3/2016 | Schmitt et al. |
| 2016/0145348 A1 | 5/2016 | Stephan |
| 2016/0175251 A1 | 6/2016 | Ostroff et al. |
| 2016/0176969 A1 | 6/2016 | Bemett et al. |
| 2016/0250258 A1 | 9/2016 | Delaney et al. |
| 2016/0296471 A1 | 10/2016 | Bajpayee et al. |
| 2017/0224798 A1 | 8/2017 | Cooper et al. |
| 2017/0283830 A1 | 10/2017 | Saltzman et al. |
| 2017/0296676 A1 | 10/2017 | Stephan et al. |
| 2018/0030153 A1 | 2/2018 | Stephan |
| 2019/0111153 A1 | 4/2019 | Stephan et al. |
| 2019/0330373 A1 | 10/2019 | Stephan |
| 2021/0046156 A1 | 2/2021 | Stephan |
| 2021/0128485 A1 | 5/2021 | Stephan |

FOREIGN PATENT DOCUMENTS

| | | |
|---|---|---|
| WO | WO2015042585 | 3/2015 |
| WO | WO2016145102 A1 | 9/2016 |
| WO | WO2016180778 | 11/2016 |
| WO | WO2017112944 A1 | 6/2017 |
| WO | WO2017181110 A1 | 10/2017 |
| WO | WO2017201346 A1 | 11/2017 |
| WO | WO2018102752 A1 | 6/2018 |
| WO | WO2019143948 A1 | 7/2019 |
| WO | WO2019213308 A1 | 11/2019 |

OTHER PUBLICATIONS

Office Action dated Sep. 21, 2021 for Mexican Application No. MX/a/2018/012556, 6 pages.

Office Action dated Sep. 20, 2021 for U.S. Appl. No. 16/222,942, 15 Pages.

Arimilli, et al., "Refolding and Reconstitution of Functionally Active Complexes of Human Leukocyte Antigen DR2 and Myelin Basic Protein Peptide from Recombinant Alpha and Beta Polypeptide Chains," Bio. Chem., vol. 270, No. 2, 1995, pp. 971-977.

Bodmer, et al., "Nomenclature for factors of the HLA system, 1994," Tissue Antigens, vol. 4, 1994, pp. 1-18.

Boulikas, et al., "Nuclear localization signals (NLS)," Crit. Rev. Eukaryot Gene Expr., vol. 3, No. 3, 1993, pp. 193-227.

Cardinanos and Bradley, "Generation of an inducible and optimized piggyBac transposon system," Nucleic Acids Res., vol. 35, No. 35, 2007, pp. 1-8.

Chaloin, et al., "Design of Carrier Peptide-Oligonucleotide Conjugates with Rapid Membrane Translocation and Nuclear Localization Properties," Biochem. Biophys. Res. Commun., vol. 243, No. 2, 1998, pp. 601-608.

Cline, "Perspectives for gene therapy: Inserting new genetic information into mammalian cells by physical techniques and viral vectors," Pharmacol. Ther., vol. 29, No. 1, 1985, pp. 69-92.

Cokol, et al., "Finding nuclear localization signals," EMBO Rep, vol. 1, No. 5, 2000, pp. 44-415.

Collas and Alestrom, "Nuclear localization signal of SV40 T antigen directs import of plasmid DNA into sea urchin male pronuclei in vitro," Mol. Reprod. Devel, vol. 45, 1996, pp. 431-438.

Collas and Alestrom, "Nuclear localization signals enhance germline transmission of a transgene in zebrafish," Transgenic Research, vol. 7, No. 4, 1998, pp. 303-309.

Collas, et al., "Nuclear localization signals: a driving force for nuclear transport of plasmid DNA in zebrafish," Biochem. Cell Biol., vol. 75, No. 5, 1997, pp. 633-640.

Collas, et al., "The nuclear localization sequence of the SV40 T antigen promotes transgene uptake and expression in zebrafish embryo nuclei," Transgenic Res., vol. 5, No. 6, 1996, pp. 451-458.

Cotten, et al., "Receptor-Mediated Transport of DNA into Eukaryotic Cells," Methods Enzymol., vol. 217, 1993, pp. 618-644.

Derossi, et al., "Cell Internalization of the Third Helix of the Antennapedia Homeodomain Is Receptor-independent," J. Biol. Chem., vol. 271, No. 30, 1996, pp. 18188-18193.

Dingwall, et al., "Nuclear targeting sequences—a consensus?" Trends Biochem. Sci., vol. 16, No. 12, 1991, pp. 471-481.

Duguid, et al., "A physicochemical approach for predicting the effectiveness of peptide-based gene delivery systems tor use in plasmid-based gene therapy," Biophys. J., vol. 74, No. 6, 1998, pp. 2802-2814.

Fremont, et al., "Structures of an MHC Class II Molecule with Covalently Bound Single Peptides," Science, vol. 272, No. 5264, 1996, pp. 1001-1004.

Geall, et al., "Nonviral delivery of self-amplifying RNA vaccines," PNAS, vol. 109, No. 36, 2012, pp. 14604-14609.

Heikkinen, et al., "Safety of MF59-adjuvanated A/H1N1 influenza vaccine in pregnancy: a comparative cohort study," Am. J. Obstet Gynecol., vol. 207, No. 3, 2012, pp. 187.e1-187.e8.

Hope, et al., "Generation of multilamellar and unilamellar phospholipid vesicles," Chem. Phys. Lip., vol. 40, No. 2-4, 1986, pp. 89-107.

Kobayashi, et al., "A new cloning and expression system yields and validates TCRs from blood lymphocytes of patients with cancer within 10 days," Nat. Med., vol. 19, No. 11, 2013, pp. 1542-1546.

Kozono, et al., "Production of soluble MHC class II proteins with covalently bound single peptides," Nature, vol. 369, No. 154, 1994, pp. 151-154.

Loeffler and Behr, "Gene transfer into primary and established mammalian cell lines with lipopolyamine-coated DNA," Methods Enzymol., vol. 217, 1993, pp. 599-618.

Martin, et al., "The Design of Cationic Lipids for Gene Delivery," Curr. Pharm. Des., vol. 11, No. 3, 2005, pp. 375-394.

Mi, et al., "Characterization of a class of cationic peptides able to facilitate efficient protein transduction in vitro and in vivo," Mol. Ther., vol. 2, No. 4, 2000, pp. 338-347.

Nag, et al., "Functionally Active Recombinant Alpha and Beta Chain-Peptide Complexes of Human Major Histocompatibility Class II Molecules ," J Biol Chem., vol. 271, No. 17, 1996, pp. 10413-10418.

Nag, et al., "Stimulation of T cells by antigenic peptide complexed with isolated chains of major histocompatibility complex class II molecules," PNAS, vol. 90, No. 4, 1993, pp. 1604-1608.

Narayanan, et al., "Mimicking cellular transport mechanism in stem cells through endosomal escape of new peptide-coated quantum dots," Sci. Rep., vol. 3, 2013, 6 pages.

ClinicalTrials.gov [Internet], Bethesda (MD): National Library of Medicine (US). Feb. 29, 2000—. Identifier NCT01567891, CT Antigen TCR-redirected T Cells for Ovarian Cancer; Mar. 16, 2012; [about 10 screens]. Available from: https://clinicaltrials.gov/ct2/show/NCT01567891.

ClinicalTrials.gov [Internet], Bethesda (MD): National Library of Medicine (US). Jul. 13, 2012—. Identifier NCT01640301, Laboratory-Treated T Cells in Treating Patients With High-Risk Relapsed Acute Myeloid Leukemia, Myelodysplastic Syndrome, or Chronic Myelogenous Leukemia Previously Treated With Donor Stem Cell Transplant [about 11 screens]. Available from: https://clinicaltrials.gov/ct2/show/NCT01640301.

ClinicalTrials.gov [Internet], Bethesda (MD): National Library of Medicine (US). May 3, 2017—Identifier NCT03139370, Safety and Efficacy of MAGE-A3/A6 T Cell Receptor Engineered T Cells (KITE-718) in HLA-DPB1*04:01 Positive Adults With Advanced Cancers; [about 9 screens]. Available from: https://clinicaltrials.gov/ct2/show/NCT03139370.

Nicolle, et al., "Specific tolerance to an acetylcholine receptor epitope induced in vitro in myasthenia gravis CD4+ lymphocytes by soluble major histocompatibility complex class II-peptide complexes," J. Clin. Invest., 1994, vol. 93, No. 4, pp. 1361-1369.

Invitation to Pay Additional Fees Dated Mar. 20, 2018 for International Application No. PCT/US2018/012507, 3 pages.

Search Report and Written Opinion dated May 25, 2018 for International Application No. PCT/US2018/012507, 27 pages.

(56) References Cited

OTHER PUBLICATIONS

Rhode, et al., "Single-chain MHC class II molecules induce T cell activation and apoptosis," J. Immunol., vol. 157, No. 11, 1996, pp. 4885-4891.
Robbins, et al., "Single and Dual Amino Acid Substitutions in TCR CDRs Can Enhance Antigen-Specific T Cell Functions," J. Immunol., vol. 180, No. 9, 2008, pp. 6116-6131.
Sharma, et al., "Antigen-specific therapy of experimental allergic encephalomyelitis by soluble class II major histocompatibility complex-peptide complexes," PNAS, vol. 88, 1991, pp. 11465-11469.
Sharma, et al., "Computational study of the activated O(H) state in the catalytic mechanism of cytochrome c oxidase," Proc. Natl. Acad. Sci. U.S.A., vol. 110, No. 42, 2013, pp. 16844-16849.
Spack, et al., "Preclinical and Pharmacological Studies of AG284, a Soluble HLA-DR2:Myelin Basic Protein Peptide Complex for the Treatment of Multiple Sclerosis," CNS Drug Rev., vol. 4, No. 225, 1998, pp. 1527-3458.
Stromnes, et al., "T cells engineered against a native antigen can surmount immunologic and physical barriers to treat pancreatic ductal adenocarcinoma," Cancer Cell, vol. 28, No. 5, 2015, pp. 638-652.
Szoka, "Comparative properties and methods of preparation of lipid vesicles (liposomes)," Ann. Rev. Biophys. Bioeng., vol. 9, 1980, pp. 467-508.
Zhong, et al., "Direct Cytoplasmic Delivery and Nuclear Targeting Delivery of HPMA-MT Conjugates in a Microtubules Dependent Fashion," Mol. Pharm., vol. 13, 2016, pp. 3069-3079.
Office Action dated Jul. 7, 2020 for Colombian Application No. NC2018/0012099, 9 pages.
Office Action dated May 29, 2020 for European Patent Application No. 17783314.2, 4 pages.
Yang and Huang, "Overcoming the inhibitory effect of serum on lipofection by increasing the charge ratio of cationic liposome to DNA," Gene Therapy, vol. 4, 1997, pp. 950-960.
Zhang, et al., "MicroRNA-31 negatively regulates peripherally derived regulatory T-cell generation by repressing retinoic acid-inducible protein 3," Nat. Commun., vol. 6, No. 7639, 2015, 12 pages.
Zhu, et al., "Systemic Gene Expression After Intravenous DNA Delivery into Adult Mice," Science, vol. 261, 1993, 4 pages.
Office Action dated Feb. 2, 2021 in Chilean Application No. 02905-2018, 15 pages.
Office Action dated Dec. 15, 2020 for European Application No. 17783314.2, 4 pages.
Extended European Search Report dated Dec. 2, 2020 for European Application No. 18735984.9, 9 pages.
Robbins, et al., "A Pilot Trial Using Lymphocytes Genetically Engineered with an NY-ES0-1-Reactive T-cell Receptor: Long-term Follow-up and Correlates with Response," Clinical Cancer Research, vol. 21, No. 5, 2015, 10 pages.
Office Action dated May 25, 2021 for Chinese Patent Application No. 201880005741.5, 7 pages.
Office Action dated May 31, 2021 for Eurasian Patent Application No. 201892326, 31 pages.
Harris, et al., "Tissue-specific gene delivery via nanoparticle coating," Biomaterials, vol. 31, 2010, pp. 998-1006.
Office Action dated Jun. 1, 2021 for Japanese Patent Application No. 2018-553912, 4 pages.
Kurosaki, et al., "gamma-Polyglutamic acid-coated vectors for effective and safe gene therapy," Journal of Controlled Release, vol. 14, 2009, pp. 404-410.
Shmueli, et al., "Electrostatic Surface Modifications to Improve Gene Delivery," Expert Opin. Drug Deliv., vol. 7, No. 4, 2010, pp. 535-550.
Trubetskoy, et al., "Recharging cationic DNA Complexes with highly charged polyanions for in vitro and in vivo gene delivery," Gene Therapy, vol. 10, (2003) 10, 2003, pp. 261-271.
Office Action dated May 8, 2021 for Chinese Patent Application No. 201980029594.X, 1 page.
Office Action dated Aug. 6, 2021 for European Patent Application No. 17783314.2, 3 pages.
Robbins, et al., "A Pilot Trial Using Lymphocytes Genetically Engineered with an NY-ES0-1-Reactive T-cell Receptor: Long-term Follow-up and Correlates with Response", Clinical Cancer Research, vol. 21, No. 5, 1 2015, 10 pages.
Zhong, et al. , "Directly cytoplasmic delivery and nuclear targeting delivery of HPMA-MT conjugates in a microtubules dependent fashion," Mol. Pharm., vol. 13, 2016, pp. 3069-3079.
Bai et al., "Enhancement of the in vivo persistence and antitumor efficacy of CD19 chimeric antigen receptor T cells through the delivery of modified TERT mRNA," Cell Discov., vol. 1, 2015, 15 pages.
Boissel et al., "Assembly and Characterization of megaTALs for Hyperspecific Genome Engineering Applications," Methods Mol. . Biol., vol. 1239, 2015, pp. 171-196.
Copolovici, et al., "Cell-penetrating peptides: design, synthesis, and applications," ACS Nano., vol. 8, No. 3, 2014, pp. 1972-1994.
Costa, et al., "Generation of sensory hair cells by genetic programming with a combination of transcription factors," Development, vol. 142, No. 11, 2015, pp. 1948-1959.
Cox, et al.,"Therapeutic genome editing: prospects and challenges," Nat. Med., vol. 21, No. 2, 2015, pp. 121-131.
Cribbs, et al., "Simplified production and concentration of lentiviral vectors to achieve high transduction in primary human T cells," BMC Biotechnol., vol. 13, No. 98, 2013, 8 pages.
Debs, et al., "Targeting of anti-Thy 1.1 monoclonal antibody conjugated liposomes in Thy 1.1 mice after intravenous administration," Biochimica et Biophysica Acta, vol. 901, 1987, pp. 183-190.
Desai, et al., "Interaction of nanoparticles and cell-penetrating peptides with skin for transdermal drug delivery," Mol. Membr. Biol., vol. 27, No. 7, 2010, 19 pages.
Dow, et al., "Intravenous Cytokine Gene Delivery by LipidDNA Complexes Controls the Growth of Established Lung Metastases," Human Gene Therapy, vol. 10, 1999, pp. 2961-2972.
Ebert, et al., "Lymphocyte apoptosis: induction by gene transfer techniques," Gene Therapy, vol. 4, 1997, pp. 296-302.
Extended European Search Report dated Aug. 23, 2019 for European Patent Application No. 17783314.2, 25 pages.
Grandjean, et al., "High-level transgene expression by homologous recombination-mediated gene transfer," Nucleic Acids Research, vol. 39, No. 15 e104, 2011, 15 pages.
Green, et al., "Chemoattractant Signaling between Tumor Cells and Macrophages Regulates Cancel Cell Migration, Metastasis and Neovascularization," PLOS ONE, vol. 4, No. 8, 2009, pp. 1-15.
Heath, et al., "Antibody-targeted liposomes: Increase in specific toxicity of methotrexate-gamma-aspartate," PNAS, vol. 80, 1983, pp. 1377-1381.
Invitation to Pay Fees Dated Apr. 9, 2019 for International Application No. PCT/US2019/014209, 4 Pages.
Invitation to Pay Fees Dated Aug. 6, 2019 for International Application No. PCT/US2019/030263, 3 pages.
Kacherovsky, et al., "Combination of Sleeping Beauty transposition and chemically induced dimerization selection for robust production of engineered cells," Nucleic Acids Research, vol. 40, No. 11e85, 2012, 10 pages.
Kim, et al., "The transcription factor Foxo1 controls central-memory CD8+ T cell responses to infection," Immunity, vol. 39, No. 1, 2013, pp. 286-297.
Koh, et al., "A practical approach to immunotherapy of hepatocellular carcinoma using T cells redirected against hepatitis B virus," Mol. Ther. Nucleic Acids, vol. 2, 2013, 9 pages.
Kurosaki, et al., "Secure Splenic Delivery of Plasmid DNA and Its Application to DNA Vaccine," Biological & Pharmaceutical Bulletin, vol. 36, No. 11, 2013, pp. 1800-1806.
Kurosaki, et al., "Ternary Complexes of pDNA, Polyethylenimine, and y-polyglutamic acid for gene delivery systems," Biomaterials, vol. 30, No. 14, 2009, pp. 2846-2853.
Lin, et al., "CCL21 Cancer Immunotherapy," Cancers, vol. 6, No. 2, 2014, pp. 1098-1110.

(56) References Cited

OTHER PUBLICATIONS

Liu, et al., "Affinity-Tuned ErbB2 or EGFR Chimeric Antigen Receptor T Cells Exhibit an Increased Therapeutic Index against Tumors in Mice," Cancer Res., vol. 75, No. 17, 2015, pp. 3596-3607.
Liu, et al., "Cell-penetrating peptide-mediated delivery of TALEN proteins via bioconjugation for genome engineering," PLoS One, vol. 9, No. 1, 2014, 7 pages.
Liu, et al., "Improved cell-penetrating zinc-finger nuclease proteins for precision genome engineering," Mol. Ther. Nucleic Acids, vol. 4, 2015, 9 pages.
Lopez-Pelaez, et al., "Protein kinase IKKB-catalyzed phosphorylation of IRF5 at Ser462 induces its dimerization and nuclear translocation in myeloid cells," PNAS, vol. 111, No. 49, 2014, pp. 17432-17437.
Mangraviti, et al., "Polymeric nanoparticles for nonviral gene therapy extend brain tumor survival in vivo," ACS Nano., vol. 9, No. 2, 2015, pp. 1236-1249.
Maruyama, et al., "Lipid composition is important for highly efficient target binding and retention of immunoliposomes," PNAS, vol. 87, 1990, pp. 5744-5748.
Moffett, et al., "Hit-and-run programming of therapeutic cytoreagents using mRNA nanocarriers," Nature Communications, vol. 8, No. 1, 2017, pp. 1-13.
Office Action dated Feb. 8, 2017 for U.S. Appl. No. 14/776,661, 13 pages.
Office Action dated May 15, 2018 in U.S. Appl. No. 15/594,344, 13 pages.
Office Action dated Aug. 14, 2018 for U.S. Appl. No. 15/672,106, 15 pages.
Olweus, "Manufacture of CAR-T cells in the body," Nature Biotechnology, vol. 35, 2017, pp. 520-521.
Orcutt, et al., "Engineering an antibody with picomolar affinity to DOTA chelates of multiple radionuclides for pretargeted radioimmunotherapy and imaging," Nucl. Med. Biol., vol. 38, No. 2, 2011, pp. 223-233.
Search Report and Written Opinion dated Oct. 11, 2019 for International Application No. PCT/US2019/030263, 18 pages.
Search Report and Written Opinion dated Jun. 3, 2019 for International Application No. PCT/US2019/014209, 22 pages.
Search Report and Written Opinion dated Jul. 28, 2014 in International Application No. PCT/US2014/029137, 12 pages.
Search Report and Written Opinion dated Jul. 31, 2017 for International Application No. PCT/US2017/027767.
Philip, et al., "In Vivo Gene Delivery," J. Biol. Chem., vol. 268, No. 22, 1993, pp. 16087-16090.
Ren, et al, "Constructions of Polycation-Based Non-Viral DNA Nanoparticles and Polyanion Multilayers via Layer-by-layer Self-Assembly," Macromolecular Rapid Communications, vol. 26, No. 20, 2005, pp. 1633-1638.
Schumann, et al., "Generation of knock-in primary human T cells using Cas9 ribonucleoproteins,"PNAS, vol. 112, No. 22, 2015, pp. 10437-10442.
Smith, et al, "In situ programming of leukaemia-specific T cells using synthetic DNA nanocarriers," Nature Nanotechnology, vol. 12, No. 8, 2017, pp. 813-820.
Stephan, et al. "Enhancing Cell therapies from the Outside In: Cell Surface Engineering Using Synthetic Nanomaterials," Nano Today, vol. 6, No. 3, 2011, 28 pages.
Tejera, et al., "FoxO1 controls effector-to-memory transition and maintenance of functional CD8 T cell memory," J. Immunol., vol. 191, No. 1, 2013, pp. 187-199.
Themeli et al., "Generation of tumor-targeted human T lymphocytes from induced pluripotent stem cells for cancer therapy," Nat. Biotechnol., vol. 31, 2013, pp. 928-933.
Tousignant, et al., "Comprehensive Analysis of the Acute Toxicities Induced by Systemic Administration of Cationic Lipid:Plasmid DNA Complexes in Mice," Human Gene Therapy, vol. 22, 2000, pp. 2493-2513.
Wang, et al., "Highly efficient homology-driven genome editing in human T cells by combining zinc-finger nuclease mRNA and AAV6 donor delivery," Nucleic Acids Res., vol. 44, No. 3, 2016, 9 pages.
Wurm, et al., "Ectopic expression of HOXC6 blocks myeloid differentiation and predisposes to malignant transformation," Exp. Hematol., vol. 42, No. 2, 2014, pp. 114-125.
Xia, et al, "Polyglutamic Acid Based Polyanionic Shielding System for Polycationic Gene Carriers," Chinese Journal of Polymer Science, vol. 34, No. 3, Zhongguo Huaxuehui, CN, 2016, pp. 316-323.
Office Action dated Aug. 5, 2020 for Chilean Application No. 02905-2018, 17 pages.
Office Action dated Oct. 26, 2020 for Colombian Application No. NC2018/0012099, 19 pages.
Chinese Office Action dated Jan. 17, 2022 for Chinese Patent Application No. 201880005741.5, a foreign counterpart to U.S. Appl. No. 16/474,503, 5 pages.
Columbian Action dated Mar. 3, 2022 for Columbian Patent Application No. NC2020/0015686, a foreign counterpart to U.S. Pat. No. 10,188,749, 3 pages.
NCI Thesaurus entry for "DMXAA"; available at ncithesaurus.nci.nih.gov/ncitbrowser/pages/concept_details.jsf?dictionary=NCI_Thesaurus&version=22.01e&code=C2504&ns=ncit&type=synonym&key=null&b=1&n=0&vse=null; last accessed Mar. 16, 2022.
NCI Thesaurus entry for "Hiltonol"; available at ncithesaurus.nci.nih.gov/ncitbrowser/pages/concept_details.jsf?dictionary=NCI_Thesaurus&version=22.01e&code=C1198&ns=ncit&type=synonym&key=1569668399&b=1&n=0&vse=1; last accessed Mar. 16, 2022.
NCI Thesaurus entry for "Imiquimod"; available at ncithesaurus.nci.nih.gov/ncitbrowser/pages/concept_details.jsf?dictionary=NCI_Thesaurus&version=22.01e&code=C1431&ns=ncit&type=synonym&key=265972622&b=1&n=0&vse=null; last accessed Mar. 16, 2022.
Japanese Office Action dated Dec. 7, 2021 for Japanese Patent Application No. 2019-536560, a foreign counterpart to U.S. Appl. No. 16/474,503, 7 pages.
Korean Office Action dated Mar. 4, 2022 for Korean Patent Application No. 10-2018-7032542, a foreign counterpart to U.S. Pat. No. 10,188,749, 12 pages.
NCI Thesaurus entry for "MPLAI"; available at ncithesaurus.nci.nih.gov/ncitbrowser/pages/concept_details.jsf?dictionary=NCI_Thesaurus&version=22.01e&code=C87754&ns=ncit&type=synonym&key=null&b=1&n=0&vse=nul; last accessed Mar. 16, 2022.
Entry from AcronymFinder.com for "PSCA"; available at www.acronymfinder.com/Prostate-Stem-Cell-Antigen-(PSCA).html; last accessed Mar. 16, 2022.
Entry from AcronymFinder.com for "PSMA"; available at https://www.acronymfinder.com/Prostate_Specific-Membrane-Antigen-(PSMA).html; last accessed Mar. 16, 2022.
NCI Thesaurus entry for "ROR1"; available at ncithesaurus.nci.nih.gov/ncitbrowser/pages/concept_details.jsf?dictionary=NCI_Thesaurus&version=22.01e&code=C29879&ns=ncit&type=synonym&key=n1959117208&b=1&n=0&vse=null; last accessed Mar. 16, 2022.
Australian Office Action dated May 9, 2022 for Australian Patent Application No. 2017250295, a foreign counterpart to U.S. Pat. No. 10,188,749, 3 pages.
Chinese Office Action dated Apr. 26, 2022 for Chinese Patent Application No. 201780023532.9, a foreign counterpart to U.S. Pat. No. 10,188,749, 5 pages.
Chinese Office Action dated May 16, 2022 for Chinese Patent Application No. 20198009095.4, a foreign counterpart to U.S. Appl. No. 16/963,119, 7 pages.
Columbian Office Action dated Apr. 19, 2022 for Columbian Patent Application No. NC2018/0012099, a foreign counterpart to U.S. Pat. No. 10,188,749, 9 pages.
Extneded Eurpoean Search Report dated Jun. 24, 2022 for European Application No. 19795782.2 20 pages.
Korean Office Action dated Jun. 21, 2022 for Korean Patent Application No. 10-2018-7032542, a foreign counterpart to U.S. Pat. No. 10,188,749, 7 pages.
Japanese Office Action dated Aug. 9, 2022 for Japanese Application No. 2019-536560, a foreign counterpart to U.S. Pat. No. 11,440,945, 9 pages.

(56) References Cited

OTHER PUBLICATIONS

Shirakura, et al, "T-cell receptor gene therapy targeting melanoma-associated antigen-A4 inhibits human tumor growth in non-obese diabetic/SCID/ycnull nice", Cancer Science, 2012, vol. 103, No. 1, pp. 17-25.

* cited by examiner

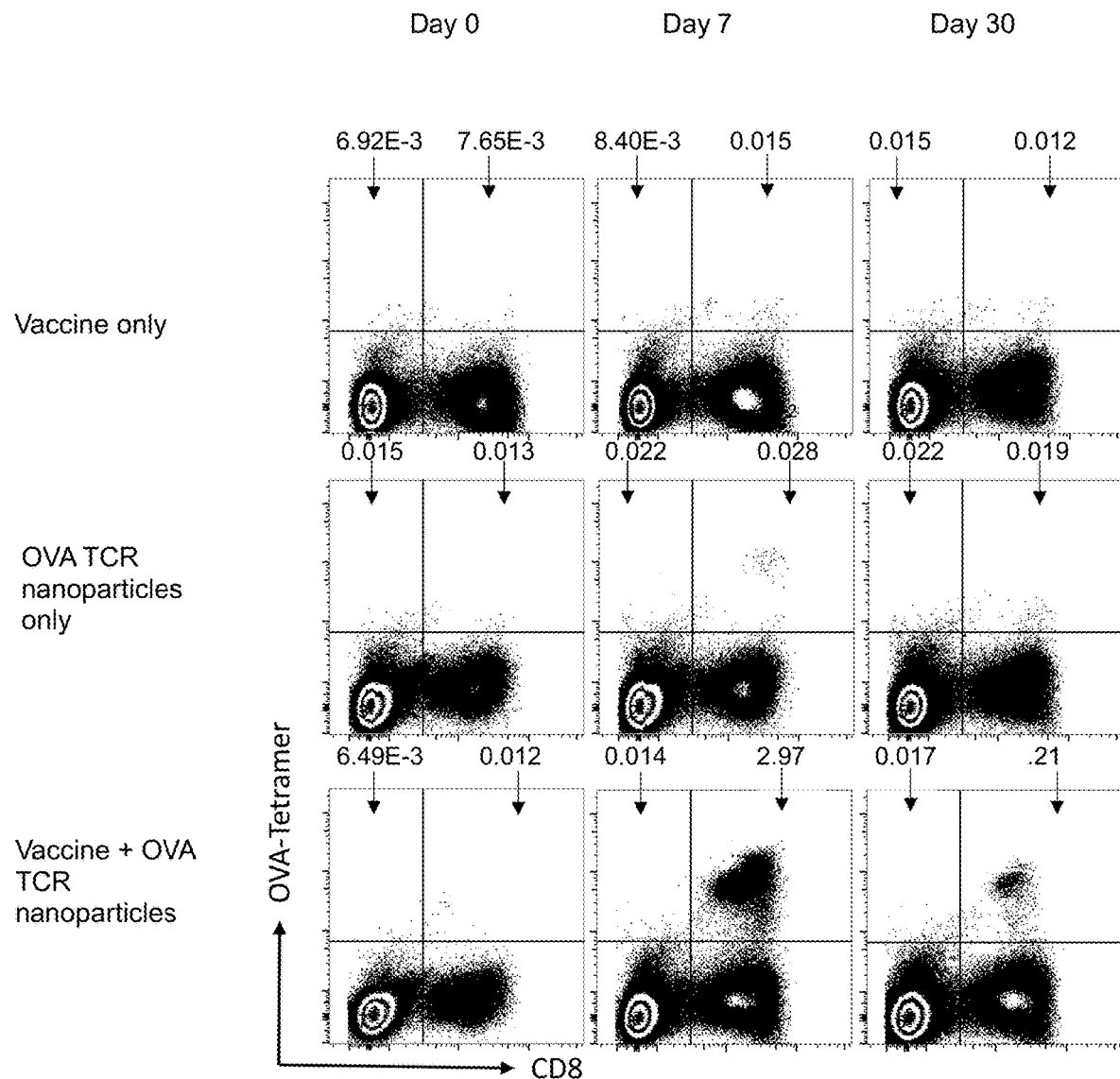

FIG. 5

Representative gene sequence encoding the CD4 transmembrane domain ttcagcagaagcgccgacgcccctgcctaccagcagggccagaatcagctgtacaacgagctgaacctgggcagaa
gggaagagtacgacgtcctggataagcggagaggccgggaccctgagatgggcggcaagcctcggcggaagaac
ccccaggaaggcctgtataacgaactgcagaaagacaagatggccgaggcctacagcgagatcggcatgaagggc
gagcggaggcggggcaagggccacgacggcctgtatcagggcctgtccaccgccaccaaggatacctacgacgcc
ctgcacatgcaggccctgcccccaagg(SEQ ID NO: 40)

FIG. 6

Representative cDNA sequence encoding a murine codon-optimized piggyBac transposase (GenBank accession number: EF587698)

atgggcagcagcctggacgacgagcacatcctgagcgccctgctgcagagcgacgacgagctggtcggcgaggaca
gcgacagcgagatcagcgaccacgtgagcgaggacgacgtgcagtccgacaccgaggaggccttcatcgacgaggt
gcacgaggtgcagcctaccagcagcggctccgagatcctggacgagcagaacgtgatcgagcagcccggcagctcc
ctggccagcaacaggatcctgaccctgccccagaggaccatcaggggcaagaacaagcactgctggtccacctccaa
gagcaccaggcggagcagggtgtccgccctgaacatcgtgagaagccagaggggcccccaccaggatgtgcaggaa
catctacgacccctgctgtgcttcaagctgttcttcaccgacgagatcatcagcgagatcgtgaagtggaccaacgccga
gatcagcctgaagaggcgggagagcatgaccggcgccaccttcagggacaccaacgaggacgagatctacgccttct
tcggcatcctggtgatgaccgccgtgaggaaggacaaccacatgagcaccgacgacctgttcgacagatccctgagcat
ggtgtacgtgagcgtgatgagcagggacagattcgacttcctgatcagatgcctgaggatggacgacaagagcatcagg
cccaccctgcgggagaacgacgtgttcaccccgtgagaaagatctgggacctgttcatccaccagtgcatccagaact
acacccctggcgcccacctgaccatcgacgagcagctgctgggcttcaggggcaggtgccccttcaggatgtatatcccc
aacaagcccagcaagtacggcatcaagatcctgatgatgtgcgacagcggcaccaagtacatgatcaacggcatgcc
ctacctgggcaggggcacccagaccaacggcgtgcccctgggcgagtactacgtgaaggagctgtccaagcccgtcc
acggcagctgcagaaacatcacctgcgacaactggttcaccagcatcccctggccaagaacctgctgcaggagccct
acaagctgaccatcgtgggcaccgtgagaagcaacaagagagagatccccgaggtcctgaagaacagcaggtccag
gcccgtgggcaccagcatgttctgcttcgacggccccctgaccctggtgtcctacaagcccaagcccgccaagatggtgt
acctgctgtccagctgcgacgaggacgccagcatcaacgagagcaccggcaagccccagatggtgatgtactacaac
cagaccaagggcggcgtggacaccctggaccagatgtgcagcgtgatgacctgcagcagaaagaccaacaggtggc
ccatggccctgctgtacggcatgatcaacatcgcctgcatcaacagcttcatcatctacagccacaacgtgagcagcaag
ggcgagaaggtgcagagccggaaaaagttcatgcggaacctgtacatgagcctgacctccagcttcatgaggaagag
gctggaggccccaccctgaagagatacctgagggacaacatcagcaacatcctgcccaacgaggtgcccggcacc
agcgacgacagcaccgaggagcccgtgatgaagaagaggacctactgcacctactgtccagcaagatcagaagaa
aggccaacgccagctgcaagaagtgtaagaaggtcatctgccgggagcacaacatcgacatgtgccagagctgtttctg
a (SEQ ID NO: 142)

SYSTEMS AND METHODS TO IMPROVE VACCINE EFFICACY

CROSS REFERENCE TO RELATED APPLICATION

This application is a US national stage entry of PCT/US2018/012507 filed Jan. 5, 2018, which claims priority to U.S. Provisional Patent Application No. 62/442,903 filed on Jan. 5, 2017, each of which is incorporated by reference in its entirety as if fully set forth herein.

REFERENCE TO SEQUENCE LISTING

The Sequence Listing associated with this application is provided in text format in lieu of a paper copy, and is hereby incorporated by reference into the specification. The name of the text file containing the Sequence Listing is 24K4954_ST25.txt. The text file is 114 KB, was created on Jul. 8, 2019, and is being submitted electronically via EFS-Web.

FIELD OF THE DISCLOSURE

The present disclosure provides systems and methods to increase the efficacy of vaccines that require or are rendered more effective with T cell mediated immunity. The systems and methods utilize polynucleotides that genetically modify T cells to express a T cell receptor specific for an administered vaccine antigen.

BACKGROUND OF THE DISCLOSURE

Lymphocytes are cells of the immune system involved in self/nonself recognition and acquired long-term immunity based on immunological memory. Lymphocytes can broadly be characterized as B cells or T cells. B cells are characterized by the presence of membrane-bound immunoglobulin (antibody) molecules which serve as receptors to bind soluble antigens. T cells are characterized by the presence of membrane-bound T cell receptors (TCR). TCR bind antigens only when the antigen is associated with a major histocompatibility complex (MHC) molecule (i.e., the antigen is not soluble). The specificity of T cell responses is conferred by particular TCR that bind particular antigens.

T lymphocytes include CD4+ T cells and CD8+ T cells. These types of T cells are distinguished in part by their expression of the cell surface molecules CD4 and CD8, respectively. They also, however, have different functions. CD4+ T cells, also referred to as helper T cells ($T_H$) facilitate the activities of other cell types. For example, CD4+TH1 cells secrete various cytokines that activate cytotoxic T cells and macrophages to destroy cells harboring phagocytosed microorganisms. CD4+TH2 cells secrete cytokines that activate B cells to produce antibodies. CD8+ cells are cytotoxic T lymphocytes (CTL) that can directly kill abnormal or infected cells.

Vaccines are formulations that produce an immune system response against a particular pathogen (e.g., infectious microorganism) or aberrant cell type (e.g., cancer cell) by preemptively exposing the immune system to an antigen of the pathogen or aberrant cell type. A pathogen antigen can be an intact, but non-infectious form of a pathogen (e.g., heat-killed). Antigens can also be a protein or protein fragment of the pathogen or a protein or protein fragment preferentially expressed by the aberrant cell type. When the immune system recognizes a vaccine antigen following preemptive exposure, it can lead to long-term immune memory so that if the antigen is encountered again, the immune system can quickly and effectively mount an effective response.

When a vaccine is delivered to a subject, antigen presenting cells (APC) of the immune system take up the antigen component and present it or a fragment thereof to B cells and T cells. B cells that express receptors specific for the presented antigen will produce and secrete antibodies that circulate through the body to elicit a quick, robust immune response if the antigen is encountered again later in life. Standard vaccines are designed to function via such antibody responses created by B cells. The effectiveness of B cell immunity, however, is limited to soluble (i.e., extracellular pathogens). Pathogens that exist intracellularly (e.g., those that cause AIDS, malaria, herpes, and chlamydia) and those bound to a cell surface (e.g., cancer antigens) are not as susceptible to B cell antibodies. Further, the effectiveness of B cell immunity is enhanced when the vaccine antigen is similarly recognized by CD4+ helper T cells.

For antigens that remain cell-associated, T cell mediated immunity is required for effective immunization. Vaccines that require T cell mediated immunity often fail, however, because a host (e.g., person, research animal) does not have T cells expressing particular TCR that recognize and bind the presented vaccine antigen. People with compromised immune systems (e.g., the elderly) are especially vulnerable to this problem, because their declining production of new T cells leads to "holes" in their TCR repertoire. These issues can render vaccines ineffective and leave patients poorly protected against conditions associated with cell-associated antigens (e.g., intracellular infections and cancer).

At present, there are simply no reliable vaccines physicians can use to treat infectious diseases and cancers that require T cell mediated immunity.

SUMMARY OF THE DISCLOSURE

The current disclosure provides systems and methods to enhance the effectiveness of vaccines requiring or rendered more effective by T cell mediated immunity. The systems and methods rely on genetically modifying T cells to express a T cell receptor (TCR) that recognizes and binds a vaccine antigen that is administered to a subject. By ensuring that the subject has T cells expressing a TCR that will recognize and bind the vaccine antigen, the effectiveness of T cell mediated vaccinations is greatly expanded.

Particular embodiments include administering a polynucleotide to a subject wherein the polynucleotide encodes a TCR that binds a vaccine antigen that is administered to the subject.

In particular embodiments, the polynucleotide is administered to the subject as part of a nanoparticle (NP). The NP can include features that enhance the delivery and/or expression of the polynucleotide. For example, in particular embodiments, the NP includes a carrier molecule that condenses and protects the polynucleotide from enzymatic degradation. In particular embodiments, the NP includes a coating that shields the encapsulated polynucleotide and reduces or prevents off-target binding.

In particular embodiments, the NP includes a selective T cell targeting and delivery agent (T-DA). The T-DA allows the NP to be administered to a subject and results in selective delivery of the polynucleotide to selected T cells. Selective modification of CD4+ T cells to express a TCR is particularly useful to improve the efficacy of B-cell mediated vaccinations. Selective modification of CD8+ cytotoxic T cells to express a TCR is particularly useful to improve T cell mediated vaccinations. Both approaches provide vaccine antigen recognizing capabilities to T cells. Importantly, in embodiments incorporating a T-DA, a subject's existing T cells can be modified in vivo following, for example, intramuscular administration of the NP.

NP can also include other features to facilitate expression of polynucleotides delivered to a subject's T cells. For example, the NP can include endosomal release agents and/or nuclear targeting agents. Endosomal release agents promote escape of the delivered polynucleotide from the targeted T cell's endosome. Nuclear targeting agents direct polynucleotides towards and/or into the nucleus of the targeted cell.

Particular embodiments combine aspects of these features. For example, a NP can include (i) a polynucleotide encoding a TCR that binds a vaccine antigen that is administered to a subject; (ii) a condensing carrier molecule; (iii) a coating; (iv) a T-DA that selectively directs the NP to defined T cells (e.g., CD4+ or CD8+ T cells); (v) an endosomal release agent; and (iv) a nuclear targeting agent. This NP can be administered to the subject within a clinically relevant time window of receiving a vaccine antigen.

The systems and methods disclosed herein are particularly useful to increase the efficacy of vaccines that treat chronic conditions that require strong T cell immunity. Examples of such chronic conditions include chronic infections (e.g., acquired immune deficiency syndrome (AIDS), malaria, herpes, chlamydia, Epstein Barr virus (EBV), Pneumococcus, and Hepatitis B) and cancers.

BRIEF DESCRIPTION OF THE FIGURES

Many of the drawings submitted herein are better understood in color. Applicants consider the color versions of the drawings as part of the original submission and reserve the right to present color images of the drawings in later proceedings.

FIGS. 3A-3C. Intramuscular injections of DNA-carrying nanoparticles (NPs) can efficiently introduce vaccine-specific TCRs into the peripheral T cell repertoire. (3A) Schematic of the T cell-targeted DNA nanoparticle used in described experiments. The NPs are prepared by mixing plasmid DNA with poly(β-amino ester) polymer, which condenses the plasmid DNA into nano-sized complexes. The particles were targeted by coupling the anti-CD8 antibody to polyglutamic acid (PGA), forming a conjugate that was electrostatically adsorbed to the particles. The inset is an electron micrograph of the NPs; scale bar, 100 nm. Also depicted are the two nanoparticle-encapsulated plasmids, which encode the OVA-specific OT-1 TCR and the hyperactive iPB7 transposase. (3B) Cytometric analysis of lymphocytes in draining lymph nodes. The percentages of cells in the bottom left quadrant and bottom right quadrant of each panel are, respectively: 82.7 and 17.3 (Vaccine only, Day 0); 75.1 and 24.8 (Vaccine only, Day 7); 85.3 and 14.7 (Vaccine only, Day 30); 85.3 and 14.7 (OVA TCR nanoparticles only, Day 0); 84.2 and 15.7 (OVA TCR nanoparticles only, Day 7); 87.5 and 12.4 (OVA TCR nanoparticles only, Day 30); 86.7 and 13.2 (Vaccine+OVA TCR nanoparticles, Day 0); 80.3 and 16.7 (Vaccine+OVA TCR nanoparticles, Day 7); 80.6 and 19.1 (Vaccine+OVA TCR nanoparticles, Day 30). (3C) Plots showing absolute numbers of NP-programmed OVA-reactive memory T cells on day 30.

FIG. 5. Representative gene sequence encoding the CD4 transmembrane domain (SEQ ID NO: 40).

FIG. 6. Representative cDNA sequence encoding a murine codon-optimized piggyBac transposase (GenBank accession number: EF587698; SEQ ID NO: 142).

DETAILED DESCRIPTION

Figure 1:
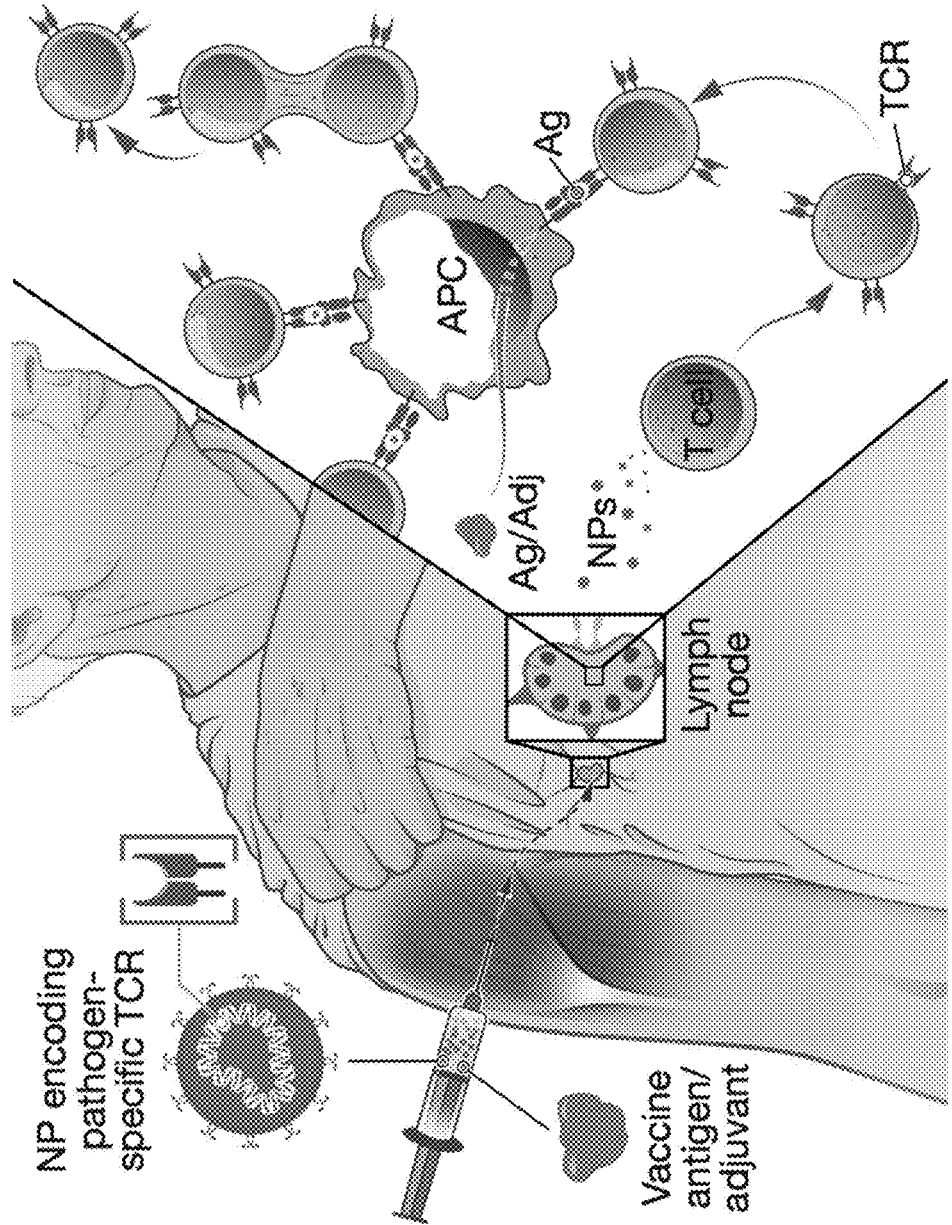
FIG. 1. Schematic illustrating the overall approach to prevent vaccine failure through rational T-cell receptor programming. Nanoparticles (NPs) are used to introduce engineered TCR genes into circulating host T cells, endowing them with antigen-recognizing capabilities, which are then selectively expanded using a peptide vaccine recognized by the transferred TCR.

Lymphocytes are cells of the immune system involved in self/nonself recognition and acquired long-term immunity based on immunological memory. Lymphocytes can broadly be characterized as B cells or T cells. B cells are characterized by the presence of membrane-bound immunoglobulin (antibody) molecules which serve as receptors to bind soluble antigens. T cells are characterized by the presence of membrane-bound T cell receptors (TCR). TCR bind antigens only when the antigen is associated with a major histocompatibility complex (MHC) molecule (i.e., the antigen is not soluble). The specificity of T cell responses is conferred by particular TCR that bind particular antigens.

T lymphocytes include CD4+ T cells and CD8+ T cells. These types of T cells are distinguished in part by their expression of the cell surface molecules CD4 and CD8, respectively. They also, however, have different functions. CD4+ T cells, also referred to as helper T cells ($T_H$) facilitate the activities of other cell types. For example, CD4+TH1 cells secrete various cytokines that activate cytotoxic T cells and macrophages to destroy cells harboring phagocytosed microorganisms. CD4+TH2 cells secrete cytokines that activate B cells to produce antibodies. CD8+cells are cytotoxic T lymphocytes (CTL) that can directly kill abnormal or infected cells.

Vaccines are formulations that produce an immune system response against a particular antigen by preemptively exposing the immune system to the antigen. A pathogen antigen can be an intact, but non-infectious form of a pathogen (e.g., heat-killed). Antigens can also be a protein or protein fragment of a pathogen or a protein or protein fragment expressed by an aberrant cell type (e.g. a cancer cell). When the immune system recognizes an antigen following preemptive exposure, it can lead to long-term immune memory so that if the antigen is encountered again, the immune system can quickly and effectively mount an effective response.

When a vaccine is delivered to a subject, antigen presenting cells (APC) of the immune system take up the antigen component and present it or a fragment thereof to B cells and T cells. B cells that express receptors specific for the presented antigen will produce and secrete antibodies that circulate through the body to elicit a quick, robust immune response if the antigen is encountered again later in life. Standard vaccines are designed to function via such antibody responses created by B cells. The effectiveness of B cell immunity, however, is limited to soluble (i.e., extracellular) pathogens. Pathogens that exist intracellularly (e.g., those that cause AIDS, malaria, herpes, and chlamydia) or remain cell-associated (e.g., cancer cell antigens) are not as susceptible to B cell antibodies. Further, the effectiveness of B cell immunity is enhanced when the vaccine antigen is similarly recognized by CD4+ helper T cells.

For antigens that are cell-associated (e.g., intracellular or membrane-bound), T cell mediated immunity is required for effective immunization. Vaccines that require T cell mediated immunity often fail, however, because a host (e.g., person, research animal) does not have T cells expressing particular TCR that recognize and bind the presented vaccine antigen. People with compromised immune systems (e.g., the elderly) are especially vulnerable to this problem, because their declining production of new T cells leads to "holes" in their TCR repertoire. These issues can render vaccines ineffective and leave patients poorly protected against infection by intracellular pathogens and/or cancer.

At present, there are simply no reliable vaccines physicians can use to treat infectious diseases and cancers that require T cell mediated immunity.

The current disclosure provides systems and methods to enhance the effectiveness of vaccines requiring or rendered more effective by T cell mediated immunity. The systems and methods rely on genetically modifying T cells to express a T cell receptor (TCR) that recognizes and binds a vaccine antigen that is administered to a subject. By ensuring that the subject has T cells expressing TCR that will recognize and bind the vaccine antigen, the effectiveness of T cell mediated vaccinations is greatly expanded.

Particular embodiments include administering a polynucleotide to a subject wherein the polynucleotide encodes a TCR that binds a vaccine antigen that is administered to the subject.

In particular embodiments, the polynucleotide is administered to the subject as part of a nanoparticle (NP). The NP can include features that enhance the delivery and/or expression of the polynucleotide. For example, in particular embodiments, the NP includes a carrier molecule that condenses and protects the polynucleotide from enzymatic degradation. As disclosed in more detail elsewhere herein, such carriers can include positively charged lipids and/or polymers. Particular embodiments utilize poly(β-amino ester).

In particular embodiments, the NP includes a coating that shields the encapsulated polynucleotide and reduces or prevents off-target binding. Off-target binding is reduced or prevented by reducing the surface charge of the NP to neutral or negative. As disclosed in more detail elsewhere herein, coatings can include neutral or negative polymer- and/or liposome-based coatings. Particular embodiments utilize polyglutamic acid (PGA) as a NP coating. When used, the coating need not necessarily coat the entire NP, but must be sufficient to reduce off-target binding by the NP.

In particular embodiments, the NP includes a selective T cell targeting and delivery agent (T-DA). The T-DA allows the NP to be administered to a subject and results in selective delivery of the polynucleotide to selected T cells. Selective modification of CD4+ T cells to express a TCR is particularly useful to improve the efficacy of B-cell mediated vaccinations. Selective modification of CD8+ cytotoxic T cells to express a TCR is particularly useful to improve T cell mediated vaccinations. Both approaches provide vaccine antigen recognizing capabilities to T cells. Importantly, in embodiments incorporating a T-DA, a subject's existing T cells can be modified in vivo following, for example, intramuscular administration of the NP.

NP can also include other features to facilitate expression of polynucleotides delivered to a subject's T cells. For example, the NP can include endosomal release agents and/or nuclear targeting agents. Endosomal release agents promote escape of the delivered polynucleotide from the targeted T cell's endosome. Nuclear targeting agents direct polynucleotides towards and/or into the nucleus of the targeted cell.

Particular embodiments combine aspects of these features. For example, a NP can include (i) a polynucleotide encoding a TCR that binds a vaccine antigen that is administered to the subject; (ii) a positively-charged carrier; (iii) a neutral or negatively-charged coating; (iv) a T-DA that selectively directs the NP to defined T cells (e.g., CD4+ or CD8+ T cells); (v) an endosomal release agent; and (vi) a nuclear targeting agent. This NP can be administered to the subject within a clinically relevant time window of receiving a vaccine antigen.

The systems and methods disclosed herein are particularly useful to increase the efficacy of vaccines that treat chronic infections and cancers that require strong T cell immunity. Examples of such chronic infections include acquired immune deficiency syndrome (AIDS), malaria, herpes, chlamydia, Epstein Barr virus (EBV), Pneumococcus, and Hepatitis B.

Figure 2:
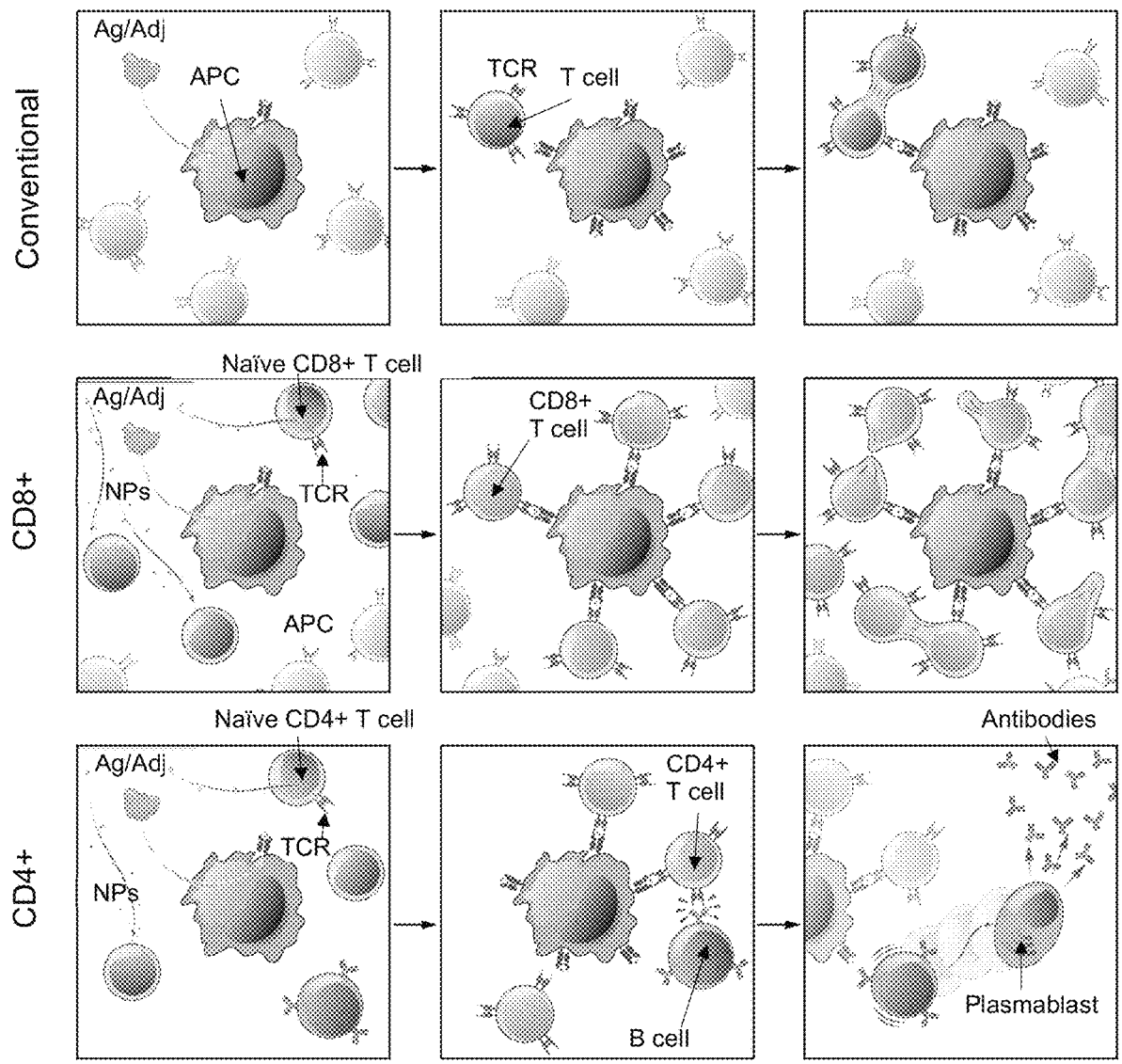
FIG. 2. Schematics illustrating advantages of the disclosed systems and methods over conventional vaccines: The upper panel shows how injecting vaccine antigen/adjuvant often fails because immunized individuals have too few T cells with the appropriate receptors. The middle panel illustrates how NPs can be used to introduce engineered TCR genes into circulating T cells, endowing them with antigen-recognizing capabilities. These are then selectively expanded using a peptide vaccine recognized by the transferred TCR. The lower panel shows how programming CD4 helper T cells with vaccine-specific TCRs can boost the production of protective antibodies by generating high-affinity memory B cells.

FIG. 2 provides schematic representations underlying the systems and methods disclosed herein. The top 3 panels depict the poor T cell priming observed with conventional vaccine antigen administrations. The middle 3 panels depict genetic reprogramming of CD8+ T cells to recognize administered vaccine antigen to yield increased T cell priming to support T cell mediated immunity. The bottom 3 panels depict genetic reprogramming of CD4+ T cells to recognize administered vaccine antigen to yield increased T cell priming to help and support robust antibody production by B cells. Thus, particular embodiments include administering a polynucleotide to a subject wherein the polynucleotide genetically reprograms a T cell to express a TCR that binds a vaccine antigen that is administered to the subject.

Aspects of the disclosure are now described in more detail and in the following order: (I) TCRs; (II) polynucleotides (PN) encoding engineered TCRs; (III) nanoparticles (NP); (IV) T cell targeting and delivery agents (T-DA); (V) endosomal release agents (ERA); (VI) nuclear targeting agents (NTA); (VII) vaccine antigens; (VIII) vaccine adjuvants; (IX) compositions; (X) kits; and (XI) methods of use.

I. T Cell Receptors (TCRs). As indicated, TCR are molecules found on the surface of T cells that recognize and bind antigens associated with major histocompatibility complex (MHC) molecules.

Each TCR includes two disulfide-linked heterodimeric transmembrane proteins. That is, each TCR is a heterodimer. In 95% of T cells in peripheral blood, each TCR includes an alpha (α) chain and a beta (β) chain. The remaining 5% of T cells in peripheral blood, include a gamma (γ) chain and a delta (Δ) chain.

Each TCR chain includes a variable domain, which confers the antigen specificity of the T cell. These variable domains are similar to those of Ig variable (V) chains.

Other portions of the chains include several invariant domains such as a constant domain, a transmembrane domain, and a short cytoplasmic tail. Membrane-anchored C-terminal domains are analogous to Ig constant (C) domains.

To achieve functional form, TCR associate non-covalently with CD3, forming the TCR-CD3 membrane complex. CD3, the signal transduction element of the TCR, is composed of a group of invariant proteins called γ, Δ, epsilon (Σ), zeta (Z) and eta (H) chains. The γ, Δ, and Σ chains are structurally-related, each containing an Ig-like extracellular constant domain followed by a transmembrane region and a cytoplasmic domain of more than 40 amino acids. The Z and H chains have a distinctly different structure: both have a very short extracellular region of only 9 amino acids, a transmembrane region and a long cytoplasmic tail including 113 and 115 amino acids in the Z and H chains, respectively. The invariant protein chains in the CD3 complex associate to form noncovalent heterodimers of the Σ chain with a γchain (Σγ) or with a Δ chain (ΣΔ) or of the Z and H chain (ZH), or a disulfide-linked homodimer of two Z chains (ZZ). 90% of the CD3 complex incorporate the ZZ homodimer.

The cytoplasmic regions of the CD3 chains include a motif designated the immunoreceptor tyrosine-based activation motif (ITAM). This motif is found in a number of other receptors including the Ig-α/Ig-β heterodimer of the B-cell receptor complex and Fc receptors for IgE and IgG. The ITAM sites associate with cytoplasmic tyrosine kinases and participate in signal transduction following TCR-mediated triggering. In CD3, the γ, Δ and Σ chains each contain a single copy of ITAM, whereas the Z and H chains harbor three ITAMs in their long cytoplasmic regions. Indeed, the Z and H chains have been ascribed a major role in T cell activation signal transduction pathways.

There are numerous ways to identify and select particular TCR for use within particular applications of the disclosed systems and methods. For example, the sequences of numerous TCR that bind particular antigen fragments are known and publicly available.

TCR can also be identified for use with a particular vaccine by, for example, isolating T cells that bind a particular vaccine antigen/MHC complex and sequencing the TCR chains binding the complex. As examples, antigen-specific T cells may be induced by in vitro cultivation of isolated human T cells in the presence of an antigen/MHC complex. TCR genes encoding TCR that bind the antigen/MHC complex can be readily cloned by, for example, the 5' RACE procedure using primers corresponding to the sequences specific to the TCR α-chain gene and the TCR β-chain gene.

Various analogs of natural TCR ligands have been produced which include extracellular domains of MHC molecules bound to a specific peptide antigen. Several such analogs have been purified as detergent extracts of lymphocyte membranes or produced as recombinant proteins (see, for example, Sharma et al., PNAS. 88: 11465-69, 1991; Kozono et al., Nature 369: 151-54, 1994; Arimilli et al., J. Biol. Chem. 270: 971-77, 1995; Nag, PNAS 90: 1604-08, 1993; Nag et al., J. Biol. Chem. 271: 10413-18, 1996; Rhode et al., J. Immunol. 157: 4885-91, 1996; Fremont et al., Science 272: 1001, 1996; Sharma et al., Proc. Natl. Acad. Sci. USA 88: 11405, 1991; Nicolle et al., J. Clin. Invest. 93: 1361, 1994; Spack et al., CNS Drug Rev. 4: 225, 1998). Such analogs can be used to isolate T cells to then sequence the TCR of interest for a particular application.

In particular embodiments, it may be necessary to pair TCR chains following sequencing (i.e., to perform paired chain analysis). Various methods can be utilized to pair isolated α and β chains that bind an antigen/MHC complex such that the pairing results in a TCR that binds to an antigen/MHC complex when expressed by a genetically modified T cell. In particular embodiments post-sequencing pairing may be unnecessary or relatively simple, for example in embodiments in which the α and β chain pairing information is not lost in the procedure, such as if one were to sequence from single cells. In particular embodiments, chain pairing may be assisted in silico by computer methods. For example, specialized, publicly available immunology gene alignment software is available from IMGT, JOIN-SOLVER, VDJSolver, SoDA, iHMMune-align, or other similar tools for annotating VDJ gene segments.

In particular embodiments, chain pairing may be performed using VDJ antibodies. For example, one may obtain antibodies for the identified segments and use the antibodies to purify a subset of cells that express that gene segment in their (surface) receptors (e.g. using FACS, or immunomagnetic selection with microbeads). One may then sequence from this subset of cells which have been purified for the desired gene segments. If necessary, this secondary sequencing may be done more deeply (i.e. at a higher resolution) than the first round of sequencing. In this second sequence data set, there will be far fewer induced clonotypes, greatly easing the task of chain pairing. Depending on the gene segments, there may be only one induced α chain and one induced β chain for example.

In particular embodiments, chain pairing may be performed using multiwell sequencing. For example, one may isolate gene segment purified cells or unpurified cells into a microwell plate, where each microwell has a very low number of cells. One can amplify and sequence the cells in each well individually, which provides another means to pair the chains of interest by sequencing on a single cell basis, facilitating the pairing of induced α and β chains. Assays such as PairSEQ® (Adaptive Biotechnologies Corp., Seattle, Wash.) have also been developed.

Following selection and/or identification of a TCR of interest for a particular vaccine application, any portion of the TCR can be used and variants of the TCR can be used, so long as when expressed by a genetically modified T cell, the expressed TCR binds the intended vaccine/MHC complex and results in T cell activation.

In particular embodiments, an engineered TCR includes a single chain T cell receptor (scTCR) including Vα/β and Cα/β chains (e.g., Vα-Cα, Vβ-Cβ, Vα-Vβ) or including Vα-Cα, Vβ-Cβ, Vα-Vβ pair specific for a target of interest (e.g., peptide-MHC complex).

In particular embodiments, engineered TCR include a sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a known or identified TCR Vα, Vβ, Cα, or Cβ, wherein each CDR includes zero changes or at most one, two, or three changes, from a TCR or fragment or derivative thereof that specifically binds to the target of interest.

In particular embodiments, engineered TCR include Vα, Vβ, Cα, or Cβ regions derived from or based on a Vα, Vβ, Cα, or Cβ of a known or identified TCR (e.g., a high-affinity TCR) and includes one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the Vα, Vβ, Cα, or Cβ of a known or identified TCR. An insertion, deletion or substitution may be anywhere in a Vα, Vβ, Cα, or Cβ region, including at the amino- or carboxy-terminus or both ends of these regions, provided that each CDR includes zero changes or at most one, two, or three changes and provides a target binding domain containing a modified Vα, Vβ, Cα, or Cβ region can still specifically bind its target with an affinity and action similar to wild type.

There are two types of MHC molecules that can be bound by TCR: MHC class I molecules and MHC class II molecules. In the context of expressed TCR and particular uses described herein, it can be useful to express MHC class I restricted or MHC class II restricted TCR. A discussion of these distinct classes of MHC molecules is therefore provided.

MHC Class I molecules include a polymorphic heavy chain (a) non-covalently associated with a monomorphic (in humans) non-MHC encoded light chain protein of 12 kDa, termed $\beta_2$ microglobulin ($\beta_2$m). The heavy a chain is a polymorphic transmembrane glycoprotein of 45 kDa including 3 extracellular domains, each including 90 amino acids ($\alpha_1$ at the N-terminus, $\alpha_2$ and $\alpha_3$), a transmembrane region of 40 amino acids and a cytoplasmic tail of 30 amino acids. The $\alpha_1$ and $\alpha_2$ domains, the membrane distal domains, form the peptide-binding groove or cleft having a sufficient size to bind a peptide of 8-10 amino acids, whereas the $\alpha_3$ domain is proximal to the plasma membrane. $\beta_2$m has a single immunoglobulin (Ig)-like domain, not anchored to the plasma membrane, and interacts mainly with the $\alpha_3$ chain, which also possesses a characteristic Ig fold. In humans, there are three a chain genes, called HLA-A, HLA-B and HLA-C, for each of which multiple alleles have been identified. In mice, there are three a chain genes, called H-2K, H-2D and H-2L.

MHC Class II molecules include two different polypeptide chains, a 33-kD α chain and a 28-kDa β chain, which associate by noncovalent interactions. Like class I MHC molecules, class II MHC molecules are membrane-bound glycoproteins that contain extracellular domains, a transmembrane segment and a cytoplasmic tail. Each chain in these noncovalent heterodimeric complexes includes two extracellular domains: $\alpha_1$ and $\alpha_2$ domains and 1 and β2 domains. The membrane-distal domain of a class II molecule is composed of the α1 and β1 domains and forms the peptide-binding groove or cleft having a sufficient size to bind a peptide, which is typically of 13-18 amino acids. The membrane-proximal domains, α2 and β2, have structural similarities to Ig constant (C) domains.

The genes that encode the various polypeptide chains that associate to form MHC complexes in mammals have been studied and described in extensive detail. In humans, MHC molecules (with the exception of class I $\beta_2$m) are encoded in the HLA region of the genome, located on chromosome 6. There are three class I MHC α-chain-encoding loci, termed HLA-A, HLA-B and HLA-C. In the case of MHC class II proteins, there are three pairs of α and β chain loci, termed HLA-DR (A and B), HLA-DP (A and B), and HLA-DQ (A and B). In rats, the class I α gene is designated RT1.A, while the class II genes are termed RT1.Bα and RT1.Bβ. More detailed description regarding the structure, function and genetics of MHC complexes can be found, for example, in Immunobiology: The Immune System in Health and Disease by Janeway and Travers, Current Biology Ltd./Garland Publishing, Inc. (1997), and in Bodmer et al. (1994) "Nomenclature for factors of the HLA system" Tissue Antigens vol. 44, pages 1-18.

During T cell development, T cells in the thymus are presented with peptide/HLA complexes and undergo selection based on this interaction. T cell selection can result in T cells that are restricted to interactions with a particular class of HLA molecule, known as HLA-restriction. For example, during selection a T cell can differentiate to become a class I restricted CD8+ T cell due to effective interactions between the TCR and a peptide/HLA class I complex, or can become a class II restricted CD4+ T cell due to effective interactions between the TCR and a peptide/HLA class II complex. The complementarity regions 1-3 (CDRs 1-3) of a TCR engage the peptide/HLA complex. Therefore, amino acid sequences of CDRs 1-3 can be determinants of whether a T cell is HLA class I or HLA class II restricted. Coreceptor expression is also an important feature of T cell class restriction. To initiate signaling for T cell activation in response to an antigen, HLA class I molecules can interact with CD4+ coreceptors, whereas HLA class II molecules can interact with CD8+ coreceptors. Therefore, a T cell engineered to express a TCR that engages a peptide/HLA class I complex can become activated if it expresses the coreceptor CD8, whereas a T cell engineered to express a TCR that engages a peptide/HLA class II complex can become activated if it expresses the coreceptor CD4.

Thus, absent genetic engineering to alter the following, CD8+ T cells recognize MHC class I molecules while CD4+ T cells recognize MHC class II molecules. In particular embodiments then, CD8+ T cells can be genetically modified to express HLA-class I restricted TCR and CD4+ T cells can be genetically modified to express HLA-class II restricted TCR.

In particular embodiments, TCR can include: α chain: MNSSLDFLILILMFGGTSSNSVKQTGQITVSE-GASVTMNCTYTSTGYPTLFWYVEYPSKPLQLLQR ETMENSKNFGGGNIKDKNSPIVKYSVQVSDSAVYY-CLLRNHDKLIFGTGTRLQVFPNIQNPDPAVY QLRD-SKSSDKSVCLFTDFDSQTNVSQSKDSDVYITDKTVL DMRSMDFKSNSAVAWSNKSDFACA NAFNN-SIIPEDTFFPSPESSCDVKLVEKS-FETDTNLNFQNLSVIGFRILLLKVAGFNLL-MTLRLWSS (SEQ ID NO: 1); and β chain: MGPGLLCWVLLCLLGAGSVETGVTQSPTH-LIKTRGQQVTLRCSSQSGHNTVSWYQQALGQGPQ FIFQYYREEENGRGNFPPRFSGLQFPNYS-SELNVNALELDDSALYLCASSQDSYNEQFFGPGTRL TVLEDLKNVFPPEVAVFEPSE-AEISHTQKATLVCLATGFYPDHVELSWWVNGKEV-HSGVSTDPQP LKEQPALNDSR YCLSSRLRVSATFWQNPRNHFRCQVQFYGLSEND-EVTQDRAKPVTQIVSAEA WGRADCGFTS-ESYQQGVLSATILYEILLGKATLYAVLVSALVL-MAMVKRKDSRG (SEQ ID NO: 2).

In particular embodiments, TCR can include: α chain: MNSSLDFLILILMFGGTSSNSVKQTGQITVSE-GASVTMNCTYTSTGYPTLFWYVEYPSKPLQLLQR ETMENSKNFGGGNIKDKNSPIVKYSVQVSDSAVYY-CLLRNHDKLIFGTGTRLQVFPNIQNPDPAVY QLRD-SKSSDKSVCLFTDFDSQTNVSQSKDSDVYITDKTVL DMRSMDFKSNSAVAWSNKSDFACA NAFNN- SIIPEDTFFPSPESSCDVKLVEKSFETDTNLNFQNLSVIGFRILLLKVAGFNLLMTLRLWSS (SEQ ID NO: 1); and β chain: MGPGLLCWVLLCLLGAGSVETGVTQSPTHLIKTRGQQVTLRCSSQSGHNTVSWYQQALGQGPQFIFQYYREEENGRGNFPPRFSGLQFPNYSSELNVNALELDDSALYLCASSLAGGYGDTQYFGPGTRLTVLEDLKNVFPPEVAVFEPSEAEISHTQKATLVCLATGFYPDHVELSWWVNGKEVHSGVSTDP QPLKEQPALNDSRYCLSSRLRVSATFWQNPRNHFRCQVQFYGLSENDEWTQDRAKPVTQIVSAE AWGRADCGFTSESYQQGVLSATILYEILLGKATLYAVLVSALVLMAMVKRKDSRG (SEQ ID NO: 3). In particular embodiments, TCR can include: α chain: MKKLLAMILWLQLDRLSGELKVEQNPLFLSMQEGKNYTIYCNYSTTSDRLYWYRQDPGKSLESLF VLLSNGAVKQEGRLMASLDTKARLSTLHITAAVHDLSATYFCAVGNYGGSQGNLIFGKGTKLSVKP NIQNPDPAVYQLRDSKSSDKSVCLFTDFDSQTNVSQSKDSDVYITDKTVLDMRSMDFKSNSAVAW SNKSDFACANAFNNSIIPEDTFFPSPESSCDVKLVEKSFETDTNLNFQNLSVIGFRILLLKVAGFNLL MTLRLWSS (SEQ ID NO: 4); and β chain: MGPGLLCWVLLCLLGAGSVETGVTQSPTHLIKTRGQQVTLRCSSQSGHNTVSWYQQALGQGPQFIFQYYREEENGRGNFPPRFSGLQFPNYSSELNVNALELDDSALYLCASSQDSYNEQFFGPGTRLTVLEDLKNVFPPEVAVFEPSEAEISHTQKATLVCLATGFYPDHVELSWWVNGKEVHSGVSTDPQP LKEQPALNDSRYCLSSRLRVSATFWQNPRNHFRCQVQFYGLSENDEVTQDRAKPVTQIVSAEA WGRADCGFTSESYQQGVLSATILYEILLGKATLYAVLVSALVLMAMVKRKDSRG (SEQ ID NO: 2).

In particular embodiments, TCR can include: α chain: MKKLLAMILWLQLDRLSGELKVEQNPLFLSMQEGKNYTIYCNYSTTSDRLYWYRQDPGKSLESLF VLLSNGAVKQEGRLMASLDTKARLSTLHITAAVHDLSATYFCAVGNYGGSQGNLIFGKGTKLSVKP NIQNPDPAVYQLRDSKSSDKSVCLFTDFDSQTNVSQSKDSDVYITDKTVLDMRSMDFKSNSAVAW SNKSDFACANAFNNSIIPEDTFFPSPESSCDVKLVEKSFETDTNLNFQNLSVIGFRILLLKVAGFNLL MTLRLWSS (SEQ ID NO: 4); and β chain: MGPGLLCWVLLCLLGAGSVETGVTQSPTHLIKTRGQQVTLRCSSQSGHNTVSWYQQALGQGPQFIFQYYREEENGRGNFPPRFSGLQFPNYSSELNVNALELDDSALYLCASSLAGGYGDTQYFGPGTRLTVLEDLKNVFPPEVAVFEPSEAEISHTQKATLVCLATGFYPDHVELSWWVNGKEVHSGVSTDP QPLKEQPALNDSRYCLSSRLRVSATFWQNPRNHFRCQVQFYGLSENDEWTQDRAKPVTQIVSAE AWGRADCGFTSESYQQGVLSATILYEILLGKATLYAVLVSALVLMAMVKRKDSRG (SEQ ID NO: 3). In particular embodiments, TCR can include a human α chain variable domain having a sequence of: MNSSLDFLILILMFGGTSSNSVKQTGQITVSEGASVTMNCTYTSTGYPTLFWYVEYPSKPLQLLQRETMENSKNFGGGNIKDKNSPIVKYSVQVSDSAVYYCLLRNHDKLIFGTGTRLQVFPN (SEQ ID NO: 5) or MKKLLAMILWLQLDRLSGELKVEQNPLFLSMQEGKNYTIYCNYSTTSDRLYWYRQDPGKSLESLF VLLSNGAVKQEGRLMASLDTKARLSTLHITAAVHDLSATYFCAVGNYGGSQGNLIFGKGTKLSVKP N (SEQ ID NO: 6). In particular embodiments, TCR can include a human β chain variable domain having a sequence of: MGPGLLCWVLLCLLGAGSVETGVTQSPTHLIKTRGQQVTLRCSSQSGHNTVSWYQQALGQGPQFIFQYYREEENGRGNFPPRFSGLQFPNYSSELNVNALELDDSALYLCASSQDSYNEQFFGPGTRLTVLE (SEQ ID NO: 7) or MGPGLLCWVLLCLLGAGSVETGVTQSPTHLIKTRGQQVTLRCSSQSGHNTVSWYQQALGQGPQFIFQYYREEENGRGNFPPRFSGLQFPNYSSELNVNALELDDSALYLCASSLAGGYGDTQYFGPGTRLTVLE (SEQ ID NO: 8). In particular embodiments, TCR can include a human α chain variable domain having a CDR3 sequence of: CLLRNHDKLIF (SEQ ID NO: 9) or CAVGNYGGSQGNLIF (SEQ ID NO: 10). In particular embodiments, TCR can include a human β chain variable domain having a CDR3 sequence of: CASSQDSYNEQFF (SEQ ID NO: 11) or CASSLAGGYGDTQYF (SEQ ID NO: 12). TCRs including these α and β CDR3, variable domain, and/or chain sequences bind Mesothelin (MSLN) peptide-HLA complex. In particular embodiments, TCRs including these α and β CDR3, variable domain, and/or chain sequences bind to a SLLFLLFSL (SEQ ID NO: 13):HLA-A*201 complex or a VLPLTVAEV (SEQ ID NO: 14):HLA-A*201 complex. MSLN is a tumor antigen that is highly expressed in many human cancers, including malignant mesothelioma and pancreatic, ovarian, and lung adenocarcinomas. It is an attractive target for cancer immunotherapy because its normal expression is limited to mesothelial cells, which are dispensable. In particular embodiments, the α and β genes of human TCR specific for MSLN have been codon optimized and linked by a porcine teschovirus-1 2A element. TCR sequences specific for human MSLN are described in Stromnes, I M et al. (2015) Cancer cell 28(5): 638-652 and WO 2017/112944.

In particular embodiments, TCR can include a murine Vα4 chain having a CDR3 sequence of: LDYANKMI (SEQ ID NO: 15) and a Vβ9 chain having a CDR3 sequence of: PQDTQYFF (SEQ ID NO: 16) described in Stromnes, I M et al. (2015), supra. The murine TCR, called $TCR_{1045}$, was derived from T cell clones of $MsIn^{-/-}$ mice engineered to express recombinant murine MsIn and specific for the $MsIn_{406-414}$ epitope. $TCR_{1045}$ binds $MsIn_{406-414}$ peptide (GQKMNAQAI, SEQ ID NO: 17) with high affinity. In particular embodiments, the Vα4 and Vβ9 genes of $TCR_{1045}$ have been codon optimized and linked by a porcine teschovirus-1 2A element.

In particular embodiments, TCR can include: α chain: MQKEVEQNSGPLSVPEGAIASLNCTYSDRGSQSFFWYRQYSGKSPELIMFIYSNGDKEDGRFTAQLNKASQYISLLIRDSKLSKATYLCAVRTNSGYALNFGKGTSLLVTPHIQKPDPAVYQLRDSKSSDK SVCLFTDFDSQTNVSQSKDSDVYITDKCVLDMRS MDFKSNSAVAWSNKSDFACANAFNNSIIPED TFFPSPESS (SEQ ID NO: 18); and β chain: MEAGVTQSPTHLIKTRGQQVTLRCSPKSGHDTVSWYQQALGQGPQFIFQYYEEEERQRGNFPDR FSGHQFPNYSSELNVNALLLGDSALYLCASSDTVSYEQYFGPGTR TVTEDLKNVFPPEVAVFEPS EAEISHTQKATLVCLATGFYPDHVELSWWVNGKEVHSGVCTDPQPLKEQPALNDSRYALSSRLRV SATFWQDPRNHFRCQVQFYGLSENDEWTQDRAKPVTQIVSAEAWGRAD (SEQ ID NO: 19). This α and β chain combination binds the HIV Gag peptide SL9 (SLYN- TVATL (SEQ ID NO: 20)) and confers anti-HIV activity to CD8+ T cells (see, e.g., Varela-Rohena, et al. 2008. Nature Medicine. 14(12): 1390-1395).

In particular embodiments, TCR can include: α chain: METLLGLLILWLQLQWVSSKQEVTQIPAALSVPE-GENLVLNCSFTDSAIYNLQWFRQDPGK GLT-SLLLIQSSQREQTSGRLNASLDKSSGRST-LYIAASQPGDSATYLCAVRRNDMRFGAGTRLTVK PNIQNP (SEQ ID NO: 21); and β chain: MGIRLLCRVAFCFLAVGLVDVKVTQSSRYLVKRT-GEKVFLECVQDMDHENMFWYRQDPGLGLRLI YFSYDVKMKEKGDIPEGYSVSREKKERFSLILESAS-TNQTSMYLCASSPGALDTDTQYFGPGTRLT VVEDIKNVFPP (SEQ ID NO: 22). This α and β chain combination binds EBV antigen (see, e.g., Kobayashi, et al. 2013. Nature Medicine 19: 1542-1546).

In particular embodiments, TCR can include: α chain: MTSIRAVFIFLWLQLDLVNGENVEQHPSTLSVQEGD-SAVIKCTYSDSASNYFPWYKQELGKRPQLII DIRSNVGEKKDQRIAVTLNKTAKHFSLHITETQPED-SAVYFCAATEDYQLIWGAGTKLIIKPDIQNPD PAVYQLRD-SKSSDKSVCLFTDFDSQTNVSQSKDSDVYITDKTVL DMRSMDFKSNSAVAWSNKSD FACANAFNN-SIIPEDTFFPSPESSCDVKLVEKS-FETDTNLNFQNLSVIGFRILLLKVAGFNLLMTLRL WSS (SEQ ID NO: 23); and β chain: MSNQVLCCVVLCFLGANTVDGGITQSPKYL-FRKEGQNVTLSCEQNLNHDAMYWYRQDPG QGLRLIYYSQIVNDFQKGDIAEGYSVS-REKKESFPLTVTSAQKNPTAFYLCASSPGALY-EQYFGPG TRLTVTEDLKNVFPPEVAVFEPSE-AEISHTQKATLVCLATGFYPDHVELSWWVNGKEVH SGVSTD PQPLKEQPALNDSRYCLSSRLRVSATFWQN-PRNHFRCQVQFYGLSENDEWTQDRAKPVTQIVSA EAWGRADCGFTSESYQQGVLSATILYEILLGKAT-LYAVLVSALVLMAMVKRKDSRG (SEQ ID NO: 24). In particular embodiments, TCR can include: α chain: MTSIRAVFIFLWLQLDLVNGENVEQHPSTLSVQEGD-SAVIKCTYSDSASNYFPWYKQELGKRPQLII DIRSNVGEKKDQRIAVTLNKTAKHFSLHITETQPED-SAVYFCAATEDYQLIWGAGTKLIIKPDIQNPD PAVYQLRD-SKSSDKSVCLFTDFDSQTNVSQSKDSDVYITDKCVL DMRSMDFKSNSAVAWSNKSD FACANAFNN-SIIPEDTFFPSPESSCDVKLVEKS-FETDTNLNFQNLSVIGFRILLLKVAGFNLLMTLRL WSS (SEQ ID NO: 25); and β chain: MSNQVLCCVVLCFLGANTVDGGITQSPKYLFRKEG-QNVTLSCEQNLNHDAMYWYRQDPGQGLR LIYYSQIVNDFQKGDIAEGYSVSREKKESFPLTVT-SAQKNPTAFYLCASSPGALYEQYFGPGTRLTV TEDLKNVFPPEVAVFEPSE-AEISHTQKATLVCLATGFYPDHVELSVWVNGKEV-HSGVCTDPQPLK EQPALN DSRY-CLSSRLRVSATFWQN PRN H FRCQVQFYGLSEN DEWTQDRAKPVTQIVSAEAWG RADCGFTS-ESYQQGVLSATILYEILLGKATLYAVLVSALVL-MAMVKRKDSRG (SEQ ID NO: 26). These α and β chain combinations bind a human Wilms tumor protein 1 (WT-1) antigen (see, e.g., US2016/0083449). WT1 is an intracellular protein that is overexpressed in a number of cancers, including acute myeloid leukemia and non-small cell lung, breast, pancreatic, ovarian, and colorectal cancers. T cells engineered with a TCR that binds a WT-1 epitope are being tested in a clinical trial for patients with high risk or relapsed acute myeloid leukemia, myelodysplastic syndrome, or chronic myelogenous leukemia, previously treated with donor stem cell transplant (Trial Number NCT01640301).

In particular embodiments, TCR can include: α chain: MACPGFLWALVISTCLEFSMAQTVTQSQPEMSVQE-AETVTLSCTYDTSESDYYLFWYKQPPSRQ MIL-VIRQEAYKQQNATENRFSVNFQKAAKSFSLKIS-DSQLGDAAMYFCALRSSGTYKYIFGTGTRL KVLANIQNPDPAVYQLRD-SKSSDKSVCLFTDFDSQTNVSQSKDSDVYITDKTVL DMRSMDFKSNS AVAWSNKSDFACANAFNN-SIIPEDTFFPSPESSCDVKLVEKS-FETDTNLNFQNLSVIGFRILLLKVA GFNLL-MTLRLWSS (SEQ ID NO: 27); and β chain: MGTRLLFWVAFCLLGADHT-GAGVSQSPSNKVTEKGKDVELRCDPIS-GHTALYWYRQSLGQGLEF LIYFQGNSAPDKSGLPS-DRFSAERTGGSVSTLTIQRTQQEDSAVYLCASIRTGP FFSGNTIYFGEG SWLTVVEDLNKVFPPEVAVFEPSE-AEISHTQKATLVCLATGFFPDHVELSWWVNGKEV-HSGVSTD PQPLKEQPALNDSRY-CLSSRLRVSATFWQNPRNHFRCQVQFYGLSENDEW TQDRAKPVTQIVSA EAWGRADCGFTSVSYQQGVL-SATILYEILLGKATLYAVLVSALVLMAMVKRKDF (SEQ ID NO: 28).

In particular embodiments, TCR can include: α chain: MACPGFLWALVISTCLEFSMAQTVTQSQPEMSVQE-AETVTLSCTYDTSESDYYLFWYKQPPSRQ MIL-VIRQEAYKQQNATENRFSVNFQKAAKSFSLKIS-DSQLGDAAMYFCALRASGTYKYIFGTGTRL KVLANIQNPDPAVYQLRD-SKSSDKSVCLFTDFDSQTNVSQSKDSDVYITDKTVL DMRSMDFKSNS AVAWSNKSDFACANAFNN-SIIPEDTFFPSPESSCDVKLVEKS-FETDTNLNFQNLSVIGFRILLLKVA GFNLL-MTLRLWSS (SEQ ID NO: 29); and β chain: MGTRLLFWVAFCLLGADHT-GAGVSQSPSNKVTEKGKDVELRCDPIS-GHTALYWYRQSLGQGLEF LIYFQGNSAPDKSGLPS-DRFSAERTGGSVSTLTIQRTQQEDSAVYLCASIRTGP FFSGNTIYFGEG SWLTVVEDLNKVFPPEVAVFEPSE-AEISHTQKATLVCLATGFFPDHVELSWWVNGKEV-HSGVSTD PQPLKEQPALNDSRY-CLSSRLRVSATFWQNPRNHFRCQVQFYGLSENDEW TQDRAKPVTQIVSA EAWGRADCGFTSVSYQQGVL-SATILYEILLGKATLYAVLVSALVLMAMVKRKDF (SEQ ID NO: 28).

In particular embodiments, TCR can include: α chain: MACPGFLWALVISTCLEFSMAQTVTQSQPEMSVQE-AETVTLSCTYDTSESDYYLFWYKQPPSRQ MIL-VIRQEAYKQQNATENRFSVNFQKAAKSFSLKIS-DSQLGDAAMYFCALRSAGTYKYIFGTGTRL KVLANIQNPDPAVYQLRD-SKSSDKSVCLFTDFDSQTNVSQSKDSDVYITDKTVL DMRSMDFKSNS AVAWSNKSDFACANAFNN-SIIPEDTFFPSPESSCDVKLVEKS-FETDTNLNFQNLSVIGFRILLLKVA GFNLL-MTLRLWSS (SEQ ID NO: 30); and β chain: MGTRLLFWVAFCLLGADHT-GAGVSQSPSNKVTEKGKDVELRCDPIS-GHTALYWYRQSLGQGLEF LIYFQGNSAPDKSGLPS-DRFSAERTGGSVSTLTIQRTQQEDSAVYLCASIRTGPFF-SGNTIYFGEG SWLTVVEDLNKVFPPEVAVFEPSE-AEISHTQKATLVCLATGFFPDHVELSWWVNGKEV-HSGVSTD PQPLKEQPALNDSRY-CLSSRLRVSATFWQNPRNHFRCQVQFYGLSENDEW TQDRAKPVTQIVSA EAWGRADCGFTSVSYQQGVL-
SATILYEILLGKATLYAVLVSALVLMAMVKRKDF
(SEQ ID NO: 28).

In particular embodiments, TCR can include: α chain:
MACPGFLWALVISTCLEFSMAQTVTQSQPEMSVQE-
AETVTLSCTYDTSESDYYLFWYKQPPSRQ MIL-
VIRQEAYKQQNATENRFSVNFQKAAKSFSLKIS-
DSQLGDAAMYFCALRVSGTYKYIFGTGTRL
KVLANIQNPDPAVYQLRD-
SKSSDKSVCLFTDFDSQTNVSQSKDSDVYITDKTVL
DMRSMDFKSNS AVAWSNKSDFACANAFNN-
SIIPEDTFFPSPESSCDVKLVEKS-
FETDTNLNFQNLSVIGFRILLLKVA GFNLL-
MTLRLWSS (SEQ ID NO: β1); and β chain:
MGTRLLFWVAFCLLGADHT-
GAGVSQSPSNKVTEKGKDVELRCDPIS-
GHTALYWYRQSLGQGLEF LIYFQGNSAPDKSGLPS-
DRFSAERTGGSVSTLTIQRTQQEDSAVYLCASIRTGP
FFSGNTIYFGEG SWLTVVEDLNKVFPPEVAVFEPSE-
AEISHTQKATLVCLATGFFPDHVELSWWVNGKEV-
HSGVSTD PQPLKEQPALNDSRY-
CLSSRLRVSATFWQNPRNHFRCQVQFYGLSENDEW
TQDRAKPVTQIVSA EAWGRADCGFTSVSYQQGVL-
SATILYEILLGKATLYAVLVSALVLMAMVKRKDF
(SEQ ID NO: 28).

In particular embodiments, TCR can include: α chain:
MACPGFLWALVISTCLEFSMAQTVTQSQPEMSVQE-
AETVTLSCTYDTSESDYYLFWYKQPPSRQ MIL-
VIRQEAYKQQNATENRFSVNFQKAAKSFSLKIS-
DSQLGDAAMYFCALRSSGTYKYIFGTGTRL
KVLANIQNPEPAVYQLKDPRSQDSTLCLFTDFDSQ-
INVPKTMESGTFITDKTVLDMKAMDSKSNGA
IAWSNQTSFTCQDIFKETNATYPSSDVPCDATLTEKS-
FETDMNLNFQNLSVMGLRILLLKVAGFNLL
MTLRLWSS (SEQ ID NO: β2); and β chain:
MGTRLLFWVAFCLLGADHT-
GAGVSQSPSNKVTEKGKDVELRCDPIS-
GHTALYWYRQSLGQGLEF LIYFQGNSAPDKSGLPS-
DRFSAERTGGSVSTLTIQRTQQEDSAVYLCASIRTGP
FFSGNTIYFGEG SWLTVVEDLRNVTPPKVSLFEPS-
KAEIANKQKATLVCLARGFFPDHVELSWWVNGKEV-
HSGVSTD PQAYKESNYSYCLSSRLRVSATFWHN-
PRNHFRCQVQFHGLSEEDKWPEGSPKPVTQNISAE
AW GRADCGITSASYHQGVLSATILYEILLGKAT-
LYAVLVSGLVLMAMVKRKNS (SEQ ID NO: 33). These α and β chain combinations bind MAGE A3/MAGE A6 antigens (see, e.g., US2015/0246959). MAGE A proteins are testis-specific E3 ubiquitin ligase components whose expression is upregulated in many cancers. MAGE A3 and A6 are frequently overexpressed in common solid tumors including bladder, esophageal, head and neck, lung and ovarian cancers. T cells engineered with a TCR that binds a MAGE A3/MAGE A6 antigen are being tested in a clinical trial for patients who are HLA-DPB1*04:01 positive and whose tumors are MAGE-A3 and/or MAGE-A6 positive (Trial Number NCT03139370).

In particular embodiments, TCR can include: α chain:
MQEVTQIPAALSVPEGENLVLNCSFTD-
SAIYNLQWFRQDPGKGLTSLLLIQSSQREQTSGRL-
NASL DKSSGRSTLYIAASQPGDSATYL-
CAVRPLYGGSYIPTFGRGTSLIVHPYIQNPDPAVYQL
RDSKSS
DKSVCLFTDFDSQTNVSQSKDSDVYITDKTVLDMR
SMDFKSNSAVAWSNKSDFACANAFNNSIIP
EDTFFPSPESS (SEQ ID NO: 34); and β chain:
MGVTQTPKFQVLKTGQSMTLQCAQDMN-
HEYMSWYRQDPGMGLRLIHYSVGAGITDQ-
GEVPNGY NVSRSTTEDFPLRLLSAAP-
SQTSVYFCASSYVGNTGELFFGEGSRLTVLEDLKNV
FPPEVAVFEPS EAEISHTQKATLVCLATGFYPDHV-
ELSWWVNGKEVHSGVSTDPQPLKEQPALNDSRY-
ALSSRLRV SATFWQDPRNHFRCQVQFYGLSEND-
EWTQDRAKPVTQIVSAEAWGRAD (SEQ ID NO: 35).

In particular embodiments, TCR can include: α chain:
MQEVTQIPAALSVPEGENLVLNCSFTD-
SAIYNLQWFRQDPGKGLTSLLLIQSSQREQTSGRL-
NASL DKSSGRSTLYIAASQPGDSATYL-
CAVRPLYGGSYIPTFGRGTSLIVHPYIQNPDPAVYQL
RDSKSS
DKSVCLFTDFDSQTNVSQSKDSDVYITDKCVLDMR
SMDFKSNSAVAWSNKSDFACANAFNNSIIP
EDTFFPSPESS (SEQ ID NO: 36); and β chain:
MGVTQTPKFQVLKTGQSMTLQCAQDMN-
HEYMSWYRQDPGMGLRLIHYSVGAGITDQ-
GEVPNGY NVSRSTTEDFPLRLLSAAP-
SQTSVYFCASSYVGNTGELFFGEGSRLTVLEDLKNV
FPPEVAVFEPS EAEISHTQKATLVCLATGFYPDHV-
ELSWWVNGKEVHSGVCTDPQPLKEQPALNDSRY-
ALSSRLRV SATFWQDPRNHFRCQVQFYGLSEND-
EWTQDRAKPVTQIVSAEAWGRAD (SEQ ID NO: 37). These α and β chain combinations bind the SLLMWITQC (SEQ ID NO: 38)-HLA-A*0201 complex. The SLL-MWITQC (SEQ ID NO: 38) peptide is derived from a human tumor antigen NY-ESO-1 of the cancer/testis family. NY-ESO-1 is being studied as a possible target for a cancer vaccine or immunotherapy. It is highly expressed in many poor-prognosis melanomas. T cells engineered with a TCR that binds the SLLMWITQC (SEQ ID NO: 38)-HLA-A*0201 complex are being tested in a clinical trial for patients with ovarian cancer (Trial Number NCT01567891). Robbins P F et al. (2008) The Journal of Immunology 180(9): 6116-6131 and U.S. Pat. No. 8,008,438 disclose TCR α and β chain sequences that bind the SLLMWITQC (SEQ ID NO: 38)-HLA-A*0201 complex.

In particular embodiments, TCR can include an engineered TCR such as that described in WO2011039507. Such TCR include an α chain and a β chain separated by an internal self-cleaving porcine teschovirus 2A sequence and binds a human herpesvirus-5, or cytomegalovirus (CMV) antigen. One example includes the anti-CMV artificial TCR:
MEKNPLAAPLLILWFHLDCVSILN-
VEQSPQSLHVQEGDSTNFTCSFPSSNFYALHWYR-
WETAKSP EALFVMTLNGDEKKKG (SEQ ID NO: 39).

II. Polynucleotides (PN) Encoding TCR. PN describes a nucleic acid molecule including a nucleic acid sequence encoding a TCR that binds an antigen/MHC complex such that upon introduction into a T cell, the PN causes expression of the encoded TCR. Administered PN can include a gene. The term "gene" refers to a nucleic acid sequence that encodes a TCR for use in a system or method described herein. The definition of "gene" includes various sequence polymorphisms, mutations, and/or sequence variants wherein such alterations do not significantly affect the function of the encoded TCR. The term "gene" may include not only coding sequences but also regulatory regions such as promoters, enhancers, and termination regions. The term further can include all introns and other DNA sequences spliced from the mRNA transcript, along with variants resulting from alternative splice sites. Nucleic acid sequences encoding the TCR can be DNA or RNA that direct the expression of the TCR. These nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein. The sequences can also include degenerate codons of the native sequence or sequences that may be introduced to provide codon preference in a specific T cell. Many gene sequences to encode TCR are available in publicly available databases and publications. Those of ordinary skill in the art can also derive such gene sequences based on identification of a TCR of interest.

"Encoding" refers to a property of sequences of nucleotides in a PN, such as a plasmid, a gene, cDNA, or mRNA, to serve as a template for synthesis of a TCR. A PN can, e.g., encode a protein if transcription and translation of mRNA produced by a gene produces the protein in a cell or other biological system.

In particular embodiments, the PN includes a plasmid, a cDNA, or an mRNA that includes a gene for expressing a TCR. Suitable plasmids include standard plasmid vectors and minicircle plasmids that can be used to transfer a gene to a T cell. The PN (e.g., minicircle plasmids) can further include any additional sequence information to facilitate transfer of the genetic material (e.g., a sequence encoding a TCR specific for an antigen) to T cells. For example, the PN can include promoters, such as general promoters, tissue-specific promoters, cell-specific promoters, and/or promoters specific for the nucleus or cytoplasm. Promoters and plasmids (e.g., minicircle plasmids) are generally well known in the art and can be prepared using conventional techniques.

As described further herein, the PN can be used to transfect T cells. Unless otherwise specified, the terms transfect, transfected, or transfecting can be used to indicate the presence of exogenous PN or the expressed polypeptide therefrom in a T cell. A number of vectors are known to be capable of mediating transfer of PN to lymphocytes, as is known in the art.

In particular embodiments, the transfected PN can edit the antigen-specificity of T cells without affecting off-target bystander cells (i.e., provide for selective delivery as defined herein). For example, delivered genes can be expressed under the control of a T cell-specific promoter. In particular embodiments, such promoters can be included in minicircle plasmids that are a form of supercoiled DNA molecule for nonviral gene transfer, which have neither bacterial origin of replication nor antibiotic resistance marker. They are thus smaller and potentially safer than the standard plasmids currently used in gene therapy.

To sustain the expression of transferred TCR genes, for example, in rapidly dividing T cells, a scaffold/matrix attachment region can also be inserted into the PN. PN including an expression cassette linked to a S/MAR element, can autonomously replicate extra-chromosomally in dividing cells. In particular embodiments, PiggyBac or Sleeping Beauty transposase-containing plasmids can also be used to stably integrate TCR genes into the genome of transfected cells. Other options to sustain expression include *Homo sapiens* transposon-derived Buster1 transposase-like protein gene; human endogenous retrovirus H protease/integrase-derived ORF1; *Homo sapiens* Cas-Br-M (murine) ecotropic retroviral transforming sequence; *Homo sapiens* endogenous retroviral sequence K; *Homo sapiens* endogenous retroviral family W; *Homo sapiens* LINE-1 type transposase domain; and *Homo sapiens* pogo transposable element. Particular embodiments can utilize the hyperactive iPB7 transposase.

When a delivered PN is mRNA, backbone modifications can increase the mRNA's stability making resistant to premature cleavage.

In particular embodiments, self-replicating mRNA constructs can be used to ensure persistent transgene expression without the requirement of host genome integration. Self-replicating RNA can refer to RNA molecules that encode RNA replication machinery, so that upon translation, cis-encoded genes can produce new RNA copies from the original template molecule. Self-replicating RNAs can be designed using sequences derived from RNA viruses, such as alphaviruses and pestiviruses. Techniques for designing and using self-replicating RNA molecules for delivery of mRNA can be found in, for example, WO/2011/005799, WO/2009/146867, and Geall, A, et al. 2012. Proc Natl Acad Sci USA. 109(36):14604-14609.

In particular embodiments, PN include synthetic mRNA. In particular embodiments, synthetic mRNA is engineered for increased intracellular stability using 5'-capping. Multiple distinct 5'-cap structures can be used to generate the 5'-cap of a synthetic mRNA molecule. For example, the Anti-Reverse Cap Analog (ARCA) cap contains a 5'-5'-triphosphate guanine-guanine linkage where one guanine contains an N7 methyl group as well as a 3'-O-methyl group. Synthetic mRNA molecules may also be capped post-transcriptionally using enzymes responsible for generating 5'-cap structures. For example, recombinant Vaccinia Virus Capping Enzyme and recombinant 2'-O-methyltransferase enzyme can create a canonical 5'-5'-triphosphate linkage between the 5'-most nucleotide of an mRNA and a guanine nucleotide where the guanine contains an N7 methylation and the ultimate 5'-nucleotide contains a 2'-O-methyl generating the Cap1 structure. This results in a cap with higher translational-competency and cellular stability and reduced activation of cellular pro-inflammatory cytokines.

Synthetic mRNA or other PN may also be made cyclic. PN may be cyclized, or concatemerized, to generate a translation competent molecule to assist interactions between poly-A binding proteins and 5'-end binding proteins. The mechanism of cyclization or concatemerization may occur through at least 3 different routes: 1) chemical, 2) enzymatic, and 3) ribozyme catalyzed. The newly formed 5'-/3'-linkage may be intramolecular or intermolecular.

In the first route, the 5'-end and the 3'-end of the PN may contain chemically reactive groups that, when close together, form a new covalent linkage between the 5'-end and the 3'-end of the molecule. The 5'-end may contain an NHS-ester reactive group and the 3'-end may contain a 3'-amino-terminated nucleotide such that in an organic solvent the 3'-amino-terminated nucleotide on the 3'-end of a synthetic PN molecule will undergo a nucleophilic attack on the 5'-NHS-ester moiety forming a new 5'-/3'-amide bond.

In the second route, T4 RNA ligase may be used to enzymatically link a 5'-phosphorylated PN to the 3'-hydroxyl group of a nucleic acid forming a new phosphorodiester linkage. In an example reaction, 1 µg of a nucleic acid molecule can be incubated at 37° C. for 1 hour with 1-10 units of T4 RNA ligase (New England Biolabs, Ipswich, Mass.) according to the manufacturer's protocol. The ligation reaction may occur in the presence of a split oligonucleotide capable of base-pairing with both the 5'- and 3'-region in juxtaposition to assist the enzymatic ligation reaction.

In the third route, either the 5'- or 3'-end of a cDNA template encodes a ligase ribozyme sequence such that during in vitro transcription, the resultant nucleic acid molecule can contain an active ribozyme sequence capable of ligating the 5'-end of a nucleic acid molecule to the 3'-end of a nucleic acid molecule. The ligase ribozyme may be derived from the Group I Intron, Group I Intron, Hepatitis Delta Virus, Hairpin ribozyme or may be selected by SELEX (systematic evolution of ligands by exponential enrichment). The ribozyme ligase reaction may take 1 to 24 hours at temperatures between 0 and 37° C.

In particular embodiments, the PN encodes TCR α and β chains that specifically bind an antigen/MHC complex of interest, that is the PN encodes the TCR α and β chain variable regions. In particular embodiments, the PN can additionally encode a TCR constant domain, a transmembrane domain and/or a cytoplasmic tail. Sequences and structures of these portions of TCR are known to those of skill in the art and can be readily accessed in public databases. As one example, SEQ ID NO: 40 provides a representative gene sequence encoding the CD4 transmembrane domain (see FIG. 5). In particular embodiments, the PN can encode an invariant CD3 chain (i.e., γ, Δ, Σ, Z, H), and/or an ITAM motif (derived from, e.g., CD3-Z, FeR-γ, CD3-γ, CD3-Δ, CD3-Σ, CD5, CD22, CD79a, CD79b, and/or CD66d).

In particular embodiments, PN can include a sequence encoding a spacer region. The length of the spacer region can be customized for individual antigen/MHC complexes to optimize target recognition, binding, and T cell activation. In particular embodiments, a spacer length can be selected based upon the location of an antigen/MHC complex epitope, affinity of a TCR for the epitope, and/or the ability of the T cells expressing the TCR to proliferate in vitro and/or in vivo in response to antigen/MHC complex recognition.

Typically a spacer region is found between the α and β chains of a TCR and a transmembrane domain of the TCR. Spacer regions can provide for flexibility of the α and β chains and allows for high expression levels in genetically modified T cells. In particular embodiments, a spacer region can have at least 10 to 250 amino acids, at least 10 to 200 amino acids, at least 10 to 150 amino acids, at least 10 to 100 amino acids, at least 10 to 50 amino acids or at least 10 to 25 amino acids and including any integer between the endpoints of any of the listed ranges. In particular embodiments, a spacer region has 250 amino acids or less; 200 amino acids or less, 150 amino acids or less; 100 amino acids or less; 50 amino acids or less; 40 amino acids or less; 30 amino acids or less; 20 amino acids or less; or 10 amino acids or less.

In particular embodiments, spacer regions can be derived from a hinge region of an immunoglobulin like molecule, for example all or a portion of the hinge region from a human IgG1, human IgG2, a human IgG3, or a human IgG4. In particular embodiments, all or a portion of a hinge region can be combined with one or more domains of a constant region of an immunoglobulin. For example, a portion of a hinge region can be combined with all or a portion of a CH2 or CH3 domain or variant thereof.

In particular embodiments, introduction of PN to T cells can be carried out by any method known in the art, including transfection, electroporation, microinjection, lipofection, calcium phosphate mediated transfection, infection with a viral or bacteriophage vector containing the gene sequences, receptor-mediated endocytosis, cell fusion, chromosome-mediated gene transfer, microcell-mediated gene transfer, sheroplast fusion, etc. Numerous techniques are known in the art for the introduction of foreign genes into cells (see e.g., Loeffler and Behr, Meth. Enzymol. 217, 599-618 (1993); Cohen et al., Meth. Enzymol. 217, 618-644 (1993); Cline, Pharmac. Ther, 29, 69-92 (1985)) and may be used in accordance with the present disclosure, provided that the necessary developmental and physiological functions of the T cells are not disrupted. In particular embodiments, the technique provides for the stable transfer of a gene to the T cell, so that the gene is expressible by the cell and preferably heritable and expressible by its cell progeny. In particular embodiments, the technique provides for transient expression of the gene within a cell. Methods commonly known in the art of recombinant DNA technology which can be used to genetically modify T cells are described in, for example, Ausubel et al. (eds.), 1993, Current Protocols in Molecular Biology, John Wiley & Sons, NY; and Kriegler, 1990, Gene Transfer and Expression, A Laboratory Manual, Stockton Press, NY.

II. Nanoparticles (NP). In particular embodiments, PN are administered to T cells using nanoparticles (NP). Particular NP embodiments include a positively-charged carrier. Carriers function to condense and protect PN from enzymatic degradation. Particularly useful materials to use as carriers include positively charged lipids and/or polymers, including poly(β-amino ester).

Additional examples of positively charged lipids include esters of phosphatidic acid with an aminoalcohol, such as an ester of dipalmitoyl phosphatidic acid or distearoyl phosphatidic acid with hydroxyethylenediamine. More particular examples of positively charged lipids include 3β-[N-(N',N'-dimethylaminoethyl)carbamoyl] cholesterol (DC-chol); N,N'-dimethyl-N,N'-dioctacyl ammonium bromide (DDAB); N,N'-dimethyl-N,N'-dioctacyl ammonium chloride (DDAC); 1,2-dioleoyloxypropyl-3-dimethyl-hydroxyethyl ammonium chloride (DORI); 1,2-dioleoyloxy-3-[trimethylammonio]-propane (DOTAP); N-(1-(2,3-dioleyloxy)propyl)-N, N,N-trimethylammonium chloride (DOTMA); dipalmitoylphosphatidylcholine (DPPC); 1,2-dioctadecyloxy-3-[trimethylammonio]-propane (DSTAP); and the cationic lipids described in e.g. Martin et al., Current Pharmaceutical Design 2005, 11, 375-394.

Examples of positively charged polymers that can be used as carriers within the current disclosure include polyamines; polyorganic amines (e.g., polyethyleneimine (PEI), polyethyleneimine celluloses); poly(amidoamines) (PAMAM); polyamino acids (e.g., polylysine (PLL), polyarginine); polysaccharides (e.g, cellulose, dextran, DEAE dextran, starch); spermine, spermidine, poly(vinylbenzyl trialkyl ammonium), poly(4-vinyl-N-alkyl-pyridiumiun), poly(acryloyl-trialkyl ammonium), and Tat proteins.

Without limiting the foregoing, particular embodiments disclosed herein can also utilize porous NP constructed from any material capable of forming a porous network. Exemplary materials include biocompatible polymers, metals, transition metals and metalloids. Exemplary biocompatible polymers include agar, agarose, alginate, alginate/calcium phosphate cement (CPC), 3-galactosidase (β-GAL), (1,2,3, 4,6-pentaacetyl a-D-galactose), cellulose, chitin, chitosan, collagen, elastin, gelatin, hyaluronic acid collagen, hydroxyapatite, poly(3-hydroxybutyrate-co-3-hydroxy-hexanoate) (PHBHHx), poly(lactide), poly(caprolactone) (PCL), poly (lactide-co-glycolide) (PLG), poly(lactic-co-glycolic acid) (PLGA), poly(vinyl alcohol) (PVA), silk, soy protein, and soy protein isolate, alone or in combination with any other polymer composition, in any concentration and in any ratio. Blending different polymer types in different ratios using various grades can result in characteristics that borrow from each of the contributing polymers. Various terminal group chemistries can also be adopted.

In particular embodiments, NP include a coating that shields encapsulated PN and reduces or prevents off-target binding. Off-target binding is reduced or prevented by reducing the surface charge of the NP to neutral or negative.

Coatings can include neutral or negatively charged polymer- and/or liposome-based coatings. In particular embodiments, the coating is a dense surface coating of hydrophilic and/or neutrally charged hydrophilic polymer sufficient to prevent the encapsulated nucleic acids from being exposed to the environment before release into a selected cell. In particular embodiments, the coating covers at least 80% or at least 90% of the surface of the NP. In particular embodiments, the coating includes polyglutamic acid (PGA).

Examples of additional neutrally charged polymers that can be used as coatings include polyethylene glycol (PEG); poly(propylene glycol); and polyalkylene oxide copolymers, (PLURONIC®, BASF Corp., Mount Olive, N.J.).

Neutrally charged polymers also include zwitterionic polymers. Zwitterionic refers to the property of overall charge neutrality while having both a positive and a negative electrical charge.

Zwitterionic polymers can behave like regions of cell membranes that resist cell and protein adhesion.

Zwitterionic polymers include zwitterionic constitutional units including pendant groups (i.e., groups pendant from the polymer backbone) with zwitterionic groups. Exemplary zwitterionic pendant groups include carboxybetaine groups (e.g., -Ra-N+(Rb)(Rc)-Rd-CO2-, where Ra is a linker group that covalently couples the polymer backbone to the cationic nitrogen center of the carboxybetaine groups, Rb and Rc are nitrogen substituents, and Rd is a linker group that covalently couples the cationic nitrogen center to the carboxy group of the carboxybetaine group).

Examples of negatively charged polymers include alginic acids; carboxylic acid polysaccharides; carboxymethyl cellulose; carboxymethyl cellulose-cysteine; carrageenan (e.g., Gelcarin® 209, Gelcarin® 379); chondroitin sulfate; glycosaminoglycans; mucopolysaccharides; negatively charged polysaccharides (e.g., dextran sulfate); poly(acrylic acid); poly(D-aspartic acid); poly(L-aspartic acid); poly(L-aspartic acid) sodium salt; poly(D-glutamic acid); poly(L-glutamic acid); poly(L-glutamic acid) sodium salt; poly(methacrylic acid); sodium alginate (e.g., Protanal® LF 120M, Protanal® LF 200M, Protanal® LF 200D); sodium carboxymethyl cellulose (CMC); sulfated polysaccharides (heparins, agaropectins); pectin, gelatin and hyaluronic acid.

In particular embodiments, polymers disclosed herein can include "star shaped polymers," which refer to branched polymers in which two or more polymer branches extend from a core. The core is a group of atoms having two or more functional groups from which the branches can be extended by polymerization.

In particular embodiments, the branches are zwitterionic or negatively-charged polymeric branches. For star polymers, the branch precursors can be converted to zwitterionic or negatively-charged polymers via hydrolysis, ultraviolet irradiation, or heat. The polymers also may be obtained by any polymerization method effective for polymerization of unsaturated monomers, including atom transfer radical polymerization (ATRP), reversible addition-fragmentation chain transfer polymerization (RAFT), photo-polymerization, ring-opening polymerization (ROP), condensation, Michael addition, branch generation/propagation reaction, or other reactions.

Liposomes are microscopic vesicles including at least one concentric lipid bilayer. Vesicle-forming lipids are selected to achieve a specified degree of fluidity or rigidity of the final complex. In particular embodiments, liposomes provide a lipid composition that is an outer layer surrounding a particle.

Liposomes can be neutral (cholesterol) or bipolar and include phospholipids, such as phosphatidylcholine (PC), phosphatidylethanolamine (PE), phosphatidylinositol (PI), and sphingomyelin (SM) and other type of bipolar lipids including dioleoylphosphatidylethanolamine (DOPE), with a hydrocarbon chain length in the range of 14-22, and saturated or with one or more double C=C bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanolamine, phosphatidylserine, phosphatidylinositol, sphingomyelin, cephalin, cardiolipin, phosphatidic acid, cerebro sides, distearoylphosphatidylethanolamine (DSPE), dioleoylphosphatidylcholine (DOPC), dipalmitoylphosphatidylcholine (DPPC), palmitoyloleoylphosphatidylcholine (POPC), palmitoyloleoylphosphatidylethanolamine (POPE) and dioleoylphosphatidylethanolamine 4-(N-maleimido-methyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, DDAB, dioctadecyl dimethyl ammonium chloride (DODAC), 1,2-dimyristoyl-3-trimethylammonium propane (DMTAP), DOTAP, DOTMA, DC-Chol, phosphatidic acid (PA), dipalmitoylphosphatidylglycerol (DPPG), dioleoylphosphatidylglycerol, DOPG, and dicetylphosphate. In particular embodiments, lipids used to create liposomes disclosed herein include cholesterol, hydrogenated soy phosphatidylcholine (HSPC) and, the derivatized vesicle-forming lipid PEG-DSPE.

Methods of forming liposomes are described in, for example, U.S. Pat. Nos. 4,229,360; 4,224,179; 4,241,046; 4,737,323; 4,078,052; 4,235,871; 4,501,728; and 4,837,028, as well as in Szoka et al., Ann. Rev. Biophys. Bioeng. 9:467 (1980) and Hope et al., Chem. Phys. Lip. 40:89 (1986).

The NP can be a variety of different shapes, including spheroidal, cuboidal, pyramidal, oblong, cylindrical, toroidal, and the like. The PN can be included in the NP in a variety of ways. For example, the PN can be encapsulated in the NP. In other aspects, the PN can be associated (e.g., covalently and/or non-covalently) with the surface or close underlying vicinity of the surface of the NP. In particular embodiments, the PN can be incorporated in the NP e.g., integrated in the material of the NP. For example, the PN can be incorporated into a polymer matrix of polymer NP. One of ordinary skill in the art will appreciate the various ways to carry the PN so as to allow delivery of the PN to cells.

The size of the NP can vary over a wide range and can be measured in different ways. For example, the NP can have a minimum dimension of 100 nm. The NP can also have a minimum dimension of equal to or less than 500 nm, less than 150 nm, less than 100 nm, less than 90 nm, less than 80 nm, less than 70 nm, less than 60 nm, less than 50 nm, less than 40 nm, less than 30 nm, less than 20 nm, or less than 10 nm. In particular embodiments, the NP can have a minimum dimension ranging between 5 nm and 500 nm, between 10 nm and 100 nm, between 20 nm and 90 nm, between 30 nm and 80 nm, between 40 nm and 70 nm, and between 40 nm and 60 nm. In particular embodiments, the dimension is the diameter of NP or coated NP. In particular embodiments, a population of NP can have a mean minimum dimension of equal to or less than 500 nm, less than 100 nm, less than 90 nm, less than 80 nm, less than 70 nm, less than 60 nm, less than 50 nm, less than 40 nm, less than 30 nm, less than 20 nm, or less than 10 nm. In particular embodiments, a population of NP in a composition can have a mean diameter ranging between 5 nm and 500 nm, between 10 nm and 100 nm, between 20 nm and 90 nm, between 30 nm and 80 nm, between 40 nm and 70 nm, and between 40 nm and 60 nm. Dimensions of the NP can be determined using, e.g., conventional techniques, such as dynamic lightscattering and/or electron microscopy.

IV. T Cell Targeting and Delivery Agents (T-DA). In particular embodiments, NP include T Cell Targeting and Delivery Agents (T-DA) to allow selective delivery of the PN to chosen cell types, either in vivo or ex vivo.

T-DA selectively bind T cells of interest. In particular embodiments, T-DA achieve selective delivery of NP to particular T cell populations through receptor-mediated endocytosis by targeting a marker expressed by the T cell type. For example, as previously indicated CD4+ T cells express the CD4 protein on their surface and CD8+ T cells express the CD8 protein on their surface.

"Naive" T cells as used herein refers to a non-antigen experienced T cell that expresses CD62L and CD45RA, and does not express CD45RO as compared to non-naïve T cells. In particular embodiments, naive T cells can be further characterized by the expression of phenotypic markers including CD62L, CCR7, CD28, CD127, and CD45RA. T-DA can bind CD62L, CCR7, CD28, CD127 and/or CD45RA to achieve selective delivery of a PN to naive T cells.

CD3 is expressed on all mature T cells. Accordingly, T-DA can bind CD3 to achieve selective delivery of a PN to all mature T cells. Activated T cells express 4-1BB (CD137). Accordingly, T-DA can bind 4-1 BB to achieve selective delivery of a PN to activated T cells. CD5 and transferrin receptor are also expressed on T cells and can be used to achieve selective delivery of a PN to T cells.

"Central memory" T cells (or "TCM") as used herein refers to an antigen experienced CTL that expresses CD62L or CCR7 and CD45RO on the surface thereof, and does not express or has decreased expression of CD45RA as compared to naive cells. In particular embodiments, central memory cells are positive for expression of CD62L, CCR7, CD25, CD127, CD45RO, and CD95, and have decreased expression of CD45RA as compared to naive cells. T-DA can bind CD62L, CCR7, CD25, CD127, CD45RO and/or CD95 to achieve selective delivery of a polynucleotide to TCM.

"Effector memory" T cell (or "TEM") as used herein refers to an antigen experienced T cell that does not express or has decreased expression of CD62L on the surface thereof as compared to central memory cells, and does not express or has decreased expression of CD45RA as compared to a naive cell. In particular embodiments, effector memory cells are negative for expression of CD62L and CCR7, compared to naive cells or central memory cells, and have variable expression of CD28 and CD45RA. Effector T cells are positive for granzyme B and perforin as compared to memory or naive T cells. T-DA can bind granzyme B and/or perform to achieve selective delivery of a PN to TEM.

Lymphocyte function-associated antigen 1 (LFA-1) is expressed by all T cells, B cells and monocytes/macrophages. Accordingly, T-DA can bind LFA-1 to achieve selective delivery of a PN to T cells, B cells and monocytes/macrophages.

"Selective delivery" means that PN are delivered and expressed by one or more selected cell populations. In particular embodiments, selective delivery is exclusive to a selected T cell population. In particular embodiments, at least 65%, 70%, 75%, 80%, 85%, 90%, 95% or 99% of administered PN are delivered and/or expressed by a T cell population. In particular embodiments, selective delivery ensures that non-selected cells do not express delivered PN. For example, when the PN encodes a TCR, selectivity can be ensured because only T cells have the Z chains required for TCR expression. Selective delivery can also be based on lack of PN uptake into unselected cells or based on the presence of a specific promoter within the PN sequence when the PN includes plasmid DNA. For example, plasmid DNA can include a T cell-specific promoter, such as the distal lck promoter for T cells. In particular embodiments, selective delivery is observed due to the selective binding of T-DA to targeted T cells.

As indicated, T-DA can include binding domains for motifs found on T cells. T-DA can also include any selective binding mechanism allowing selective uptake into selected T cells. In particular embodiments, T-DA include binding domains for T cell receptor motifs; T cell α chains; T cell 3 chains; CCR7; CD3; CD4; CD8; CD28; CD45RA; CD62L; CD127; LFA-1; and combinations thereof.

In particular embodiments, binding domains include cell marker ligands, receptor ligands, antibodies, peptides, peptide aptamers, nucleic acids, nucleic acid aptamers, spiegelmers or combinations thereof. Within the context of T-DA, binding domains include any substance that binds to another substance to form a complex capable of mediating endocytosis.

"Antibodies" are one example of binding domains and include whole antibodies or binding fragments of an antibody, e.g., Fv, Fab, Fab', F(ab')2, Fc, and single chain Fv fragments (scFvs) or any biologically effective fragments of an immunoglobulin that bind specifically to a motif expressed by a selected cell. Antibodies or antigen binding fragments include all or a portion of polyclonal antibodies, monoclonal antibodies, human antibodies, humanized antibodies, synthetic antibodies, chimeric antibodies, bispecific antibodies, mini bodies, and linear antibodies.

Antibodies from human origin or humanized antibodies have lowered or no immunogenicity in humans and have a lower number of non-immunogenic epitopes compared to non-human antibodies. Antibodies and their fragments will generally be selected to have a reduced level or no antigenicity in human subjects.

Antibodies that specifically bind a motif expressed by a T cell can be prepared using methods of obtaining monoclonal antibodies, methods of phage display, methods to generate human or humanized antibodies, or methods using a transgenic animal or plant engineered to produce antibodies as is known to those of ordinary skill in the art (see, for example, U.S. Pat. Nos. 6,291,161 and 6,291,158). Phage display libraries of partially or fully synthetic antibodies are available and can be screened for an antibody or fragment thereof that can bind to a T cell motif. For example, binding domains may be identified by screening a Fab phage library for Fab fragments that specifically bind to a target of interest (see Hoet et al., Nat. Biotechnol. 23:344, 2005). Phage display libraries of human antibodies are also available. Additionally, traditional strategies for hybridoma development using a target of interest as an immunogen in convenient systems (e.g., mice, HuMAb Mouse®, TC Mouse™, KM-Mouse®, llamas, chicken, rats, hamsters, rabbits, etc.) can be used to develop binding domains. In particular embodiments, antibodies specifically bind to motifs expressed by a selected T cell and do not cross react with nonspecific components or unrelated targets. Once identified, the amino acid sequence or polynucleotide sequence coding for the antibody can be isolated and/or determined.

In particular embodiments, binding domains of selected T-DA include T cell receptor motif antibodies; T cell α chain antibodies; T cell β chain antibodies; CCR7 antibodies; CD3 antibodies; CD4 antibodies; CD8 antibodies; CD28 antibodies; CD45RA antibodies; CD62L antibodies; CD127 antibodies; and/or LFA-1 antibodies. These binding domains also can consist of scFv fragments of the foregoing antibodies.

In particular embodiments, the T-DA includes an antibody or antibody fragment that binds to CD4. An example of an antibody that binds to CD4 is TNX-355, which is described in U.S. Publication No. US20130195881. The TNX-355 anti-CD4 antibody includes a variable heavy chain including a CDRH1 sequence including GYTFTSYVIH (SEQ ID NO: 41), a CDRH2 sequence including YINPYNDGTDYDEKFKG (SEQ ID NO: 42), and a CDRH3 sequence including EKDNYATGAWFAY (SEQ ID NO: 43); and a variable light chain including a CDRL1 sequence including KSSQSLLYSTNQKNYLA (SEQ ID NO: 44), a CDRL2 sequence including WASTRES (SEQ ID NO: 45), and a CDRL3 sequence including QQYYSYRT (SEQ ID NO: 46). In particular embodiments, an antibody that binds to CD4 includes a commercially available antibody. An example of a commercially available anti-CD4 antibody is Clone GK1.5, Cat #BE0003-1, from BioXCell (West Lebanon, N.H.).

In particular embodiments, the T-DA includes an antibody or antibody fragment that binds to CD8. An example of an antibody that binds to CD8 is OKT8, the sequence of which is described in U.S. Publication No. US20160176969. The OKT8 anti-CD8 antibody includes a variable heavy chain including a CDRH1 sequence including FNIKDTY (SEQ ID NO: 47), a CDRH2 sequence including DPANDN (SEQ ID NO: 48), and a CDRH3 sequence including GYGYYVFDH (SEQ ID NO: 49); and a variable light chain including a CDRL1 sequence including RSISQY (SEQ ID NO: 50), a CDRL2 sequence including SGSTLQS (SEQ ID NO: 51), and a CDRL3 sequence including HNENPLT (SEQ ID NO: 52). In particular embodiments, an antibody that binds to CD8 includes a commercially available antibody. An example of a commercially available anti-CD8 antibody is Clone 2.43, Cat #BP0061, from BioXCell (West Lebanon, N.H.).

In particular embodiments, the T-DA includes an antibody or antibody fragment that binds to CD3. An example of an antibody that binds to CD3 is OKT3, the sequence of which is described in U.S. Pat. No. 6,491,916. The OKT3 anti-CD3 antibody includes a variable heavy chain including a CDRH1 sequence including RYTMH (SEQ ID NO: 53), a CDRH2 sequence including YINPSRGYTNYNQKFKD (SEQ ID NO: 54), and a CDRH3 sequence including YYDDHYCLDY (SEQ ID NO: 55); and a variable light chain including a CDRL1 sequence including SASSSVSYMN (SEQ ID NO: 56), a CDRL2 sequence including DTSKLAS (SEQ ID NO: 57), and a CDRL3 sequence including QQWSSNPFT (SEQ ID NO: 58). In particular embodiments, an antibody that binds to CD3 includes a commercially available antibody. An example of a commercially available anti-CD3 antibody is Clone KT3, Cat #MA5-16763, from Thermo Fisher Scientific (Waltham, Mass.).

In particular embodiments, a binding domain VH region can be derived from or based on a VH of a known monoclonal antibody and can contain one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the VH of a known antibody. An insertion, deletion or substitution may be anywhere in the VH region, including at the amino- or carboxy-terminus or both ends of this region, provided that each CDR includes zero changes or at most one, two, or three changes and provided a binding domain containing the modified VH region can still specifically bind its target with an affinity similar to the wild type binding domain.

In particular embodiments, a VL region in a binding domain is derived from or based on a VL of a known monoclonal antibody and contains one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions), or a combination of the above-noted changes, when compared with the VL of the known monoclonal antibody. An insertion, deletion or substitution may be anywhere in the VL region, including at the amino- or carboxy-terminus or both ends of this region, provided that each CDR includes zero changes or at most one, two, or three changes and provided a binding domain containing the modified VL region can still specifically bind its target with an affinity similar to the wild type binding domain.

In particular embodiments, a binding domain includes or is a sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a light chain variable region (VL) or to a heavy chain variable region (VH), or both, wherein each CDR includes zero changes or at most one, two, or three changes, from a monoclonal antibody or fragment or derivative thereof that specifically binds to target of interest.

Peptide aptamers include a peptide loop (which is specific for a target protein) attached at both ends to a protein scaffold. This double structural constraint greatly increases the binding affinity of the peptide aptamer to levels comparable to an antibody. The variable loop length is typically 8 to 20 amino acids (e.g., 8 to 12 amino acids), and the scaffold may be any protein which is stable, soluble, small, and non-toxic (e.g., thioredoxin-A, stefin A triple mutant, green fluorescent protein, eglin C, and cellular transcription factor Sp1). Peptide aptamer selection can be made using different systems, such as the yeast two-hybrid system (e.g., Gal4 yeast-two-hybrid system) or the LexA interaction trap system.

Nucleic acid aptamers are single-stranded nucleic acid (DNA or RNA) ligands that function by folding into a specific globular structure that dictates binding to target proteins or other molecules with high affinity and specificity, as described by Osborne et al., Curr. Opin. Chem. Biol. 1:5-9, 1997; and Cerchia et al., FEBS Letters 528:12-16, 2002. In particular embodiments, aptamers are small (15 KD; or between 15-80 nucleotides or between 20-50 nucleotides). Aptamers are generally isolated from libraries consisting of $10^{14}$-$10^{15}$ random oligonucleotide sequences by a procedure termed SELEX (systematic evolution of ligands by exponential enrichment; see, for example, Tuerk et al., Science, 249:505-510, 1990; Green et al., Methods Enzymology. 75-86, 1991; and Gold et al., Annu. Rev. Biochem., 64: 763-797, 1995). Further methods of generating aptamers are described in, for example, U.S. Pat. Nos. 6,344,318;

6,331,398; 6,110,900; 5,817,785; 5,756,291; 5,696,249; 5,670,637; 5,637,461; 5,595,877; 5,527,894; 5,496,938; 5,475,096; and 5,270,16. Spiegelmers are similar to nucleic acid aptamers except that at least one β-ribose unit is replaced by β-D-deoxyribose or a modified sugar unit selected from, for example β-D-ribose, α-D-ribose, β-L-ribose.

Binding domains can also be selected from affibodies; affilin (Ebersbach et al., J. Mol. Biol. 372: 172, 2007); armadillo repeat proteins (see, e.g., Madhurantakam et al., Protein Sci. 21: 1015, 2012; PCT Patent Application Publication No. WO 2009/040338); atrimers; avimers; C-type lectin domains (Zelensky and Gready, FEBS J. 272:6179, 2005; Beavil et al., Proc. Natl. Acad. Sci. (USA) 89:753, 1992 and Sato et al., Proc. Natl. Acad. Sci. (USA) 100:7779, 2003); cytotoxic T-lymphocyte associated protein-4 (Weidle et al., Cancer Gen. Proteo. 10:155, 2013); designed ankyrin repeat proteins (DARPins) (Binz et al., J. Mol. Biol. 332: 489, 2003 and Binz et al., Nat. Biotechnol. 22:575, 2004); fibrinogen domains (see, e.g., Weisel et al., Science 230: 1388, 1985); fibronectin binding domains (adnectins or monobodies) (Richards et al., J. Mol. Biol. 326:1475, 2003; Parker et al., Protein Eng. Des. Selec. 18:435, 2005 and Hackel et al. (2008) J. Mol. Biol. 381:1238-1252); fynomers; Kunitz domains (see, e.g., U.S. Pat. No. 6,423,498); leucine-rich repeat domains (Stumpp et al., J. Mol. Biol. 332:471, 2003); lipocalin domains (see, e.g., WO 2006/095164, Beste et al., Proc. Natl. Acad. Sci. (USA) 96:1898, 1999 and Schonfeld et al., Proc. Natl. Acad. Sci. (USA) 106:8198, 2009); mAb2 or Fcab™ (see, e.g., PCT Patent Application Publication Nos. WO 2007/098934; WO 2006/072620); scTCR (see, e.g., Lake et al., Int. Immunol. 11:745, 1999; Maynard et al., J. Immunol. Methods 306:51, 2005; U.S. Pat. No. 8,361,794); tetratricopeptide repeat domains (Main et al., Structure 11:497, 2003 and Cortajarena et al., ACS Chem. Biol. 3:161, 2008); V-like domains (see, e.g., U.S. Patent Application Publication No. 2007/0065431); or the like (see, e.g., Nord et al., Protein Eng. 8:601, 1995; Nord et al., Nat. Biotechnol. 15:772, 1997; Nord et al., Euro. J. Biochem. 268:4269, 2001; Binz et al., Nat. Biotechnol. 23:1257, 2005; Boersma and Pluckthun, Curr. Opin. Biotechnol. 22:849, 2011).

Other agents that can facilitate internalization by and/or transfection of T cells, such as poly(ethyleneimine)/DNA (PEI/DNA) complexes can also be used.

V. Endosomal Release Agents (ERA). Endosomal release agents (ERA) include any compound or peptide that facilitates cargo exit from the endosome of a T cell. Exemplary ERA include imidazoles, poly or oligoimidazoles, PEIs, peptides, fusogenic peptides, polycarboxylates, polycations, masked oligo or poly cations or anions, acetals, polyacetals, ketals/polyketals, orthoesters, polymers with masked or unmasked cationic or anionic charges, amphiphilic block copolymers and dendrimers with masked or unmasked cationic or anionic charges.

Many ERA are adapted from viral elements that promote escape from the endosome and deliver polynucleotides intact into the nucleus. As one particular example, the H5WYG peptide can be used to induce the lysis of membranes at low pH. The histidine-rich peptide H5WYG is a derivative of the N-terminal sequence of the HA-2 subunit of the influenza virus hemagglutinin in which 5 of the amino acids have been replaced with histidine residues. H5WYG is able to selectively destabilize membranes at a slightly acidic pH as the histidine residues are protonated. The E1 protein from Semliki Forrest virus is also a useful ERA.

In particular embodiments, ERA include a hydrophobic membrane translocation sequence (MTS). An exemplary hydrophobic MTS-containing peptide is RFGF having the amino acid sequence AAVALLPAVLLALLAP (SEQ ID NO: 59). An RFGF analogue (e.g., amino acid sequence AALLPVLLAAP (SEQ ID NO: 60)) containing a hydrophobic MTS can also be used.

Additional exemplary ERA include:

| Source | Sequence |
|---|---|
| Influenza virus hemagglutinin HA-2 | GLFEAIAGFIENGWEG (SEQ ID NO: 61) |
| TAT of HIV | YGRKKRRQRRR (SEQ ID NO: 62) |
| N-terminal region of the S protein of duck hepatitis B | MSGTFGGILAGLIGLL (SEQ ID NO: 63) |
| S protein of woodchuck hepatitis B | MSPSSLLGLLAGLQVV (SEQ ID NO: 64) |
| Synthetic, Duguid et al. 1998 | GLFEALLELLESLWELL (SEQ ID NO: 65) |
| Synthetic, Gupta & Kothekar, 1997 | LKKLLKKLLKKLLKKL (SEQ ID NO: 66) |
| Derossi et al., J. Biol. Chem. 269: 10444, 1994 | RQIKIWFQNRRMKWKK (SEQ ID NO: 67) |
| Tat fragment (48-60) | GRKKRRQRRRPPQC (SEQ ID NO: 68) |
| Chaloin et al., Biochem. peptide Biophys. Res. Commun., 243: 601, 1998 | GALFLGWLGAAGSTMGAWSQPKKKRKV (SEQ ID NO: 69) |
| PVEC | LLIILRRRIRKQAHAHSK (SEQ ID NO: 70) |
| Transportan | GWTLNSAGYLLKINLKALAALAKKIL (SEQ ID NO: 71) |
| Amphiphilic model peptide; Oehlke et al., Mol. Ther., 2: 339, 2000 | KLALKLALKALKAALKLA (SEQ ID NO: 72) |
| Arg$_9$ | RRRRRRRRR (SEQ ID NO: 73) |

| Source | Sequence |
|---|---|
| LL-37 | LLGDFFRKSKEKIGKEFKRIVQRIKDFLRNLVPRTES (SEQ ID NO: 74) |
| Cecropin P1 | SWLSKTAKKLENSAKKRISEGIAIAIQGGPR (SEQ ID NO: 75) |
| α-defensin | ACYCRIPACIAGERRYGTCIYQGRLWAFCC (SEQ ID NO: 76) |
| β-defensin | DHYNCVSSGGQCLYSACPIFTKIQGTCYRGKAKCCK (SEQ ID NO: 77) |
| Bactenecin | RKCRIVVIRVCR (SEQ ID NO: 78) |
| PR-3 | RRRPRPPYLPRPRPPPFFPPRLPPRIPPGFPPRFPPRFP GKR-NH$_2$ (SEQ ID NO: 79) |
| Indolicidin | ILPWKWPWWPWRR-NH$_2$ (SEQ ID NO: 80) |

VI. Nuclear Targeting Agents. Nuclear Targeting Agents (NTA) refer to sequences that enhance cellular transport to and/or entry into the nucleus of a cell. Generally, NTA are a class of short amino acid sequences from 3 to 100 amino acids in length, from 3 to 50, 4 to 30, or 4 to 20 amino acids in length.

Microtubule-associated sequence (MTAS) NTA include those that facilitate interaction with microtubules to enhance transport to the nucleus. An exemplary MTAS includes PLKTPGKKKKGKPGKRKEQEKKKRRTR (SEQ ID NO: 81).

Nuclear localization signal (NLS) NTA include those that facilitate interaction with nuclear transport machinery. An exemplary NLS sequence includes GRYLTQETNKVETYKEQ PLKTPGKKKKGKP (SEQ ID NO: 82).

Particular embodiments utilize NTA derived from the human parathyroid hormone related protein (PTHrP, UniProt ID: P12272), which is a protein that includes overlapping MTAS and NLS sequences. In particular embodiments, the NTA including an overlapping MTAS and NLS sequence includes GRYLTQETNKVETYKEQPLKTPGKKKKGKPGKRKE QEKKKRRTR (SEQ ID NO: 83; see Narayanan, et al., Sci Rep. 2013; 3:2184).

Additional exemplary NLS sequences include (i) monopartite NLS exemplified by the SV40 large T antigen NLS (PKKKRKV) (SEQ ID NO: 84); (ii) bipartite NLS including two basic domains separated by a variable number of spacer amino acids and exemplified by the Xenopus nucleoplasmin NLS (KRXXXXXXXXXXKKKL) (SEQ ID NO: 85); and (iii) noncanonical sequences such as M9 of the hnRNP A1 protein, the influenza virus nucleoprotein NLS, and the yeast Gal4 protein NLS (Dingwall and Laskey, Trends Biochem Sci 16:478-481, 1991). In particular embodiments, the NLS can be a highly cationic or basic peptide. In particular embodiments, the NLS includes two or more Arg or Lys amino acid residues. In particular embodiments, the NLS can bind cytosolic proteins, such as importins and karyopherins, which recognize and transport NLS-containing sequences to the nuclear pore complex.

In particular embodiments, to direct import of delivered PN, particularly plasmid DNA, into the nucleus, PN (e.g., nanoparticle-encapsulated plasmids) can be conjugated to the SV40 T-Ag-derived NLS peptides. Exemplary SV40 T-Ag-derived NLS peptides include: PKKKRKV (SEQ ID NO: 86); PKKKRMV (SEQ ID NO: 87); PKKKRKVEDP (SEQ ID NO: 88); PKKGSKKA (SEQ ID NO: 89); PKTKRKV (SEQ ID NO: 90); CGGPKKKRKVG (SEQ ID NO: 91); PKKKIKV (SEQ ID NO: 92); CYDDEAT-ADSQHSTPPKKKRKVEDPKDFESELLS (SEQ ID NO: 93); and CGYGPKKKRKVGG (SEQ ID NO: 94).

Additional exemplary NLS sequences include:

| Source | Sequence |
|---|---|
| Polyoma large T protein | PKKARED (SEQ ID NO: 95) |
| Polyoma large T protein | CGYGVSRKRPRPG (SEQ ID NO: 96) |
| SV40 VP1 capsid polypeptide | APTKRKGS (SEQ ID NO: 97) |
| Polyoma virus major capsid protein VP1 | APKRKSGVSKC (SEQ ID NO: 98) |
| SV40 VP2 capsid protein | PNKKKRK (SEQ ID NO: 99) |
| Polyoma virus capsid protein VP2 | EEDGPQKKKRRL (SEQ ID NO: 100) |
| Yeast histone H2B | GKKRSKA (SEQ ID NO: 101) |
| Adenovirus E1a | KRPRP (SEQ ID NO: 102) |
| Adenovirus type 2/5 E1a | CGGLSSKRPRP (SEQ ID NO: 103) |
| Xenopus NLS2 | LKDKDAKKSKQE (SEQ ID NO: 104) |

| Source | Sequence |
|---|---|
| v-Rel or p59$^{v-rel}$ | GNKAKRQRST (SEQ ID NO: 105) |
| Influenza A NS1 protein | PFLDRLRRDQK (SEQ ID NO: 106) |
| Human lamin A | SVTKKRKLE (SEQ ID NO: 107) |
| Xenopus lamin A | SASKRRRLE (SEQ ID NO: 108) |
| Adenovirus 5 DBP | PPKKRMRRRIE (SEQ ID NO: 109) |
| Rat glucocorticoid receptor | YRKCLQAGMNLEARKTKKKIKGIQQATA (SEQ ID NO: 110) |
| Human estrogen receptor | RKDRRGGRMLKHKRQRDDGEGRGEVGSAG DMRAMINACIDNLWPSPLMIKRSKK (SEQ ID NO: 111) |
| Rabbit progesterone receptor | RKFKKFNK (SEQ ID NO: 112) |
| c-myb gene product | PLLKKIKQ (SEQ ID NO: 113) |
| N-myc gene product | PPQKKIKS (SEQ ID NO: 114) |
| p53 | PQPKKKP (SEQ ID NO: 115) |
| c-erb-A gene product | SKRVAKRKL (SEQ ID NO: 116) |
| Yeast ribosomal protein L29 | MTGSKTRKHRGSGA (SEQ ID NO: 117) |
| Yeast ribosomal protein L29 | RHRKHP (SEQ ID NO: 118) |
| Yeast ribosomal protein L29 | KRRKHP (SEQ ID NO: 119) |
| Yeast ribosomal protein L29 | KYRKHP (SEQ ID NO: 120) |
| Yeast ribosomal protein L29 | KHRRHP (SEQ ID NO: 121) |
| Yeast ribosomal protein L29 | KHKKHP (SEQ ID NO: 122) |
| Yeast ribosomal protein L29 | RHLKHP (SEQ ID NO: 123) |
| Hepatitis B core antigen | PETTVVRRRGRSPRRRTPSPRRRRSPRRRR SQS (SEQ ID NO: 124) |
| Viral jun | ASKSRKRKL (SEQ ID NO: 125) |
| Human T cell leukemia virus Tax trans-activator protein | GGLCSARLHRHALLAT (SEQ ID NO: 126) |
| Mouse nuclear Mx1 protein | DTREKKKFLKRRLLRLDE (SEQ ID NO: 127) |

Exemplary NLS are also described in Cokol et al., 2000, EMBO Reports, 1(5):411-415; Boulikas, 1993, Crit. Rev. Eukaryot. Gene Expr., 3:193-227; Collas et al., 1996, Transgenic Research, 5: 451-458; Collas and Alestrom, 1997, Biochem. Cell Biol. 75: 633-640; Collas and Alestrom, 1998, Transgenic Research, 7: 303-309; Collas and Alestrom, 1996, Mol. Reprod. Devel., 45:431-438, and U.S. Pat. Nos. 7,531,624; 7,498,177; 7,332,586; and 7,550,650.

In particular embodiments, NTA are covalently coupled to a polymer of a NP, for example, PBAE.

VII. Vaccine Antigens. Within the teachings of the current disclosure, T cells are genetically modified to express a TCR specific for a vaccine antigen that is administered to a subject. A vaccine antigen is a substance that, when introduced to the body stimulates an immune response, such as T cell activation and/or antibody production. Vaccine antigens can include natural intact pathogens, such as a killed bacterium or virus, or a live attenuated virus or can include only portions, or subunits, of a pathogen, such as a single virus or bacterium protein. Vaccine antigens can also include cancer antigens or fragments thereof.

Exemplary viral vaccine antigens can be derived from adenoviruses, arenaviruses, bunyaviruses, coronaviruses, flavirviruses, hantaviruses, hepadnaviruses, herpesviruses, papilomaviruses, paramyxoviruses, parvoviruses, picornaviruses, poxviruses, orthomyxoviruses, retroviruses, reoviruses, rhabdoviruses, rotaviruses, spongiform viruses or togaviruses. In particular embodiments, vaccine antigens include peptides expressed by viruses including CMV, EBV, flu viruses, hepatitis A, B, or C, herpes simplex, HIV, influenza, Japanese encephalitis, measles, polio, rabies, respiratory syncytial, rubella, smallpox, varicella zoster, West Nile, and/or Zika.

Examples of vaccine antigens that are derived from whole pathogens include the attenuated polio virus used for the OPV polio vaccine, and the killed polio virus used for the IPV polio vaccine.

As further particular examples, CMV vaccine antigens include envelope glycoprotein B and CMV pp65; EBV vaccine antigens include EBV EBNAI, EBV P18, and EBV P23; hepatitis vaccine antigens include the S, M, and L proteins of hepatitis B virus, the pre-S antigen of hepatitis B virus, HBCAG DELTA, HBV HBE, hepatitis C viral RNA, HCV NS3 and HCV NS4; herpes simplex vaccine antigens include immediate early proteins and glycoprotein D; human immunodeficiency virus (HIV) vaccine antigens include gene products of the gag, pol, and env genes such as HIV gp32, HIV gp41, HIV gp120, HIV gp160, HIV P17/24, HIV P24, HIV P55 GAG, HIV P66 POL, HIV TAT, HIV GP36, the Nef protein and reverse transcriptase; human papillomavirus virus (HPV) viral antigens include the L1 protein; influenza vaccine antigens include hemagglutinin and neuraminidase; Japanese encephalitis vaccine antigens include proteins E, M-E, M-E-NS1, NS1, NS1-NS2A and 80% E; malaria vaccine antigens include the Plasmodium proteins circumsporozoite (CSP), glutamate dehydrogenase, lactate dehydrogenase, and fructose-bisphosphate aldolase; measles vaccine antigens include the measles virus fusion protein; rabies vaccine antigens include rabies glycoprotein and rabies nucleoprotein; respiratory syncytial vaccine antigens include the RSV fusion protein and the M2 protein; rotaviral vaccine antigens include VP7sc; rubella vaccine antigens include proteins E1 and E2; varicella zoster vaccine antigens include gpl and gpll; and zika vaccine antigens include pre-membrane, envelope (E), Domain III of the E protein, and non-structural proteins 1-5.

Additional particular exemplary viral antigen sequences include:

| Source | Sequence |
| --- | --- |
| Nef (66-97): | VGFPVTPQVPLRPMTYKAAVDLSHFLKEKGGL (SEQ ID NO: 128) |
| Nef (116-145) | HTQGYFPDWQNYTPGPGVRYPLTFGWLYKL (SEQ ID NO: 129) |
| Gag p17 (17-35) | EKIRLRPGGKKKYKLKHIV (SEQ ID NO: 130) |
| Gag p17-p24 (253-284) | NPPIPVGEIYKRWIILGLNKIVRMYSPTSILD (SEQ ID NO: 131) |
| Pol 325-355 (RT 158-188) | AIFQSSMTKILEPFRKQNPDIVIYQYMDDLY (SEQ ID NO: 132) |
| CSP central repeat region | NANPNANPNANPNANPNANP (SEQ ID NO: 133) |
| E protein Domain III | AFTFTKIPAETLHTVTEVQYAGTDGPCKVPAQMAVDMQTLTPVGRLITANPVIT EGTENSKMMLELDPPFGDSYIVIGVGE (SEQ ID NO: 134) |

See Fundamental Virology, Second Edition, eds. Fields, B. N. and Knipe, D. M. (Raven Press, New York, 1991) for additional examples of viral antigens.

In particular embodiments, vaccine antigens are expressed by cells associated with bacterial infections. Exemplary bacteria include anthrax; gram-negative bacilli, chlamydia, diptheria, haemophilus influenza, *Helicobacter pylori, Mycobacterium tuberculosis*, pertussis toxin, pneumococcus, rickettsiae, staphylococcus, streptococcus and tetanus.

As particular examples of bacterial vaccine antigens, anthrax vaccine antigens include anthrax protective antigen; gram-negative bacilli vaccine antigens include lipopolysaccharides; haemophilus influenza vaccine antigens include capsular polysaccharides; diptheria vaccine antigens include diptheria toxin; *Mycobacterium tuberculosis* vaccine antigens include mycolic acid, heat shock protein 65 (HSP65), the 30 kDa major secreted protein and antigen 85A; pertussis toxin vaccine antigens include hemagglutinin, pertactin, FIM2, FIM3 and adenylate cyclase; pneumococcal vaccine antigens include pneumolysin and pneumococcal capsular polysaccharides; rickettsiae vaccine antigens include rompA; streptococcal vaccine antigens include M proteins; and tetanus vaccine antigens include tetanus toxin.

In particular embodiments, vaccine antigens are derived from multi-drug resistant "superbugs." Examples of superbugs include Enterococcus faecium, Clostridium difficile, Acinetobacter baumannii, Pseudomonas aeruginosa, and Enterobacteriaceae (including Escherichia coli, Klebsiella pneumoniae, Enterobacter spp.).

Vaccine antigens can also include proteins that are specifically or preferentially expressed by cancer cells in order to activate the immune system to fight cancer. Examples of cancer antigens include A33; BAGE; B-cell maturation antigen (BCMA); Bcl-2; β-catenin; CA19-9; CA125; carboxy-anhydrase-IX (CAIX); CD5; CD19; CD20; CD21; CD22; CD24; CD33; CD37; CD45; CD123; CD133; CEA; c-Met; CS-1; cyclin B1; DAGE; EBNA; EGFR; ephrinB2; estrogen receptor; FAP; ferritin; folate-binding protein; GAGE; G250; GD-2; GM2; gp75, gp100 (Pmel 17); HER-2/neu; HPV E6; HPV E7; Ki-67; L1-CAM; LRP; MAGE; MART; mesothelin; MUC; MUM-1-B; myc; NYESO-1; p53, PRAME; progesterone receptor; PSA; PSCA; PSMA; ras; RORI; survivin; SV40 T; tenascin; TSTA tyrosinase; VEGF; and WT1.

As more particular examples, cancer vaccine antigens can include or be derived from:

| Cancer Antigen | Sequence |
|---|---|
| PSMA | MWNLLHETDSAVATARRPRWLCAGALVLAGGFFLLGFLFGWFIKSSNEATNIT PKHNMKAFLDELKAENIKKFLYNFTQIPHLAGTEQNFQLAKQIQSQWKEFGLDS VELAHYDVLLSYPNKTHPNYISIINEDGNEIFNTSLFEPPPPGYENVSDIVPPFSA FSPQGMPEGDLVYVNYARTEDFFKLERDMKINCSGKIVIARYGKVFRGNKVKN AQLAGAKGVILYSDPADYFAPGVKSYPDGWNLPGGGVQRGNILNLNGAGDPL TPGYPANEYAYRRGIAEAVGLPSIPVHPIGYYDAQKLLEKMGGSAPPDSSWRG SLKVPYNVGPGFTGNFSTQKVKMHIHSTNEVTRIYNVIGTLRGAVEPDRYVILG GHRDSWVFGGIDPQSGAAVVHEIVRSFGTLKKEGWRPRRTILFASWDAEEFG LLGSTEWAEENSRLLQERGVAYINADSSIEGNYTLRVDCTPLMYSLVHNLTKEL KSPDEGFEGKSLYESWTKKSPSPEFSGMPRISKLGSGNDFEVFFQRLGIASGR ARYTKNWETNKFSGYPLYHSVYETYELVEKFYDPMFKYHLTVAQVRGGMVFE LANSIVLPFDCRDYAVVLRKYADKIYSISMKHPQEMKTYSVSFDSLFSAVKNFTE IASKFSERLQDFDKSNPIVLRMMNDQLMFLERAFIDPLGLPDRPFYRHVIYAPSS HNKYAGESFPGIYDALFDIESKVDPSKAWGEVKRQIYVAAFTVQAAAETLSEVA (SEQ ID NO: 135) |
| PSCA | MKAVLLALLMAGLALQPGTALLCYSCKAQVSNEDCLQVENCTQLGEQCWTARI RAVGLLTVISKGCSLNCVDDSQDYYVGKKNITCCDTDLCNASGAHALQPAAAIL ALLPALGLLLWGPGQL (SEQ ID NO: 136) |
| Mesothelin | MALPTARPLLGSCGTPALGSLLFLLFSLGWVQPSRTLAGETGQEAAPLDGVLA NPPNISSLSPRQLLGFPCAEVSGLSTERVRELAVALAQKNVKLSTEQLRCLAHR LSEPPEDLDALPLDLLLFLNPDAFSGPQACTHFFSRITKANVDLLPRGAPERQR LLPAALACWGVRGSLLSEADVRALGGLACDLPGRFVAESAEVLLPRLVSCPGP LDQDQQEAARAALQGGGPPYGPPSTWSVSTMDALRGLLPVLGQPIIRSIPQGI VAAWRQRSSRDPSWRQPERTILRPRFRREVEKTACPSGKKAREIDESLIFYKK WELEACVDAALLATQMDRVNAIPFTYEQLDVLKHKLDELYPQGYPESVIQHLG YLFLKMSPEDIRKWNVTSLETLKALLEVNKGHEMSPQVATLIDRFVKGRGQLDK DTLDTLTAFYPGYLCSLSPEELSSVPPSSIWAVRPQDLDTCDPRQLDVLYPKAR LAFQNMNGSEYFVKIQSFLGGAPTEDLKALSQQNVSMDLATFMKLRTDAVLPL TVAEVQKLLGPHVEGLKAEERHRPVRDWILRQRQDDLDTLGLGLQGGIPNGYL VLDLSVQEALSGTPCLLGPGPVLTVLALLLASTLA (SEQ ID NO: 137) |
| CD19 | MPPPRLLFFLLFLTPMEVRPEEPLVVKVEEGDNAVLQCLKGTSDGPTQQLTWS RESPLKPFLKLSLGLPGLGIHMRPLASWLFIFNVSQQMGGFYLCQPGPPSEKA WQPGWTVNVEGSGELFRWNVSDLGGLGCGLKNRSSEGPSSPSGKLMSPKLY VWAKDRPEIWEGEPPCVPPRDSLNQSLSQDLTMAPGSTLWLSCGVPPDSVSR GPLSWTHVHPKGPKSLLSLELKDDRPARDMWVMETGLLLPRATAQDAGKYYC HRGNLTMSFHLEITARPVLWHWLLRTGGWKVSAVTLAYLIFCLCSLVGILHLQR ALVLRRKRKRMTDPTRRFFKVTPPPGSGPQNQYGNVLSLPTPTSGLGRAQRW AAGLGGTAPSYGNPSSDVQADGALGSRSPPGVGPEEEEGEGYEEPDSEEDS EFYENDSNLGQDQLSQDGSGYENPEDEPLGPEDEDSFSNAESYENEDEELTQ PVARTMDFLSPHGSAWDPSREATSLGSQSYEDMRGILYAAPQLRSIRGQPGP NHEEDADSYENMDNPDGPDPAWGGGGRMGTWSTR (SEQ ID NO: 138) |
| CD20 | MTTPRNSVNGTFPAEPMKGPIAMQSGPKPLFRRMSSLVGPTQSFFMRESKTL GAVQIMNGLFHIALGGLLMIPAGIYAPICVTVWYPLWGGIMYIISGSLLAATEKNS RKCLVKGKMIMNSLSLFAAISGMILSIMDILNIKISHFLKMESLNFIRAHTPYINIYN CEPANPSEKNSPSTQYCYSIQSLFLGILSVMLIFAFFQELVIAGIVENEWKRTCS RPKSNIVLLSAEEKKEQTIEIKEEVVGLTETSSQPKNEEDIEIIPIQEEEEEETETN FPEPPQDQESSPIENDSSP (SEQ ID NO: 139) |
| ROR1 | MHRPRRGTRPPLLALLAALLLAARGAAAQETELSVSAELVPTSSWNISSELNK DSYLTLDEPMNNITTSLGQTAELHCKVSGNPPPTIRWFKNDAPVVQEPRRLSF RSTIYGSRLRIRNLDTTDTGYFQCVATNGKEVVSSTGVLFVKFGPPPTASPGYS DEYEEDGFCQPYRGIACARFIGNRTVYMESLHMQGEIENQITAAFTMIGTSSHL SDKCSQFAIPSLCHYAFPYCDETSSVPKPRDLCRDECEILENVLCQTEYIFARS NPMILMRLKLPNCEDLPQPESPEAANCIRIGIPMADPINKNHKCYNSTGVDYRG TVSVTKSGRQCQPWNSQYPHTHTFTALRFPELNGGHSYCRNPGNQKEAPWC FTLDENFKSDLCDIPACDSKDSKEKNKMEILYILVPSVAIPLAIALLFFFICVCRNN QKSSSAPVQRQPKHVRGQNVEMSMLNAYKPKSKAKELPLSAVRRMEELGEC AFGKIYKGHLYLPGMDHAQLVAIKTLKDYNNPQQWTEFQQEASLMAELHHPNI VCLLGAVTQEQPVCMLFEYINQGDLHEFLIMRSPHSDVGCSSDEDGTVKSSLD HGDPLHIAIQIAAGMEYLSSHFFVHKDLAARNILIGEQLHVKISDLGLSREIYSAD YYRVQSKSLLPIRWMPPEAIMYGKFSSDSDIWSFGVVLWEIFSFGLQPYYGFS NQEVIEMVRKRQLLPCSEDCPPRMYSLMTECWNE1PSRRPRFKDIHVRLRSW EGLSSHTSSTTPSGGNATTQTTSLSASPVSNLSNPRYPNYMFPSQGITPQGQI |

| Cancer Antigen | Sequence |
|---|---|
| | AGFIGPPIPQNQRFIPINGYPIPPGYAAFPAAHYQPTGPPRVIQHCPPPKSRSPS SASGSTSTGHVTSLPSSGSNQEANIPLLPHMSIPNHPGGMGITVFGNKSQKPY KIDSKQASLLGDANIHGHTESMISAEL (SEQ ID NO: 140) |
| WT1 | MGHHHHHHHHHSSGHIEGRHMRRVPGVAPTLVRSASETSEKRPFMCAYPG CNKRYFKLSHLQMHSRKHTGEKPYQCDFKDCERRFFRSDQLKRHQRRHTGV KPFQCKTCQRKFSRSDHLKTHTRTHTGEKPFSCRWPSCQKKFARSDELVRHH NMHQRNMTKLQLAL (SEQ ID NO: 141) |

VIII. Vaccine Adjuvants. Vaccines are often administered with vaccine adjuvants. The term "adjuvant" refers to material that enhances the immune response to an antigen and is used herein in the customary use of the term. The precise mode of action is not understood for all adjuvants, but such lack of understanding does not prevent their clinical use for a wide variety of vaccines.

Exemplary vaccine adjuvants, include any kind of Toll-like receptor ligand or combinations thereof (e.g. CpG, Cpg-28 (a TLR9 agonist), Polyriboinosinic polyribocytidylic acid (Poly(I:C)), α -galactoceramide, MPLA, Motolimod (VTX-2337, a novel TLR8 agonist developed by VentiRx), IMO-2055 (EMD1201081), TMX-101 (imiquimod), MGN1703 (a TLR9 agonist), G100 (a stabilized emulsion of the TLR4 agonist glucopyranosyl lipid A), Entolimod (a derivative of Salmonella flagellin also known as CBLB502), Hiltonol (a TLR3 agonist), and Imiquimod), and/or inhibitors of heat-shock protein 90 (Hsp90), such as 17-DMAG (17-dimethylaminoethylamino-17-demethoxygeldanamycin).

In particular embodiments a squalene-based adjuvant can be used. Squalene is part of the group of molecules known as triterpenes, which are all hydrocarbons with 30 carbon molecules. Squalene can be derived from certain plant sources, such as rice bran, wheat germ, amaranth seeds, and olives, as well as from animal sources, such as shark liver oil. In particular embodiments, the squalene-based adjuvant is MF59® (Novartis, Basel, Switzerland). An example of a squalene-based adjuvant that is similar to MF59® but is designed for preclinical research use is Addavax™ (InvivoGen, San Diego, Calif.). MF59 has been FDA approved for use in an influenza vaccine, and studies indicate that it is safe for use during pregnancy (Tsai T, et al. Vaccine. 2010. 17:28(7):1877-80; Heikkinen T, et al. Am J Obstet Gynecol. 2012. 207(3):177). In particular embodiments, squalene based adjuvants can include 0.1%-20% (v/v) squalene oil. In particular embodiments, squalene based adjuvants can include 5% (v/v) squalene oil.

In particular embodiments the adjuvant alum can be used. Alum refers to a family of salts that contain two sulfate groups, a monovalent cation, and a trivalent metal, such as aluminum or chromium. Alum is an FDA approved adjuvant. In particular embodiments, vaccines can include alum in the amounts of 1-1000 µg/dose or 0.1 mg-10 mg/dose. In particular embodiments, the adjuvant Vaxfectin® (Vical, Inc., San Diego, Calif.) can be used. Vaxfectin® is a cationic lipid based adjuvant.

In particular embodiments, one or more STING agonists are used as a vaccine adjuvant. "STING" is an abbreviation of "stimulator of interferon genes", which is also known as "endoplasmic reticulum interferon stimulator (ERIS)", "mediator of IRF3 activation (MITA)", "MPYS" or "transmembrane protein 173 (TM173)". STING is a transmembrane receptor protein and is encoded by the gene TMEM173 in human. Activation of STING leads to production of Type I interferons (e.g. IFN-α and IFN-β), via the IRF3 (interferon regulatory factor 3) pathway; and to production of pro-inflammatory cytokines (e.g. TNF-α and IL-Iβ), via the NF-κB pathway and/or the NLRP3 inflammasome.

Human and murine STING are naturally activated two ways: via binding of exogenous (3',3) cyclic dinucleotides (c-diGMP, c-diAMP and c-GAMP) that are released by invading bacteria or archaea; and via binding of (2',3')cyclic guanosine monophosphate-adenosine monophosphate ((2', 3')c-GAMP), an endogenous cyclic dinucleotide that is produced by the enzyme cyclic GMP-AMP synthase (cGAS; also known as C6orfl50 or MB21D1) in the presence of exogenous double-stranded DNA (e.g. that released by invading bacteria, viruses or protozoa).

The term "STING agonist" refers to a substance that activates the STING receptor in vitro or in vivo. A compound can be deemed a STING agonist if: (i) induces Type I interferons in vitro in human or animal cells that contain STING; and (ii) does not induce Type I interferons in vitro in human or animal cells that do not contain STING or does not contain functioning STING. A typical test to ascertain whether a ligand is a STING agonist is to incubate the ligand in a wild-type human or animal cell line and in the corresponding cell line in which the STING coding gene has been genetically inactivated by a few bases or a longer deletion (e.g. a homozygous STING knockout cell line). An agonist of STING will induce Type I interferon in the wild-type cells but will not induce Type I interferon in the cells in which STING is inactivated.

In particular embodiments, STING agonists include cyclic molecules with one or two phosphodiester linkages, and/or one or two phosphorothioate diester linkages, between two nucleotides. This includes (3',5')-(3',5') nucleotide linkages (abbreviated as (3',3')); (3',5')-(2',5') nucleotide linkages (abbreviated as (3',2')); (2',5')-(3',5') nucleotide linkages (abbreviated as (2',3')); and (2',5')-(2',5') nucleotide linkages (abbreviated as (2',2')). "Nucleotide" refers to any nucleoside linked to a phosphate group at the 5',3' or 2' position of the sugar moiety.

In particular embodiments, STING agonists include compounds of the formula:

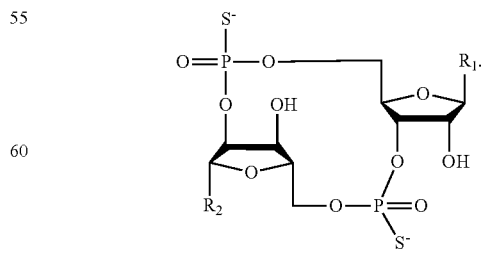

In particular embodiments, R1 and R2 may be independently 9-purine, 9-adenine, 9-guanine, 9-hypoxanthine, 9-xanthine, 9-uric acid, or 9-isoguanine, as shown below:

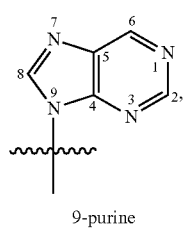

9-purine

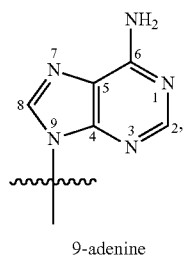

9-adenine

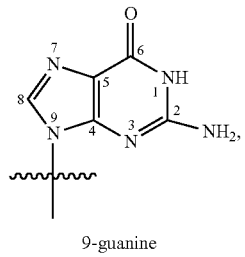

9-guanine

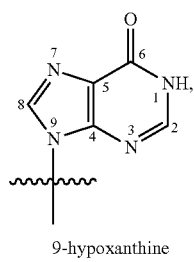

9-hypoxanthine

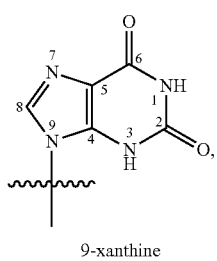

9-xanthine

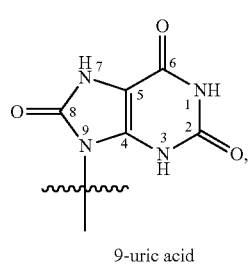

9-uric acid

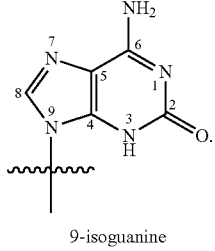

9-isoguanine

In particular embodiments, the STING agonist can include dithio-(RP, RP)-[cyclic[A(2',5')pA(3',5')p]] (also known as 2'-5',3'-5' mixed phosphodiester linkage (ML) RR-S2 c-diAMP or ML RR-S2 CDA), ML RR-S2-c-di-GMP (ML-CDG), ML RR-S2 cGAMP, or any mixtures thereof.

The structure of c-diGMP includes:

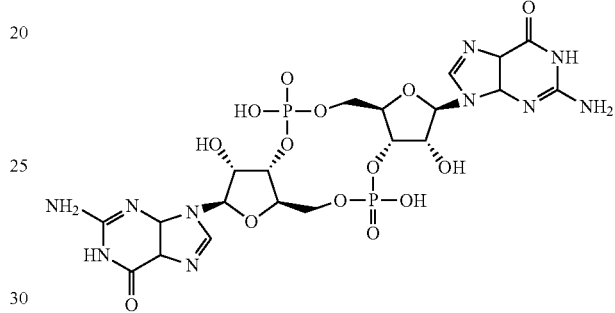

The structure of c-diAMP includes:

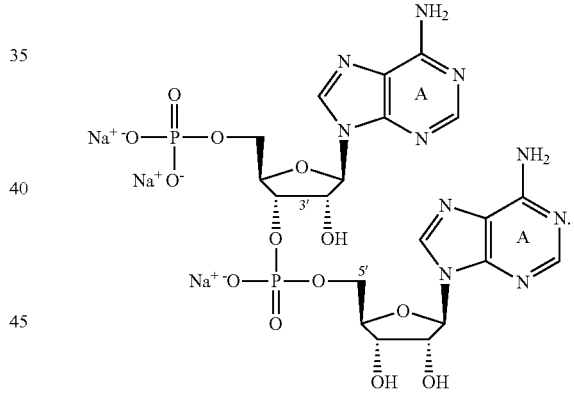

The structure of c-GAMP includes:

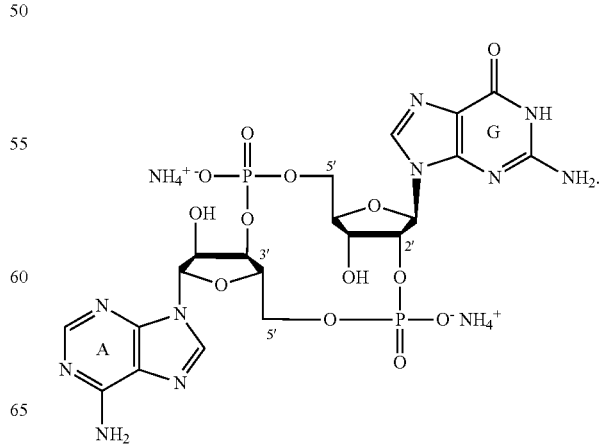

Additional particular examples of STING agonists include c-AIMP; (3',2')c-AIMP; (2',2')c-AIMP; (2',3')c-AIMP; c-AIMP(S); c-(dAMP-dIMP); c-(dAMP-2'FdIMP); c-(2'FdAMP-2'FdIMP); (2',3')c-(AMP-2'FdIMP); c-[2'FdAMP(S)-2'FdIMP(S)]; c-[2'FdAMP(S)-2'FdIMP(S)] (POM)2; and DMXAA. Additional examples of STING agonists are described in WO2016/145102.

Other immune stimulants can also be used as vaccine adjuvants. Additional exemplary small molecule immune stimulants include TGF-β inhibitors, SHP-inhibitors, STAT-3 inhibitors, and/or STAT-5 inhibitors. Exemplary siRNA capable of down-regulating immune-suppressive signals or oncogenic pathways (such as kras) can be used whereas any plasmid DNA (such as minicircle DNA) encoding immune-stimulatory proteins can also be used.

Exemplary cytokines include IL-2, IL-7, IL-12, IL-15, IL-18, IL-21, TNFα, IFN-α, IFN-β, IFN-γ, or GM-CSF. In particular embodiments, the immune stimulant may be a cytokine and or a combination of cytokines, such as IL-2, IL-12 or IL-15 in combination with IFN-α, IFN-β or IFN-γ, or GM-CSF, or any effective combination thereof, or any other effective combination of cytokines. The above-identified cytokines stimulate $T_H1$ responses, but cytokines that stimulate $T_H2$ responses may also be used, such as IL-4, IL-10, IL-11, or any effective combination thereof. Also, combinations of cytokines that stimulate $T_H1$ responses along with cytokines that stimulate $T_H2$ responses may be used.

Immune stimulants derived from the molecules noted in the preceding paragraphs can also be used. For example, RLI is an IL-15-IL-15 receptor-α fusion protein that exhibits 50-fold greater potency than IL-15 alone. IL-15 particularly impacts anti-tumor immune response at multiple points. It can differentiate monocytes into stimulatory antigen presenting cells; promote the effector functions and proliferation of tumor-reactive T cells; and recruit and activate NK cells.

IX. Compositions. The polynucleotides, NP, vaccine antigens, and/or vaccine adjuvants disclosed herein (individually, collectively, or in grouped combinations referred to as "active ingredients") can be provided as part of compositions formulated for administration to subjects.

In particular embodiments, the active ingredients are provided as part of a composition that can include, for example, at least 0.1% w/v or w/w of active ingredient(s); at least 1% w/v or w/w of active ingredient(s); at least 10% w/v or w/w of active ingredient(s); at least 20% w/v or w/w of active ingredient(s); at least 30% w/v or w/w of active ingredient(s); at least 40% w/v or w/w of active ingredient(s); at least 50% w/v or w/w of active ingredient(s); at least 60% w/v or w/w of active ingredient(s); at least 70% w/v or w/w of active ingredient(s); at least 80% w/v or w/w of active ingredient(s); at least 90% w/v or w/w of active ingredient(s); at least 95% w/v or w/w of active ingredient(s); or at least 99% w/v or w/w of active ingredient(s).

If cells are genetically modified ex vivo, compositions can include greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$. In particular embodiments, compositions can be calibrated to provide 1 million-20 million genetically modified cells per kilogram when administered to a subject.

The compositions disclosed herein can be formulated for administration by, for example, injection, inhalation, infusion, perfusion, lavage or ingestion. The compositions can further be formulated for, for example, intravenous, intradermal, intraarterial, intranodal, intralymphatic, intraperitoneal, intralesional, intraprostatic, intravaginal, intrarectal, topical, intrathecal, intratumoral, intramuscular, intravesicular, oral and/or subcutaneous administration and more particularly by intravenous, intradermal, intraarterial, intranodal, intralymphatic, intraperitoneal, intralesional, intraprostatic, intravaginal, intrarectal, topical, intrathecal, intratumoral, intramuscular, intravesicular, oral and/or subcutaneous injection.

For injection, compositions can be formulated as aqueous solutions, such as in buffers including Hanks' solution, Ringer's solution, or physiological saline. The aqueous solutions can contain formulatory agents such as suspending, stabilizing and/or dispersing agents. Alternatively, the formulation can be in lyophilized and/or powder form for constitution with a suitable vehicle, e.g., sterile pyrogen-free water, before use.

For oral administration, the compositions can be formulated as tablets, pills, dragees, capsules, liquids, gels, syrups, slurries, suspensions and the like. For oral solid formulations such as, for example, powders, capsules and tablets, suitable excipients include binders (gum tragacanth, acacia, cornstarch, gelatin), fillers such as sugars, e.g. lactose, sucrose, mannitol and sorbitol; dicalcium phosphate, starch, magnesium stearate, sodium saccharine, cellulose, magnesium carbonate; cellulose preparations such as maize starch, wheat starch, rice starch, potato starch, gelatin, gum tragacanth, methyl cellulose, hydroxypropylmethyl-cellulose, sodium carboxy-methylcellulose, and/or polyvinylpyrrolidone (PVP); granulating agents; and binding agents. If desired, disintegrating agents can be added, such as corn starch, potato starch, alginic acid, cross-linked polyvinylpyrrolidone, agar, or alginic acid or a salt thereof such as sodium alginate. If desired, solid dosage forms can be sugar-coated or enteric-coated using standard techniques. Flavoring agents, such as peppermint, oil of wintergreen, cherry flavoring, orange flavoring, etc. can also be used.

For administration by inhalation, compositions can be formulated as aerosol sprays from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the therapeutic and a suitable powder base such as lactose or starch.

Any composition formulation disclosed herein can advantageously include any other pharmaceutically acceptable carriers which include those that do not produce significantly adverse, allergic or other untoward reactions that outweigh the benefit of administration, whether for research, prophylactic and/or therapeutic treatments. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety and purity standards as required by United States FDA Office of Biological Standards and/or other relevant foreign regulatory agencies.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants.

Exemplary buffering agents include citrate buffers, succinate buffers, tartrate buffers, fumarate buffers, gluconate buffers, oxalate buffers, lactate buffers, acetate buffers, phosphate buffers, histidine buffers and/or trimethylamine salts.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol and 3-pentanol.

Exemplary isotonic agents include polyhydric sugar alcohols including trihydric or higher sugar alcohols, such as glycerin, erythritol, arabitol, xylitol, sorbitol or mannitol.

Exemplary stabilizers include organic sugars, polyhydric sugar alcohols, polyethylene glycol; sulfur-containing reducing agents, amino acids, low molecular weight polypeptides, proteins, immunoglobulins, hydrophilic polymers or polysaccharides.

Compositions can also be formulated as depot preparations. Depot preparations can be formulated with suitable polymeric or hydrophobic materials (for example as an emulsion in an acceptable oil) or ion exchange resins, or as sparingly soluble derivatives, for example, as sparingly soluble salts.

Additionally, compositions can be formulated as sustained-release systems utilizing semipermeable matrices of solid polymers containing at least one active ingredient. Various sustained-release materials have been established and are well known by those of ordinary skill in the art. Sustained-release systems may, depending on their chemical nature, release active ingredients following administration for a few weeks up to over 100 days.

X. Kits. Combinations of active ingredients can also be provided as kits. Kits can include containers including one or more or more PN, NP, vaccine antigens, and/or vaccine adjuvants described herein formulated individually, or in various combinations. Generally, the kit will include PN, NP, vaccine antigens, and/or vaccine adjuvants specific to enhance vaccine efficacy against a particular infectious agent or cancer antigen, such as those described elsewhere herein.

Kits can also include a notice in the form prescribed by a governmental agency regulating the manufacture, use, or sale of pharmaceuticals or biological products, which notice reflects approval by the agency of manufacture, use, or sale for human administration. The notice may state that the provided active ingredients can be administered to a subject. The kits can include further instructions for using the kit, for example, instructions regarding preparation of PN, NP, vaccine antigens, and/or vaccine adjuvants for administration; proper disposal of related waste; and the like. The instructions can be in the form of printed instructions provided within the kit or the instructions can be printed on a portion of the kit itself. Instructions may be in the form of a sheet, pamphlet, brochure, CD-Rom, or computer-readable device, or can provide directions to instructions at a remote location, such as a website. In particular embodiments, kits can also include some or all of the necessary medical supplies needed to use the kit effectively, such as syringes, ampules, tubing, facemask, an injection cap, sponges, sterile adhesive strips, Chloraprep, gloves, and the like. Variations in contents of any of the kits described herein can be made. The instructions of the kit will direct use of the active ingredients to effectuate a new clinical use described herein.

XI. Methods of Use. Once formed, the compositions find use in a number of applications in subjects. Subjects include human subjects, veterinary animals (dogs, cats, reptiles, birds, etc. and also including animals found within zoos), livestock (horses, cattle, goats, pigs, chickens, etc.), and research animals (monkeys, rats, mice, fish, etc.). "Subjects in need thereof" include those in need of treatment, such as, those with a condition (e.g., an infection, cancer), as well as those prone to have or develop a condition (e.g., an infection, cancer), or those in whom a condition is to be prevented, such as those in a high risk group for exposure to a pathogen or cancer recurrence.

The skilled artisan will appreciate that the immune system produces an innate immune response and an adaptive immune response following a vaccination. An innate immune response generally can be characterized as not being substantially antigen specific and/or not generating immune memory. An adaptive immune response can be characterized as being substantially antigen specific, maturing over time (e.g., increasing affinity and/or avidity for antigen), and can produce immunologic memory. Even though these and other functional distinctions between innate and adaptive immunity can be discerned, the skilled artisan will appreciate that the innate and adaptive immune systems can be integrated and therefore can act in concert.

In particular embodiments, an adaptive immune response can be a "primary immune response" which refers to an immune response occurring on the first exposure of a "naive" subject to a vaccine antigen. For example, in the case of a primary antibody response, after a lag or latent period of from 3 to 14 days depending on, for example, the composition, dose, and subject, antibodies to the vaccine antigen can be produced. Generally, IgM production lasts for several days followed by IgG production and the IgM response can decrease. Antibody production can terminate after several weeks but memory cells can be produced. The primary immune response also triggers CD4+ and CD8+ T cell activation and proliferation. In particular embodiments, an adaptive immune response can be a "secondary immune response", "anamnestic response," or "booster response" which refer to the immune response occurring on a second and subsequent exposure of a subject to a vaccine antigen disclosed herein. Generally, in a secondary immune response, memory cells respond to the vaccine antigen and therefore the secondary immune response can differ from a primary immune response qualitatively and/or quantitatively. For example, in comparison to a primary immune response, the lag period of a secondary immune response can be shorter, the peak response can be higher, higher affinity antibodies and TCRs can be produced, and/or the response can persist for a greater period of time. In particular embodiments, "immune responses" can be measured by expansion, persistence, and/or activity of memory T cells (e.g., TCM and/or TEM).

In particular embodiments, improving the efficacy of a vaccination results in at least one of the following after administration of a therapeutically effective amount of a composition disclosed herein within a clinically relevant time window: in increased activation and/or proliferation of CD4+ and/or CD8+ T cells, increased production and retention of memory T cells (e.g., TCM and/or TEM), a shortened lag time before a secondary immune response, a higher peak response during a secondary immune response, and/or a greater persistence of a secondary immune response.

In particular embodiments, improving the efficacy of a vaccination results in at least one of the following after administration of a therapeutically effective amount of a composition disclosed herein within a clinically relevant time window: an improved prophylactic treatment and/or an improved therapeutic treatment.

Prophylactic treatments prevent or reduce the occurrence or severity of, or slow down or lessen the development of a potential disorder or disease. Prophylactic vaccine treatments increase the immunity of a subject against an infectious pathogen or type of cancer. Therefore, in particular embodiments, a vaccine may be administered prophylactically, for example to a subject that is immunologically naive (e.g., no prior exposure or experience with an infectious pathogen or cancer).

The compositions can be administered prophylactically in subjects who are at risk of developing a condition (e.g., an infection caused by HIV, malaria, herpes, chlamydia, EBV, Pneumococcus, and/or Hepatitis or cancer), or who have been exposed an agent leading to such an infection, to prevent, reduce, or delay the development of the infection or associated disease. For example, the compositions can be administered to a subject likely to have been exposed to HIV, malaria, herpes, chlamydia, EBV, Pneumococcus, and/or Hepatitis or to a subject who is at high risk for exposure to HIV, malaria, herpes, chlamydia, EBV, Pneumococcus, and/or Hepatitis or cancer recurrence.

Therapeutic treatments include reducing, eliminating, or slowing down the progression of an existing disorder or disease. In particular embodiments, a vaccine may be administered therapeutically to a subject who has been exposed to an infectious pathogen or cancer. Thus, a vaccine can be used to ameliorate a symptom associated with an infectious pathogen such as a reduced T cell count in the context of HIV infection and AIDS.

In particular embodiments, improving the efficacy of a vaccination provides an improved anti-infection effect. An anti-infection effect can reduce the number of cells that become infected, increase the time before cells become infected, prevent a higher level of infection, decrease the number of infected cells, decrease the volume of infected tissue, increase life expectancy, induce sensitivity of infected cells to immune clearance, reduce infection-associated pain, and/or prevent, reduce, delay, or eliminate a symptom associated with the treated infection.

In particular embodiments, improving the efficacy of a vaccination provides an improved anti-cancer effect. An anti-cancer effect can include a decrease in the occurrence of cancer cells, a decrease in the number of cancer cells, a decrease in the occurrence of metastases, a decrease in the number of metastases, a decrease in tumor volume, an increase in life expectancy, induced sensitivity of cancer cells to immune clearance, inhibited cancer cell proliferation, inhibited tumor growth, prolonged subject life, reduced cancer-associated pain, and/or reduced or delayed relapse or re-occurrence of cancer following treatment.

The actual dose of active ingredients administered to a particular subject can be determined by a physician, veterinarian, or researcher taking into account parameters such as physical and physiological factors including target, body weight, presence and/or severity of infection or cancer, stage of infection or cancer, previous or concurrent therapeutic interventions, idiopathy of the subject, and route of administration.

For administration, therapeutically effective amounts (also referred to herein as doses) can be initially estimated based on results from in vitro assays and/or animal model studies.

Exemplary doses of compositions include 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240 or 250 µg/kg body mass or mg/kg body mass although higher and/or lower doses can be used. The number of doses that can be administered as a function of time can be from 1, 2, 3, 4 or 5 doses over 1, 2, 3, 4, 5 or 6 weeks but can be increased or decreased depending at least in part on the immune status of a subject.

When genetically modified cells are administered as part of a composition, exemplary therapeutically effective amounts to administer can include greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$ cells. In particular embodiments, therapeutically effective amounts include 1 million-20 million cells per kilogram.

In particular embodiments, a composition can be administered initially, and thereafter maintained by further administration. For example, a composition can be administered by intramuscular injection. The subject's levels are then maintained by an oral dosage form, although other forms of administration, dependent upon the patient's condition, may be used. In the instance of a vaccine and NP composition, the composition may be administered as a single dose, or the composition may incorporate set booster doses. For example, booster doses may include variants of vaccine antigens and TCR to provide protection against multiple clades of infectious agents.

In particular embodiments, active ingredients for administration in one or more compositions can be (i) a PN and/or a PN within a NP, (ii) a vaccine antigen and (iii) a vaccine adjuvant. In particular embodiments, when included in combinations, the substituents in the combination can be provided in exemplary ratios such as: 1:1:1; 1:2:1; 1:3:1; 1:4:1; 1:5:1; 1:10:1; 1:2:2; 1:2:3; 1:3:4; 1:4:2; 1:5:3; 9:10:20; 5:2:1; 5:3:11; 5:4:1; 5:5:1; 5:100:1; 5:20:2; 5:2:3; 5:14:200; 5:10:20; or additional beneficial ratios depending on the number and identity of substituents in a combination to reach an intended effect. The substituents in a combination can be provided within the same composition or within different compositions, as will be understood by one of ordinary skill in the art.

Therapeutically effective amounts can be achieved by administering single or multiple doses during the course of a treatment regimen (e.g., QID, TID, BID, daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months, or yearly).

In particular embodiments, PN (in any of the various disclosed forms (e.g., naked or within NP) are administered within 1 month of vaccine antigen, within 3 weeks of vaccine antigen, within 2 weeks of vaccine antigen, within 1 week of vaccine antigen, within 7 days of vaccine antigen, within 6 days of vaccine antigen, within 5 days of vaccine antigen, within 4 days of vaccine antigen, within 3 days of vaccine antigen, within 2 days of vaccine antigen, within 24 hours of vaccine antigen, within 22 hours of vaccine antigen, within 20 hours of vaccine antigen, within 18 hours of vaccine antigen, within 16 hours of vaccine antigen, within 14 hours of vaccine antigen, within 12 hours of vaccine antigen, within 10 hours of vaccine antigen, within 8 hours of vaccine antigen, within 6 hours of vaccine antigen, within 4 hours of vaccine antigen, within 2 hours of vaccine antigen, or within 1 hours of vaccine antigen. "Within"

includes before or after vaccine administration, and each of these times can provide a clinically relevant time window.

In particular embodiments, enhanced vaccine efficacy decreases a subject's development of a condition. Conditions can be evaluated through clinical endpoints such as blood tests, evaluation of biopsy samples, and symptoms of conditions as fever, chills, rash, joint pain, nausea, vomiting, red eyes, cancer recurrence, etc.

Unless otherwise indicated, the practice of the present disclosure can employ conventional techniques of immunology, molecular biology, microbiology, cell biology and recombinant DNA. These methods are described in the following publications. See, e.g., Sambrook, et al. Molecular Cloning: A Laboratory Manual, $2^{nd}$ Edition (1989); F. M. Ausubel, et al. eds., Current Protocols in Molecular Biology, (1987); the series Methods IN Enzymology (Academic Press, Inc.); M. MacPherson, et al., PCR: A Practical Approach, IRL Press at Oxford University Press (1991); MacPherson et al., eds. PCR 2: Practical Approach, (1995); Harlow and Lane, eds. Antibodies, A Laboratory Manual, (1988); and R. I. Freshney, ed. Animal Cell Culture (1987).

Sequence information provided by public database can be used to identify additional gene and protein sequences that can be used with the systems and methods disclosed herein.

Variants of the sequences disclosed and referenced herein are also included. Variants of proteins can include those having one or more conservative amino acid substitutions. As used herein, a "conservative substitution" involves a substitution found in one of the following conservative substitutions groups: Group 1: Alanine (Ala), Glycine (Gly), Serine (Ser), Threonine (Thr); Group 2: Aspartic acid (Asp), Glutamic acid (Glu); Group 3: Asparagine (Asn), Glutamine (Gln); Group 4: Arginine (Arg), Lysine (Lys), Histidine (His); Group 5: Isoleucine (Ile), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys); acidic: Asp, Glu, Asn, and Gin; small aliphatic, nonpolar or slightly polar residues: Ala, Ser, Thr, Pro, and Gly; polar, negatively charged residues and their amides: Asp, Asn, Glu, and Gin; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

As indicated elsewhere, variants of gene sequences can include codon optimized variants, sequence polymorphisms, splice variants, and/or mutations that do not affect the function of an encoded product to a statistically-significant degree.

Variants of the protein, nucleic acid, and gene sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

The Exemplary Embodiments and Examples below are included to demonstrate particular embodiments of the disclosure. Those of ordinary skill in the art should recognize in light of the present disclosure that many changes can be made to the particular embodiments disclosed herein and still obtain a like or similar result without departing from the spirit and scope of the disclosure.

Exemplary Embodiments

1. A method of vaccinating a subject including: administering a therapeutically effective amount of a polynucleotide encoding a T cell receptor (TCR) to a subject wherein the encoded TCR specifically binds a vaccine antigen administered to the subject within a clinically relevant time window of the administering, thereby vaccinating the subject.

2. A method of embodiment 1 wherein the administering improves the efficacy of the vaccination as compared to administration of the vaccine antigen alone.

3. A method of embodiment 1 or 2 wherein the subject is in need of improved vaccine efficacy due to age or immune status.

4. A method of embodiment 3 wherein the immune status includes a low T cell count.

5. A method of any of embodiments 1-4 wherein the vaccinating provides a treatment for AIDS, malaria, herpes, chlamydia, Epstein-Barr virus, Pneumococcus, or Hepatitis B.

6. A method of any of embodiments 1-5 wherein the TCR is Class I restricted.

7. A method of any of embodiments 1-5 wherein the TCR is Class II restricted

8. A method of embodiment 6 wherein the TCR is Class I restricted and the improved vaccine efficacy is due to CD8+T helper cell activity that improves a T cell cytotoxic response.

9. A method of embodiment 7 wherein the TCR is Class II restricted and the improved vaccine efficacy is due to CD4+T helper cell activity that improves a B cell antibody response.

10. A method of any of embodiments 1-9 wherein the TCR includes the variable regions of an α chain and a β chain.

11. A method of any of embodiments 1-10 wherein the TCR includes the constant regions of an α chain and a β chain.

12. A method of any of embodiments 1-11 wherein the TCR includes a transmembrane domain and a cytoplasmic tail.

13. A method of any of embodiments 1-12 wherein the TCR includes an α chain selected from SEQ ID NOs: 1, 4, 18, 21, 23, 25, 27, 29-32, 34, and 36.

14. A method of any of embodiments 1-13 wherein the TCR includes an β chain selected from SEQ ID NOs: 2, 3, 19, 22, 24, 26, 28, 33, 35, and 37.

15. A method of any of embodiments 1-12 wherein the TCR includes sequences selected from SEQ ID NOs: 5-12, 15, 16, and 39.

16. A method of any of embodiments 1-15 wherein the vaccine antigen includes a viral antigen.

17. A method of embodiment 16 wherein the viral antigen is derived from an adenovirus, arenavirus, bunyavirus, coronavirus, flavirvirus, hantavirus, hepadnavirus, herpesvirus, papilomavirus, paramyxovirus, parvovirus, picornavirus, poxvirus, orthomyxovirus, retrovirus, reovirus, rhabdovirus, rotavirus, spongiform virus or togavirus.

18. A method of embodiment 16 or 17 wherein the viral antigen includes a peptide expressed by cytomegalovirus, cold virus, Epstein-Barr virus, flu virus, hepatitis A, B, or C virus, herpes simplex virus, human immunodeficiency virus, influenza virus, Japanese encephalitis virus, measles virus, polio virus, rabies virus, respiratory syncytial virus, rubella virus, smallpox virus, varicella zoster virus, West Nile virus, or Zika virus.

19. A method of any of embodiments 16-18 wherein the viral antigen includes a cytomegaloviral antigen selected from envelope glycoprotein B and/or CMV pp65; an Epstein-Barr antigen selected from EBV EBNAI, EBV P18, and/or EBV P23; a hepatitis vaccine antigen selected from the S, M, and/or L proteins or the pre-S antigen of hepatitis B virus; a herpes simplex vaccine antigen selected from glycoprotein D; a human immunodeficiency virus (HIV) vaccine antigen selected from HIV gp32, HIV gp41, HIV gp120, HIV gp160, HIV P17/24, HIV P24, HIV P55 GAG, HIV P66 POL, HIV TAT, HIV GP36, the Nef protein and/or HIV reverse transcriptase; a human papillomavirus virus (HPV) viral antigen selected from the L1 protein; an influenza vaccine antigen selected from hemagglutinin and neuraminidase; a Japanese encephalitis vaccine antigen selected from proteins E, M-E, M-E-NS1, NS1, or NS1-NS2A; a malaria vaccine antigen selected from circumsporozoite (CSP), glutamate dehydrogenase, lactate dehydrogenase, or fructose-bisphosphate aldolase; a measles vaccine antigen selected from measles virus fusion protein; a rabies vaccine antigen selected from rabies glycoprotein or rabies nucleoprotein; a respiratory syncytial vaccine antigen selected from RSV fusion protein or M2 protein; a rotaviral vaccine antigen selected from VP7sc; a rubella vaccine antigen selected from protein E1 or E2; a varicella zoster vaccine antigen selected from gpl or gpll; or a zika vaccine antigen selected from pre-membrane, envelope (E), Domain III of the E protein, or non-structural proteins 1, 2, 3, 4, or 5.

20. A method of any of embodiments 16-18 wherein the viral antigen is selected from Nef (66-97), Nef (116-145), Gag p17 (17-35), Gag p17-p24 (253-284), Pol 325-355 (RT 158-188), CSP central repeat region, or E protein Domain III.

21. A method of any of embodiments 16-20 wherein the viral antigen includes any one of SEQ ID NOs: 128-134.

22. A method of any of embodiments 1-15 wherein the vaccine antigen includes a cancer antigen.

23. A method of embodiment 22 wherein the cancer antigen includes A33; BAGE; Bcl-2; β-catenin; CA125; CA19-9; CD5; CD19; CD20; CD21; CD22; CD33; CD37; CD45; CD123; CEA; c-Met; CS-1; cyclin B1; DAGE; EBNA; EGFR; ephrinB2; estrogen receptor; FAP; ferritin; folate-binding protein; GAGE; G250; GD-2; GM2; gp75, gp100 (Pmel 17); HER-2/neu; HPV E6; HPV E7; Ki-67; LRP; mesothelin, p53, PRAME; progesterone receptor; PSA; PSMA; MAGE; MART; mesothelin; MUC; MUM-1-B; myc; NYESO-1; ras; RORI; survivin; tenascin; TSTA tyrosinase; VEGF; or WT1.

24. A method of embodiment 22 or 23 wherein the cancer antigen includes PSMA, PSCA, mesothelin, CD19, CD20, ROR1, or WT1.

25. A method of any of embodiments 22-24 wherein the cancer antigen includes any one of SEQ ID NOs: 135-141.

26. A method of any of embodiments 1-25 further including administering a vaccine adjuvant.

27. A method of embodiment 26 wherein the vaccine adjuvant includes (i) a Toll-like receptor ligand selected from CpG, Cpg-28, Poly(I:C), α-galactoceramide, MPLA, VTX-2337, EMD1201081) imiquimod, MGN1703, G100, CBLB502, Hiltonol, and imiquimod, and/or (ii) 17-dimethylaminoethylamino-17-demethoxygeldanamycin).

28. A method of embodiment 26 wherein the vaccine adjuvant includes a STING agonist.

29. A method of embodiment 28 wherein the STING agonist includes c-diGMP, c-diAMP, c-GAMP, c-AIMP, (3',2')c-AIMP, (2',2')c-AIMP, (2',3')c-AIMP, c-AIMP(S), c-(dAMP-dIMP), c-(dAMP-2'FdIMP), c-(2'FdAMP-2'FdIMP), (2',3') c-(AMP-2'FdIMP), c-[2'FdAM P(S)-2'FdIMP(S)], c-[2'FdAMP(S)-2'FdIMP(S)](POM)$^2$, and/or DMXAA.

30. A method of any of embodiments 1-29 wherein the polynucleotide includes a plasmid, a minicircle plasmid, or a self-replicating mRNA molecule.

31. A method of any of embodiments 1-30 wherein the administering includes via intramuscular injection.

32. A method of any of embodiments 1-31 wherein the polynucleotide is within a nanoparticle.

33. A method of embodiment 32 wherein the nanoparticle includes liposomes, polymeric particles, metallic particles, polymeric micelles, polyethyleneimine (PEI)/DNA complexes, or a combination thereof.

34. A method of embodiment 32 or 33 wherein the nanoparticle includes a poly(β-amino ester) polymer.

35. A method of any of embodiments 32-34 wherein the nanoparticle includes a lipid coating.

36. A method of embodiment 35 wherein the lipid coating includes a liposome, a lipid bilayer, or a polymeric micelle.

37. A method of any of embodiments 32-36 wherein the nanoparticle includes poly(β-amino ester) with a PGA coating.

38. A method of any of embodiments 32-37 wherein the nanoparticle includes a T cell targeting and delivery agent (T-DA).

39. A method of embodiment 38 wherein the T-DA includes a binding domain that selectively binds to T cells in vivo.

40. A method of embodiment 38 wherein the T-DA includes a binding domain that selectively binds a T cell receptor motif; a T cell α chain; a T cell β chain; CCR7; CD3; CD4; CD8; CD28; CD45RA; CD62L; CD127; or LFA-1.

41. A method of embodiment 40 wherein the T-DA binding domain selectively binds CD4.

42. A method of embodiment 41 wherein the T-DA binding domain includes any one of SEQ ID NOs: 41-46.

43. A method of embodiment 40 wherein the T-DA binding domain selectively binds CD8.

44. A method of embodiment 43 wherein the T-DA binding domain includes any one of SEQ ID NOs: 47-52.

45. A method of embodiment 40 wherein the T-DA binding domain selectively binds CD3.

46. A method of embodiment 45 wherein the T-DA binding domain includes any one of SEQ ID NOs: 53-58.

47. A method of any of embodiments 38-40 wherein the T-DA includes a binding domain that selectively binds CD4+ or CD8+ T cells in vivo and ex vivo.

48. A method of any of embodiments 39-47 wherein the T-DA binding domain includes a T cell receptor motif antibody; a T cell α chain antibody; a T cell β chain antibody; a CCR7 antibody; a CD3 antibody; a CD4 antibody; a CD8 antibody; a CD28 antibody; a CD45RA antibody; a CD62L antibody; a CD127 antibody; a LFA-1 antibody; or an effective fragment of the foregoing antibodies.

49. A method of any of embodiments 32-48 wherein the nanoparticle includes an endosomal release agent (ERA).

50. A method of embodiment 49 wherein the ERA includes any one of SEQ ID NOs: 40, and 59-80, or combinations thereof.

51. A method of any of embodiments 32-50 wherein the nanoparticle includes a nuclear targeting agent (NTA).

52. A method of embodiment 51 wherein the NTA includes any one of SEQ ID NOs: 81-127, or combinations thereof.

53. A method of any of embodiments 32-52 wherein the nanoparticle includes an iPB7 transposase, a S/MAR element, a PiggyBac transposase-containing plasmid, a Sleeping Beauty transposase-containing plasmid; a *Homo sapiens* transposon-derived Buster1 transposase-like protein gene; a human endogenous retrovirus H protease/integrase-derived ORF1; a *Homo sapiens* Cas-Br-M (murine) ecotropic retroviral transforming sequence; a *Homo sapiens* endogenous retroviral sequence K; a *Homo sapiens* endogenous retroviral family W sequence; a *Homo sapiens* LINE-1 type transposase domain; or a *Homo sapiens* pogo transposable element.

54. A method of embodiment 53 wherein the iBP7 transposase includes SEQ ID NO: 142.

55. A method of any of embodiments 1-54 wherein the administering results in expression of the polynucleotide selectively by T cells within 10 days; within 9 days; within 8 days; within 7 days; within 6 days; within 5 days; within 4 days; or within 3 days of administration.

56. A kit including a vaccine antigen and a polynucleotide (PN) encoding a T cell receptor (TCR) that binds the vaccine antigen when expressed by a T cell.

57. A kit of embodiment 56 wherein the TCR is Class I restricted.

58. A kit of embodiment 56 wherein the TCR is Class II restricted.

59. A kit of any of embodiments 56-58 wherein the TCR includes the variable regions of an α chain and a β chain.

60. A kit of any of embodiments 56-59 wherein the TCR includes the constant regions of an α chain and a β chain.

61. A kit of any of embodiments 56-60 wherein the TCR includes a transmembrane domain and a cytoplasmic tail.

62. A kit of any of embodiments 56-61 wherein the TCR includes an α chain including SEQ ID NOs: 1, 4, 18, 21, 23, 25, 27, 2932, 34, and 36.

63. A kit of any of embodiments 56-62 wherein the TCR includes an β chain including SEQ ID NOs: 2, 3, 19, 22, 24, 26, 28, 33, 35, and 37.

64. A kit of any of embodiments 56-61 wherein the TCR includes SEQ ID NOs: 5-12, 15, 16, and 39.

65. A kit of any of embodiments 56-64 wherein the vaccine antigen includes a viral antigen.

66. A kit of embodiment 65 wherein the viral antigen is derived from an adenovirus, arenavirus, bunyavirus, coronavirus, flavirvirus, hantavirus, hepadnavirus, herpesvirus, papilomavirus, paramyxovirus, parvovirus, picornavirus, poxvirus, orthomyxovirus, retrovirus, reovirus, rhabdovirus, rotavirus, spongiform virus or togavirus.

67. A kit of embodiment 65 wherein the viral antigen includes a peptide expressed by cytomegalovirus, cold virus, Epstein-Barr virus, flu virus, hepatitis A, B, or C virus, herpes simplex virus, human immunodeficiency virus, influenza virus, Japanese encephalitis virus, measles virus, polio virus, rabies virus, respiratory syncytial virus, rubella virus, smallpox virus, varicella zoster virus, West Nile virus, or Zika virus.

68. A kit of any of embodiments 65-67 wherein the viral antigen includes a cytomegaloviral antigen selected from envelope glycoprotein B and/or CMV pp65; an Epstein-Barr antigen selected from EBV EBNAI, EBV P18, and/or EBV P23; a hepatitis vaccine antigen selected from the S, M, and/or L proteins or the pre-S antigen of hepatitis B virus; a herpes simplex vaccine antigen selected from glycoprotein D; a human immunodeficiency virus (HIV) vaccine antigen selected from HIV gp32, HIV gp41, HIV gp120, HIV gp160, HIV P17/24, HIV P24, HIV P55 GAG, HIV P66 POL, HIV TAT, HIV GP36, the Nef protein and/or HIV reverse transcriptase; a human papillomavirus virus (HPV) viral antigen selected from the L1 protein; an influenza vaccine antigen selected from hemagglutinin and neuraminidase; a Japanese encephalitis vaccine antigen selected from proteins E, M-E, M-E-NS1, NS1, or NS1-NS2A; a malaria vaccine antigen selected from circumsporozoite (CSP), glutamate dehydrogenase, lactate dehydrogenase, or fructose-bisphosphate aldolase; a measles vaccine antigen selected from measles virus fusion protein; a rabies vaccine antigen selected from rabies glycoprotein or rabies nucleoprotein; a respiratory syncytial vaccine antigen selected from RSV fusion protein or M2 protein; a rotaviral vaccine antigen selected from VP7sc; a rubella vaccine antigen selected from protein E1 or E2; a varicella zoster vaccine antigen selected from gpl or gpll; or a zika vaccine antigen selected from pre-membrane, envelope (E), Domain III of the E protein, or non-structural proteins 1, 2, 3, 4, or 5.

69. A kit of any of embodiments 65-68 wherein the viral antigen includes Nef (66-97), Nef (116-145), Gag p17 (17-35), Gag p17-p24 (253-284), Pol 325-355 (RT 158-188), CSP central repeat region, or E protein Domain III.

70. A kit of any of embodiments 65-69 wherein the viral antigen includes any of SEQ ID NOs: 128-134.
71. A kit of any of embodiments 56-70 wherein the vaccine antigen includes a cancer antigen.
72. A kit of embodiment 71 wherein the cancer antigen includes A33; BAGE; Bcl-2; β-catenin; CA125; CA19-9; CD5; CD19; CD20; CD21; CD22; CD33; CD37; CD45; CD123; CEA; c-Met; CS-1; cyclin B1; DAGE; EBNA; EGFR; ephrinB2; estrogen receptor; FAP; ferritin; folate-binding protein; GAGE; G250; GD-2; GM2; gp75, gp100 (Pmel 17); HER-2/neu; HPV E6; HPV E7; Ki-67; LRP; mesothelin, p53, PRAME; progesterone receptor; PSA; PSMA; MAGE; MART; mesothelin; MUC; MUM-1-B; myc; NYESO-1; ras; ROR1; survivin; tenascin; TSTA tyrosinase; VEGF; or WT1.
73. A kit of embodiment 71 or 72 wherein the cancer antigen includes PSMA, PSCA, mesothelin, CD19, CD20, ROR1, or WT1.
74. A kit of embodiment 73 wherein the cancer antigen includes any one of SEQ ID NOs: 135-141.
75. A kit of any of embodiments 56-74 further including administering a vaccine adjuvant.
76. A kit of embodiment 75 wherein the vaccine adjuvant includes a STING agonist.
77. A kit of any of embodiments 56-76 wherein the polynucleotide includes a plasmid, a minicircle plasmid, or a self-replicating mRNA molecule.
78. A kit of any of embodiments 56-77 wherein the polynucleotide is within a nanoparticle.
79. A kit of embodiment 78 wherein the nanoparticle includes liposomes, polymeric particles, metallic particles, polymeric micelles, polyethyleneimine (PEI)/DNA complexes, or a combination thereof.
80. A kit of embodiment 78 wherein the nanoparticle includes a poly(β-amino ester) polymer.
81. A kit of any of embodiments 78-80 wherein the nanoparticle includes a lipid coating.
82. A kit of embodiment 81 wherein the lipid coating includes a liposome, a lipid bilayer, or a polymeric micelle.
83. A kit of any of embodiments 78-82 wherein the nanoparticle includes a poly(β-amino ester) polymer with a PGA coating.
84. A kit of any of embodiments 78-83 wherein the nanoparticle includes a T cell targeting and delivery agent (T-DA).
85. A kit of embodiment 84 wherein the T-DA includes a binding domain that selectively binds a T cell receptor motif; a T cell α chain; a T cell 3 chain; CCR7; CD3; CD4; CD8; CD28; CD45RA; CD62L; CD127; or LFA-1.
86. A kit of embodiment 85 wherein the T-DA binding domain selectively binds CD4.
87. A kit of embodiment 86 wherein the T-DA binding domain includes any one of SEQ ID NOs: 41-46.
88. A kit of embodiment 85 wherein the T-DA binding domain selectively binds CD8.
89. A kit of embodiment 88 wherein the T-DA binding domain includes any one of SEQ ID NOs: 47-52.
90. A kit of embodiment 85 wherein the T-DA binding domain selectively binds CD3.
91. A kit of embodiment 90 wherein the T-DA binding domain includes any one of SEQ ID NOs: 53-58.
92. A kit of embodiment 84 or 85 wherein the T-DA includes a binding domain that selectively binds CD4+ or CD8+ T cells in vivo and ex vivo.
93. A kit of any of embodiments 85-92 wherein the T-DA binding domain includes a T cell receptor motif antibody; a T cell α chain antibody; a T cell 3 chain antibody; a CCR7 antibody; a CD3 antibody; a CD4 antibody; a CD8 antibody; a CD28 antibody; a CD45RA antibody; a CD62L antibody; a CD127 antibody; a LFA-1 antibody; or an effective fragment of the foregoing antibodies.
94. A kit of any of embodiments 56-93 wherein the nanoparticle includes an endosomal release agent (ERA).
95. A kit of embodiment 94 wherein the ERA includes any one of SEQ ID NOs: 40, and 59-80, or combinations thereof.
96. A kit of any of embodiments 56-95 wherein the nanoparticle includes a nuclear targeting agent (NTA).
97. A kit of embodiment 96 wherein the NTA includes any one of SEQ ID NOs: 81-127, or combinations thereof.
98. A kit of any of embodiments 56-97 wherein the nanoparticle includes an iPB7 transposase, a S/MAR element, a PiggyBac transposase-containing plasmid, a Sleeping Beauty transposase-containing plasmid; a Homo sapiens transposon-derived Buster1 transposase-like protein gene; a human endogenous retrovirus H protease/integrase-derived ORF1; a Homo sapiens Cas-Br-M (murine) ecotropic retroviral transforming sequence; a Homo sapiens endogenous retroviral sequence K; a Homo sapiens endogenous retroviral family W sequence; a Homo sapiens LINE-1 type transposase domain; or a Homo sapiens pogo transposable element.
99. A kit of embodiment 98 wherein the iBP7 transposase includes SEQ ID NO: 142.
100. Use of a method or kit of any of embodiments 1-99 to provide vaccine antigen recognizing capabilities to the T cells of a subject.
101. Use of a method or kit of any of embodiments 1-99 to render a subject's immune system responsive to a vaccine antigen.
102. Use of a method or kit of any of embodiments 1-99 to increase a subject's immune system response to a vaccine antigen.

Figure 3A:
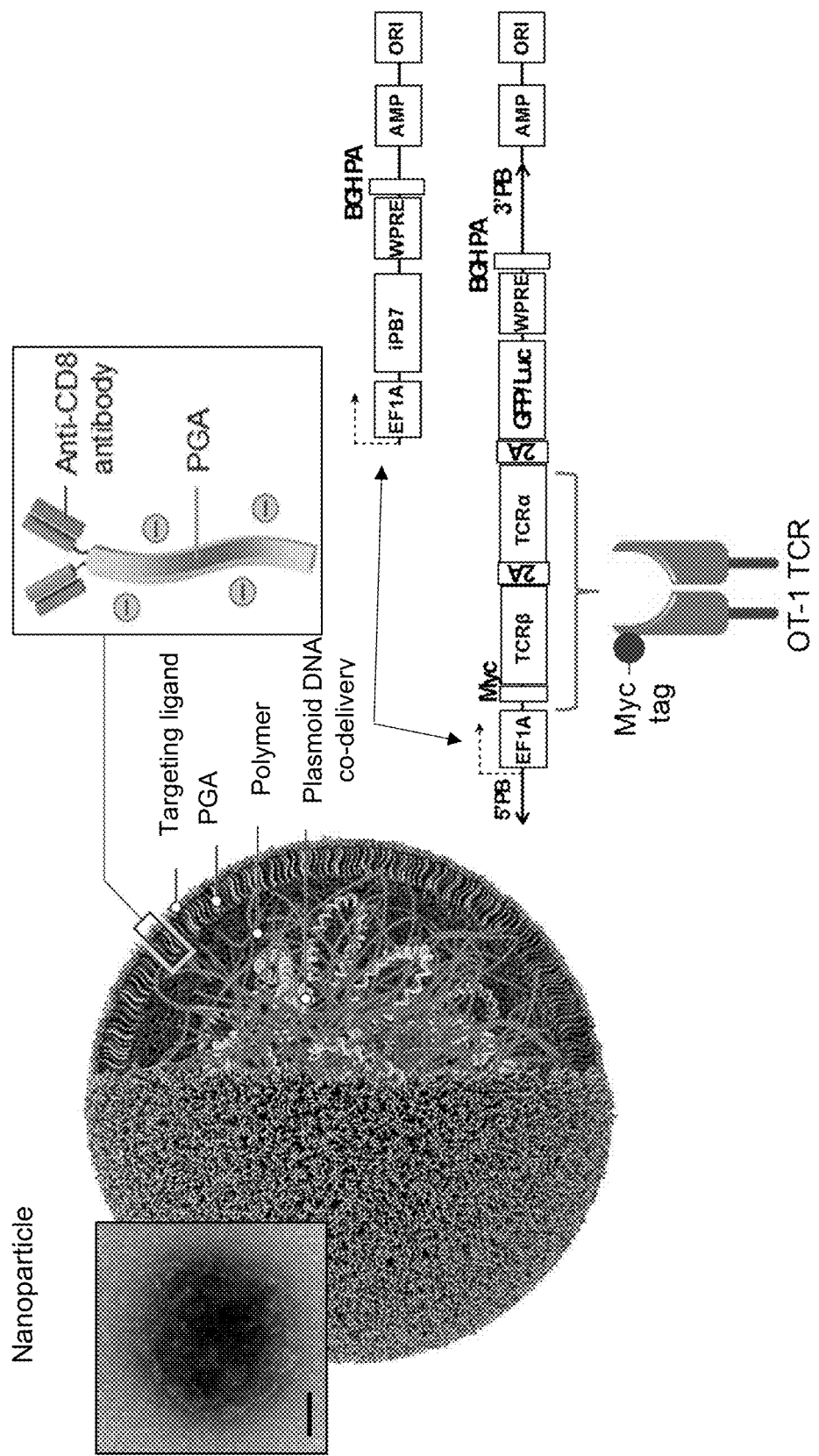
Figure 3C:
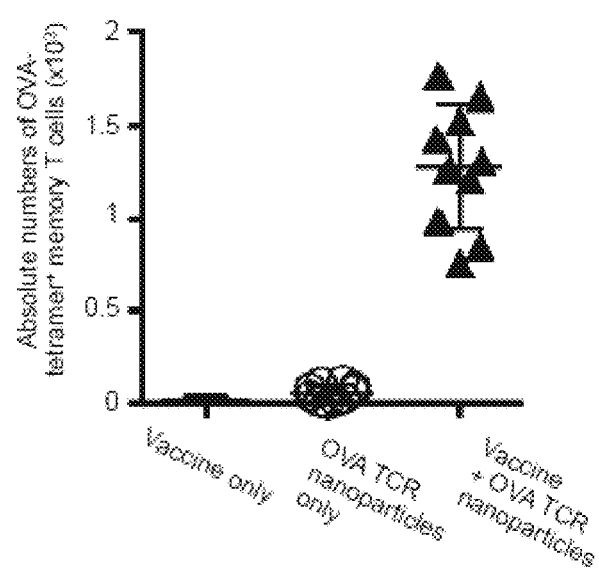

Examples. The impact of many vaccines can be enhanced if they are co-delivered with agents that program T cells to produce TCRs that react with the vaccine antigens. This premise was tested by loading CD8-targeted nanoparticles (NP) with plasmids encoding the ovalbumin (OVA)-specific OT-1 TCR (FIG. 3A). The design of these DNA-carrying NPs was based on versions developed to program tumor recognition abilities into circulating lymphocytes—in those studies, it was demonstrated that when the NPs were outfitted with lymphocyte-targeting ligands, chimeric antigen receptor genes are transfected into host T cells. This NP platform was adapted to program host T cells so they express vaccine-specific TCRs. P14 TCR-transgenic mice (containing only CD8 T cells specific for Lymphocytic Choriomeningitis Virus) were intramuscularly injected with a single dose of $10^{11}$ T cell-targeted NPs delivering genes that encode the OVA-specific OT-1 TCR, along with a myc-tag and the hyperactive iPB7 transposase. These NPs were either injected alone or in combination with an OVA peptide vaccine. As controls, mice were immunized with the OVA vaccine only, or left untreated. On days 7 and 30 after the immunizations, draining lymph nodes were isolated so the percentages of NP-programmed (OVA-tetramer+) T cells could be quantified by flow cytometry. It was found that intramuscularly injected NPs effectively deliver engineered TCR genes into host T cells so that they recognize the vaccine antigen (FIG. 3B). Following their rapid vaccine-induced expansion, the NP-programmed T cells differentiate into long-lived memory T cells (FIGS. 3B, 3C).

Figure 4A:
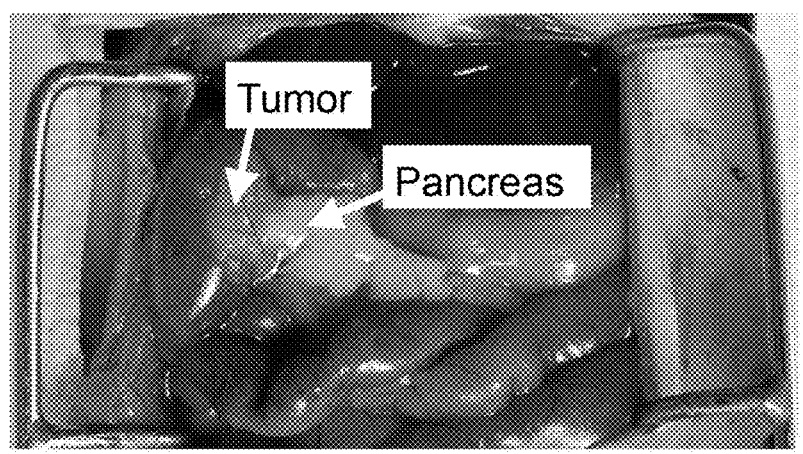
FIGS. 4A, 4B. Combining T cell-targeted NPs encoding $TCR_{1045}$ with mesothelin (MSLN) vaccines significantly prolongs survival of $Kras^{LSL-G12D/+}$; $Trp53^{LSL-R172H/+}$; $p48^{Cre/+}$ (KPC) mice with established pancreatic ductal adenocarcinoma. (4A) Example tumor mass in the pancreas of a 4-month-old KPC mouse. (4B) Survival of KPC mice receiving either T cell-targeted NPs encoding the $TCR_{1045}$, the MSLN vaccine, or both. Controls received no treatment. ms=mean survival.
Figure 4B:
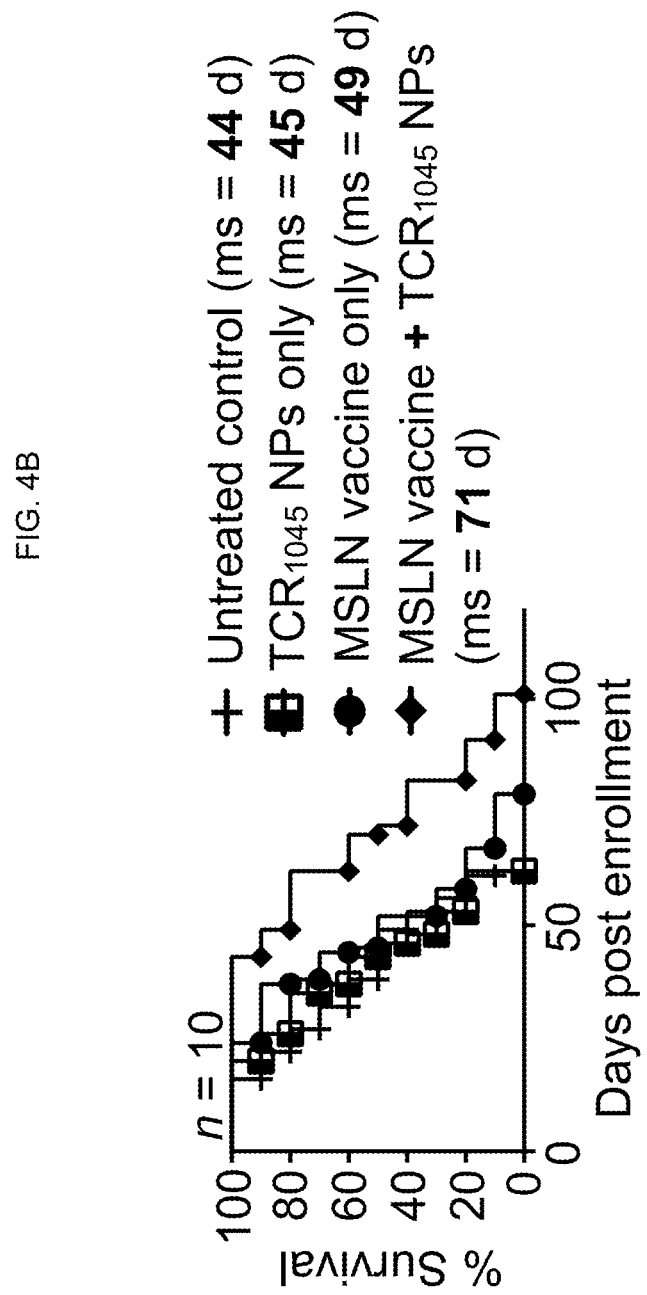

The Kras$^{LSL-G12D/+}$; Trp53$^{LSL-R172H/+}$; p48$^{Cre/+}$ (KPC) mouse model was utilized to test the NP vaccine strategy in a clinically relevant in vivo test system. The KPC model expresses mutant Kras and p53 at endogenous gene loci known to drive pancreatic tumorigenesis. This model recapitulates the cardinal features of human pancreatic ductal adenocarcinoma (PDA), including molecular progression, histopathology, and clinical syndrome (FIG. 4A). KPC mice carrying a defined tumor burden (2-5 mm diameter, as determined by high-resolution ultrasound) were intramuscularly injected with a single dose of $10^{13}$ T cell-targeted NPs delivering genes that encode the tumor antigen mesothelin (MSLN)-specific receptor $TCR_{1045}$ (Stromnes, I M et al. (2015) supra), along with a myc-tag and the hyperactive iPB7 transposase (to ensure efficient integration of the vector into chromosomes via a "cut and paste" mechanism). In particular embodiments, the hyperactive iPB7 transposase is a murine codon-optimized piggyBac transposase cDNA (GenBank accession number: EF587698, Cadiñanos, J and Bradley, A (2007) Nucleic Acids Res 35: e87, see FIG. 6, SEQ ID NO: 142). These NPs were either injected alone or in combination with an MSLN vaccine ($5 \times 10^8$ pfu of an attenuated recombinant adenovirus expressing murine MSLN). As controls, mice were immunized with the MSLN vaccine only, were not treated. Only animals treated with a combination of both the $TCR_{1045}$ NPs and the MSLN vaccine exhibited tumor regression; they also had an average 27-day improvement in survival (FIG. 4B).

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically-significant reduction in the ability to increase a subject's immune system response to a vaccine antigen within 7 days of vaccine administration.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Particular embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3$^{rd}$ Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A method, comprising
   administering a vaccine antigen to a subject; and
   administering an effective amount of a nanoparticle to the subject; wherein the nanoparticle comprises
   (i) a polynucleotide encoding a T cell receptor (TCR) that specifically binds the vaccine antigen; and
   (ii) a binding fragment of an anti-CD4 or anti-CD8 antibody exposed on the surface of the nanoparticle.

2. The method of claim 1, wherein the vaccine antigen comprises a cancer antigen selected from prostate-specific membrane antigen (PSMA), prostate stem cell antigen (PSCA), mesothelin, CD19, CD20, receptor tyrosine kinase-like orphan receptor 1 (ROR1), and Wilms' tumor protein 1 (WT1) or a fragment of PSMA, PSCA, mesothelin, CD19, CD20, ROR1, and WT1 or a viral antigen selected from Nef (66-97), Nef (116-145), Gag p17 (17-35), Gag p17-p24 (253-284), Pol 325-355 (RT 158-188), circumsporozoite protein (CSP) central repeat region, and E protein Domain III.

3. The method of claim 1, wherein the vaccine antigen comprises a cancer antigen selected from SEQ ID NOs. 135-141 or a viral antigen selected from SEQ ID NOs: 128-134.

4. The method of claim 1, wherein the encoded TCR comprises an α chain selected from SEQ ID NOs: 1, 4, 18, 21, 23, 25, 27, 29-32, 34, and 36.

5. The method of claim 1, wherein the encoded TCR comprises a β chain selected from SEQ ID NOs: 2, 3, 19, 22, 24, 26, 28, 33, 35, and 37.

6. The method of claim 1, wherein the encoded TCR comprises a sequence selected from SEQ ID NOs: 5-12, 15, 16, and 39.

7. The method of claim 1, comprising administering an adjuvant.

8. The method of claim 7, wherein the vaccine adjuvant is selected from CpG, Cpg-28, Polyriboinosinic polyribocytidylic acid (Poly(I:C)), α-galactoceramide, monophosphoryl lipid A (MPLA), a toll-like receptor agonist, Amino-1-isobutyl-1H-imidazo(4,5-c)quinoline, polyinosinic-polycytidylic acid stabilized with polylysine and carboxymethylcellulose, and 17-dimethylaminoethylamino-17-demethoxygeldanamycin, and/or a stimulator of interferon genes (STING) agonist selected from c-diGMP, c-di-AMP, c-GAMP, c-AIMP, (3',2')c-AIMP, (2',2')c-AIMP, (2',3')c-AIMP, c-AIMP(S), c-(dAMP-dIMP), c-(dAMP-2'FdIMP), c-(2'FdAMP-2'FdIMP), (2',3')c-(AMP-2'FdIMP), c-[2'FdAMP(S)-2'FdIMP(S)], c-[2'FdAMP(S)-2'FdIMP(S)](POM)$^2$, and/or dimethylxanthone acetic acid (DMXAA).

9. The method of claim 1, wherein the polynucleotide is encapsulated within a positively-charged polymer matrix.

10. The method of claim 9, wherein the positively-charged polymer matrix comprises poly-β-amino ester (PBAE).

11. The method of claim 9, wherein the positively-charged polymer matrix is surrounded by a negatively-charged coating.

12. The method of claim 11, wherein the negatively-charged coating comprises polyglutamic acid (PGA).

13. The method of claim 1, wherein the binding fragment comprises a sequence selected from SEQ ID NOs: 41-58.

14. The method of claim 1, wherein the nanoparticle comprises an iPB7 transposase comprising SEQ ID NO: 142.

15. The method of claim 1, wherein the subject has a low T cell count.

16. The method of claim 1, wherein the method improves the efficacy of the vaccination as compared to administration of the vaccine antigen alone.

17. A kit for practicing the method of claim 1 comprising:
a vaccine antigen;
a positively-charged polymer;

a negatively-charged polymer covalently linked to a binding fragment of an anti-CD4 or anti-CD8 antibody; and a polynucleotide encoding a T cell receptor (TCR) that specifically binds the vaccine antigen.

18. The kit of claim 17, wherein the vaccine antigen comprises a cancer antigen selected from prostate-specific membrane antigen (PSMA), prostate stem cell antigen (PSCA), mesothelin, CD19, CD20), receptor tyrosine kinase-like orphan receptor 1 (ROR1), and Wilms' tumor gene 1 (WT1) or a fragment of PSMA, PSCA, mesothelin, CD19, CD20, ROR1, and WT1 or a viral antigen selected from Nef (66-97), Nef (116-145), Gag p17 (17-35), Gag p17-p24 (253-284), Pol 325-355 (RT 158-188), circumsporozoite protein (CSP) central repeat region, and E protein Domain III.

19. A composition, comprising:

a vaccine antigen; and an effective amount of a nanoparticle, wherein the nanoparticle comprises (i) a polynucleotide encoding a T cell receptor (TCR) that specifically binds the vaccine antigen; and (ii) a binding fragment of an anti-CD4 or anti-CD8 antibody exposed on the surface of the nanoparticle.

20. The composition of claim 19, wherein the vaccine antigen comprises a cancer antigen selected from prostate-specific membrane antigen (PSMA), prostate stem cell antigen (PSCA), mesothelin, CD19, CD20, receptor tyrosine kinase-like orphan receptor 1 (ROR1), and Wilms' tumor gene 1 (WT1) or a fragment of PSMA, PSCA, mesothelin, CD19, CD20, ROR1, and WT1 or a viral antigen selected from Nef (66-97), Nef (116-145), Gag p17 (17-35), Gag p17-p24 (253-284), Pol 325-355 (RT 158-188), circumsporozoite protein (CSP) central repeat region, and E protein Domain III.

21. The composition of claim 19, comprising an adjuvant.

22. The composition of claim 19, wherein the polynucleotide is encapsulated within a positively-charged polymer matrix.

23. The composition of claim 22, wherein the positively-charged polymer matrix comprises poly-β-amino ester (PBAE).

24. The composition of claim 22, wherein the positively-charged polymer matrix is surrounded by a negatively-charged coating.

25. The composition of claim 24, wherein the negatively-charged coating comprises polyglutamic acid (PGA).

26. A method, comprising:

administering an effective amount of a nanoparticle to a subject vaccinated with a vaccine antigen; wherein the nanoparticle comprises:

(i) a polynucleotide encoding a T cell receptor (TCR) that specifically binds the vaccine antigen; and (ii) a binding fragment of an anti-CD4 or anti-CD8 antibody exposed on the surface of the nanoparticle.

27. The method of claim 7, wherein the vaccine adjuvant is selected from CpG, Cpg-28, Polyriboinosinic polyribocytidylic acid (Poly(I:C)), α-galactoceramide, monophosphoryl lipid A (MPLA), 1-isobutyl-1H-imidazo[4,5-c]quinolin-4-amine, polyinosinic-polycytidylic acid stabilized with polylysine and carboxymethylcellulose, and 17-dimethylaminoethylamino-17-demethoxygeldanamycin, and/or a stimulator of interferon genes (STING) agonist selected from c-diGMP, c-diAMP, c-GAMP, c-AIMP, (3',2')c-AIMP, (2',2')c-AIMP, (2',3')c-AIMP, c-AIMP(S), c-(dAMP-dIMP), c-(dAMP-2'FdIMP), c-(2'FdAMP-2'FdIMP), (2',3')c-(AMP-2'FdIMP), c-[2'FdAMP(S)-2'FdIMP(S)], c-[2'FdAMP(S)-2'FdIMP(S)](POM)$^2$, and/or dimethylxanthenone acetic acid (DMXAA).

28. The method of claim 1, wherein the vaccine antigen comprises mesothelin.

* * * * *

SEQUENCE LISTING

<160> NUMBER OF SEQ ID NOS: 142

<210> SEQ ID NO 1
<211> LENGTH: 263
<212> TYPE: PRT
<213> ORGANISM: Homo sapiens

<400> SEQUENCE: 1

Met Asn Ser Ser Leu Asp Phe Leu Ile Leu Ile Leu Met Phe Gly Gly
1               5                   10                  15

Thr Ser Ser Asn Ser Val Lys Gln Thr Gly Gln Ile Thr Val Ser Glu
            20                  25                  30

Gly Ala Ser Val Thr Met Asn Cys Thr Tyr Thr Ser Thr Gly Tyr Pro
        35                  40                  45

Thr Leu Phe Trp Tyr Val Glu Tyr Pro Ser Lys Pro Leu Gln Leu Leu
    50                  55                  60

Gln Arg Glu Thr Met Glu Asn Ser Lys Asn Phe Gly Gly Gly Asn Ile
65                  70                  75                  80

Lys Asp Lys Asn Ser Pro Ile Val Lys Tyr Ser Val Gln Val Ser Asp
                85                  90                  95

Ser Ala Val Tyr Tyr Cys Leu Leu Arg Asn His Asp Lys Leu Ile Phe
            100                 105                 110

Gly Thr Gly Thr Arg Leu Gln Val Phe Pro Asn Ile Gln Asn Pro Asp
        115                 120                 125

Pro Ala Val Tyr Gln Leu Arg Asp Ser Lys Ser Ser Asp Lys Ser Val
    130                 135                 140

Cys Leu Phe Thr Asp Phe Asp Ser Gln Thr Asn Val Ser Gln Ser Lys
145                 150                 155                 160

Asp Ser Asp Val Tyr Ile Thr Asp Lys Thr Val Leu Asp Met Arg Ser
                165                 170                 175

Met Asp Phe Lys Ser Asn Ser Ala Val Ala Trp Ser Asn Lys Ser Asp
            180                 185                 190

Phe Ala Cys Ala Asn Ala Phe Asn Asn Ser Ile Ile Pro Glu Asp Thr
        195                 200                 205

Phe Phe Pro Ser Pro Glu Ser Ser Cys Asp Val Lys Leu Val Glu Lys
    210                 215                 220

Ser Phe Glu Thr Asp Thr Asn Leu Asn Phe Gln Asn Leu Ser Val Ile
225                 230                 235                 240

Gly Phe Arg Ile Leu Leu Leu Lys Val Ala Gly Phe Asn Leu Leu Met
                245                 250                 255

Thr Leu Arg Leu Trp Ser Ser
            260

```
<210> SEQ ID NO 2
<211> LENGTH: 310
<212> TYPE: PRT
<213> ORGANISM: Homo sapiens

<400> SEQUENCE: 2

Met Gly Pro Gly Leu Leu Cys Trp Val Leu Leu Cys Leu Leu Gly Ala
1               5                   10                  15

Gly Ser Val Glu Thr Gly Val Thr Gln Ser Pro Thr His Leu Ile Lys
            20                  25                  30

Thr Arg Gly Gln Gln Val Thr Leu Arg Cys Ser Ser Gln Ser Gly His
        35                  40                  45

Asn Thr Val Ser Trp Tyr Gln Gln Ala Leu Gly Gln Gly Pro Gln Phe
    50                  55                  60

Ile Phe Gln Tyr Tyr Arg Glu Glu Asn Gly Arg Gly Asn Phe Pro
65                  70                  75                  80

Pro Arg Phe Ser Gly Leu Gln Phe Pro Asn Tyr Ser Ser Glu Leu Asn
                85                  90                  95

Val Asn Ala Leu Glu Leu Asp Asp Ser Ala Leu Tyr Leu Cys Ala Ser
            100                 105                 110

Ser Gln Asp Ser Tyr Asn Glu Gln Phe Phe Gly Pro Gly Thr Arg Leu
        115                 120                 125

Thr Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 3
<211> LENGTH: 312
<212> TYPE: PRT
<213> ORGANISM: Homo sapiens

<400> SEQUENCE: 3

Met Gly Pro Gly Leu Leu Cys Trp Val Leu Leu Cys Leu Leu Gly Ala
1               5                   10                  15

Gly Ser Val Glu Thr Gly Val Thr Gln Ser Pro Thr His Leu Ile Lys
```

```
                20                  25                  30
Thr Arg Gly Gln Gln Val Thr Leu Arg Cys Ser Ser Gln Ser Gly His
            35                  40                  45

Asn Thr Val Ser Trp Tyr Gln Gln Ala Leu Gly Gln Gly Pro Gln Phe
 50                  55                  60

Ile Phe Gln Tyr Tyr Arg Glu Glu Asn Gly Arg Gly Asn Phe Pro
 65                  70                  75                  80

Pro Arg Phe Ser Gly Leu Gln Phe Pro Asn Tyr Ser Ser Glu Leu Asn
                85                  90                  95

Val Asn Ala Leu Glu Leu Asp Asp Ser Ala Leu Tyr Leu Cys Ala Ser
            100                 105                 110

Ser Leu Ala Gly Gly Tyr Gly Asp Thr Gln Tyr Phe Gly Pro Gly Thr
            115                 120                 125

Arg Leu Thr Val Leu Glu Asp Leu Lys Asn Val Phe Pro Pro Glu Val
            130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
            165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
            210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
            245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
            275                 280                 285

Ala Thr Leu Tyr Ala Val Leu Val Ser Ala Leu Val Leu Met Ala Met
            290                 295                 300

Val Lys Arg Lys Asp Ser Arg Gly
305                 310

<210> SEQ ID NO 4
<211> LENGTH: 272
<212> TYPE: PRT
<213> ORGANISM: Homo sapiens

<400> SEQUENCE: 4

Met Lys Lys Leu Leu Ala Met Ile Leu Trp Leu Gln Leu Asp Arg Leu
  1               5                  10                  15

Ser Gly Glu Leu Lys Val Glu Gln Asn Pro Leu Phe Leu Ser Met Gln
            20                  25                  30

Glu Gly Lys Asn Tyr Thr Ile Tyr Cys Asn Tyr Ser Thr Thr Ser Asp
            35                  40                  45

Arg Leu Tyr Trp Tyr Arg Gln Asp Pro Gly Lys Ser Leu Glu Ser Leu
            50                  55                  60

Phe Val Leu Leu Ser Asn Gly Ala Val Lys Gln Glu Gly Arg Leu Met
 65                  70                  75                  80
```

```
Ala Ser Leu Asp Thr Lys Ala Arg Leu Ser Thr Leu His Ile Thr Ala
                85                  90                  95

Ala Val His Asp Leu Ser Ala Thr Tyr Phe Cys Ala Val Gly Asn Tyr
            100                 105                 110

Gly Gly Ser Gln Gly Asn Leu Ile Phe Gly Lys Gly Thr Lys Leu Ser
        115                 120                 125

Val Lys Pro Asn Ile Gln Asn Pro Asp Pro Ala Val Tyr Gln Leu Arg
130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 5
<211> LENGTH: 123
<212> TYPE: PRT
<213> ORGANISM: Homo sapiens

<400> SEQUENCE: 5

Met Asn Ser Ser Leu Asp Phe Leu Ile Leu Ile Leu Met Phe Gly Gly
1               5                   10                  15

Thr Ser Ser Asn Ser Val Lys Gln Thr Gly Gln Ile Thr Val Ser Glu
                20                  25                  30

Gly Ala Ser Val Thr Met Asn Cys Thr Tyr Thr Ser Thr Gly Tyr Pro
            35                  40                  45

Thr Leu Phe Trp Tyr Val Glu Tyr Pro Ser Lys Pro Leu Gln Leu Leu
        50                  55                  60

Gln Arg Glu Thr Met Glu Asn Ser Lys Asn Phe Gly Gly Gly Asn Ile
65                  70                  75                  80

Lys Asp Lys Asn Ser Pro Ile Val Lys Tyr Ser Val Gln Val Ser Asp
                85                  90                  95

Ser Ala Val Tyr Tyr Cys Leu Leu Arg Asn His Asp Lys Leu Ile Phe
            100                 105                 110

Gly Thr Gly Thr Arg Leu Gln Val Phe Pro Asn
        115                 120

<210> SEQ ID NO 6
<211> LENGTH: 132
<212> TYPE: PRT
<213> ORGANISM: Homo sapiens

<400> SEQUENCE: 6

Met Lys Lys Leu Leu Ala Met Ile Leu Trp Leu Gln Leu Asp Arg Leu
1               5                   10                  15
```

Ser Gly Glu Leu Lys Val Glu Gln Asn Pro Leu Phe Leu Ser Met Gln
        20                  25                  30

Glu Gly Lys Asn Tyr Thr Ile Tyr Cys Asn Tyr Ser Thr Ser Ser Asp
            35                  40                  45

Arg Leu Tyr Trp Tyr Arg Gln Asp Pro Gly Lys Ser Leu Glu Ser Leu
50                      55                  60

Phe Val Leu Leu Ser Asn Gly Ala Val Lys Gln Glu Gly Arg Leu Met
65                  70                  75                  80

Ala Ser Leu Asp Thr Lys Ala Arg Leu Ser Thr Leu His Ile Thr Ala
                85                  90                  95

Ala Val His Asp Leu Ser Ala Thr Tyr Phe Cys Ala Val Gly Asn Tyr
            100                 105                 110

Gly Gly Ser Gln Gly Asn Leu Ile Phe Gly Lys Gly Thr Lys Leu Ser
        115                 120                 125

Val Lys Pro Asn
    130

<210> SEQ ID NO 7
<211> LENGTH: 132
<212> TYPE: PRT
<213> ORGANISM: Homo sapiens

<400> SEQUENCE: 7

Met Gly Pro Gly Leu Leu Cys Trp Val Leu Leu Cys Leu Leu Gly Ala
1               5                   10                  15

Gly Ser Val Glu Thr Gly Val Thr Gln Ser Pro Thr His Leu Ile Lys
            20                  25                  30

Thr Arg Gly Gln Gln Val Thr Leu Arg Cys Ser Ser Gln Ser Gly His
        35                  40                  45

Asn Thr Val Ser Trp Tyr Gln Gln Ala Leu Gly Gln Gly Pro Gln Phe
    50                  55                  60

Ile Phe Gln Tyr Tyr Arg Glu Glu Glu Asn Gly Arg Gly Asn Phe Pro
65                  70                  75                  80

Pro Arg Phe Ser Gly Leu Gln Phe Pro Asn Tyr Ser Ser Glu Leu Asn
                85                  90                  95

Val Asn Ala Leu Glu Leu Asp Asp Ser Ala Leu Tyr Leu Cys Ala Ser
            100                 105                 110

Ser Gln Asp Ser Tyr Asn Glu Gln Phe Phe Gly Pro Gly Thr Arg Leu
        115                 120                 125

Thr Val Leu Glu
    130

<210> SEQ ID NO 8
<211> LENGTH: 134
<212> TYPE: PRT
<213> ORGANISM: Homo sapiens

<400> SEQUENCE: 8

Met Gly Pro Gly Leu Leu Cys Trp Val Leu Leu Cys Leu Leu Gly Ala
1               5                   10                  15

Gly Ser Val Glu Thr Gly Val Thr Gln Ser Pro Thr His Leu Ile Lys
            20                  25                  30

Thr Arg Gly Gln Gln Val Thr Leu Arg Cys Ser Ser Gln Ser Gly His
        35                  40                  45

Asn Thr Val Ser Trp Tyr Gln Gln Ala Leu Gly Gln Gly Pro Gln Phe
    50                  55                  60

-continued

Ile Phe Gln Tyr Tyr Arg Glu Glu Asn Gly Arg Gly Asn Phe Pro
 65                  70                  75                  80

Pro Arg Phe Ser Gly Leu Gln Phe Pro Asn Tyr Ser Glu Leu Asn
                 85                  90                  95

Val Asn Ala Leu Glu Leu Asp Asp Ser Ala Leu Tyr Leu Cys Ala Ser
            100                 105                 110

Ser Leu Ala Gly Gly Tyr Gly Asp Thr Gln Tyr Phe Gly Pro Gly Thr
        115                 120                 125

Arg Leu Thr Val Leu Glu
    130

<210> SEQ ID NO 9
<211> LENGTH: 11
<212> TYPE: PRT
<213> ORGANISM: Homo sapiens

<400> SEQUENCE: 9

Cys Leu Leu Arg Asn His Asp Lys Leu Ile Phe
1               5                   10

<210> SEQ ID NO 10
<211> LENGTH: 15
<212> TYPE: PRT
<213> ORGANISM: Homo sapiens

<400> SEQUENCE: 10

Cys Ala Val Gly Asn Tyr Gly Gly Ser Gln Gly Asn Leu Ile Phe
1               5                   10                  15

<210> SEQ ID NO 11
<211> LENGTH: 13
<212> TYPE: PRT
<213> ORGANISM: Homo sapiens

<400> SEQUENCE: 11

Cys Ala Ser Ser Gln Asp Ser Tyr Asn Glu Gln Phe Phe
1               5                   10

<210> SEQ ID NO 12
<211> LENGTH: 15
<212> TYPE: PRT
<213> ORGANISM: Homo sapiens

<400> SEQUENCE: 12

Cys Ala Ser Ser Leu Ala Gly Gly Tyr Gly Asp Thr Gln Tyr Phe
1               5                   10                  15

<210> SEQ ID NO 13
<211> LENGTH: 9
<212> TYPE: PRT
<213> ORGANISM: Homo sapiens

<400> SEQUENCE: 13

Ser Leu Leu Phe Leu Leu Phe Ser Leu
1               5

<210> SEQ ID NO 14
<211> LENGTH: 9
<212> TYPE: PRT
<213> ORGANISM: Homo sapiens

<400> SEQUENCE: 14

Val Leu Pro Leu Thr Val Ala Glu Val

```
                             -continued
1              5

<210> SEQ ID NO 15
<211> LENGTH: 8
<212> TYPE: PRT
<213> ORGANISM: murine

<400> SEQUENCE: 15

Leu Asp Tyr Ala Asn Lys Met Ile
1               5

<210> SEQ ID NO 16
<211> LENGTH: 8
<212> TYPE: PRT
<213> ORGANISM: murine

<400> SEQUENCE: 16

Pro Gln Asp Thr Gln Tyr Phe Phe
1               5

<210> SEQ ID NO 17
<211> LENGTH: 9
<212> TYPE: PRT
<213> ORGANISM: murine

<400> SEQUENCE: 17

Gly Gln Lys Met Asn Ala Gln Ala Ile
1               5

<210> SEQ ID NO 18
<211> LENGTH: 205
<212> TYPE: PRT
<213> ORGANISM: Homo sapiens

<400> SEQUENCE: 18

Met Gln Lys Glu Val Glu Gln Asn Ser Gly Pro Leu Ser Val Pro Glu
1               5                  10                  15

Gly Ala Ile Ala Ser Leu Asn Cys Thr Tyr Ser Asp Arg Gly Ser Gln
                20                  25                  30

Ser Phe Phe Trp Tyr Arg Gln Tyr Ser Gly Lys Ser Pro Glu Leu Ile
            35                  40                  45

Met Phe Ile Tyr Ser Asn Gly Asp Lys Glu Asp Gly Arg Phe Thr Ala
        50                  55                  60

Gln Leu Asn Lys Ala Ser Gln Tyr Ile Ser Leu Leu Ile Arg Asp Ser
65                  70                  75                  80

Lys Leu Ser Lys Ala Thr Tyr Leu Cys Ala Val Arg Thr Asn Ser Gly
                85                  90                  95

Tyr Ala Leu Asn Phe Gly Lys Gly Thr Ser Leu Leu Val Thr Pro His
                100                 105                 110

Ile Gln Lys Pro Asp Pro Ala Val Tyr Gln Leu Arg Asp Ser Lys Ser
            115                 120                 125

Ser Asp Lys Ser Val Cys Leu Phe Thr Asp Phe Asp Ser Gln Thr Asn
        130                 135                 140

Val Ser Gln Ser Lys Asp Ser Asp Val Tyr Ile Thr Asp Lys Cys Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
                180                 185                 190
```

```
Ile Pro Glu Asp Thr Phe Phe Pro Ser Pro Glu Ser Ser
        195                 200                 205
```

<210> SEQ ID NO 19
<211> LENGTH: 242
<212> TYPE: PRT
<213> ORGANISM: Homo sapiens

<400> SEQUENCE: 19

```
Met Glu Ala Gly Val Thr Gln Ser Pro Thr His Leu Ile Lys Thr Arg
1               5                   10                  15

Gly Gln Gln Val Thr Leu Arg Cys Ser Pro Lys Ser Gly His Asp Thr
            20                  25                  30

Val Ser Trp Tyr Gln Gln Ala Leu Gly Gln Gly Pro Gln Phe Ile Phe
        35                  40                  45

Gln Tyr Tyr Glu Glu Glu Arg Gln Arg Gly Asn Phe Pro Asp Arg
    50                  55                  60

Phe Ser Gly His Gln Phe Pro Asn Tyr Ser Ser Glu Leu Asn Val Asn
65                  70                  75                  80

Ala Leu Leu Leu Gly Asp Ser Ala Leu Tyr Leu Cys Ala Ser Ser Asp
                85                  90                  95

Thr Val Ser Tyr Glu Gln Tyr Phe Gly Pro Gly Thr Arg Thr Val Thr
            100                 105                 110

Glu Asp Leu Lys Asn Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Tyr Pro Asp His Val Glu Leu Ser Trp Trp Val Asn
145                 150                 155                 160

Gly Lys Glu Val His Ser Gly Val Cys Thr Asp Pro Gln Pro Leu Lys
                165                 170                 175

Glu Gln Pro Ala Leu Asn Asp Ser Arg Tyr Ala Leu Ser Ser Arg Leu
            180                 185                 190

Arg Val Ser Ala Thr Phe Trp Gln Asp Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Asp
```

<210> SEQ ID NO 20
<211> LENGTH: 9
<212> TYPE: PRT
<213> ORGANISM: Human immunodeficiency virus

<400> SEQUENCE: 20

```
Ser Leu Tyr Asn Thr Val Ala Thr Leu
1               5
```

<210> SEQ ID NO 21
<211> LENGTH: 133
<212> TYPE: PRT
<213> ORGANISM: Homo sapiens

<400> SEQUENCE: 21

```
Met Glu Thr Leu Leu Gly Leu Leu Ile Leu Trp Leu Gln Leu Gln Trp
1               5                   10                  15
```

-continued

Val Ser Ser Lys Gln Glu Val Thr Gln Ile Pro Ala Ala Leu Ser Val
                20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
 50                  55                  60

Ser Leu Leu Leu Ile Gln Ser Ser Gln Arg Glu Gln Thr Ser Gly Arg
 65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Arg Asn Asp Met Arg Phe Gly Ala Gly Thr Arg Leu Thr Val Lys Pro
            115                 120                 125

Asn Ile Gln Asn Pro
            130

<210> SEQ ID NO 22
<211> LENGTH: 142
<212> TYPE: PRT
<213> ORGANISM: Homo sapiens

<400> SEQUENCE: 22

Met Gly Ile Arg Leu Leu Cys Arg Val Ala Phe Cys Phe Leu Ala Val
 1               5                  10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
 50                  55                  60

Ile Tyr Phe Ser Tyr Asp Val Lys Met Lys Glu Lys Gly Asp Ile Pro
 65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Pro Gly Ala Leu Asp Thr Asp Thr Gln Tyr Phe Gly Pro Gly Thr
            115                 120                 125

Arg Leu Thr Val Val Glu Asp Ile Lys Asn Val Phe Pro Pro
            130                 135                 140

<210> SEQ ID NO 23
<211> LENGTH: 270
<212> TYPE: PRT
<213> ORGANISM: Homo sapiens

<400> SEQUENCE: 23

Met Thr Ser Ile Arg Ala Val Phe Ile Phe Leu Trp Leu Gln Leu Asp
 1               5                  10                  15

Leu Val Asn Gly Glu Asn Val Glu Gln His Pro Ser Thr Leu Ser Val
                20                  25                  30

Gln Glu Gly Asp Ser Ala Val Ile Lys Cys Thr Tyr Ser Asp Ser Ala
            35                  40                  45

Ser Asn Tyr Phe Pro Trp Tyr Lys Gln Glu Leu Gly Lys Arg Pro Gln
 50                  55                  60

Leu Ile Ile Asp Ile Arg Ser Asn Val Gly Glu Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Thr
            100                 105                 110

Glu Asp Tyr Gln Leu Ile Trp Gly Ala Gly Thr Lys Leu Ile Ile Lys
        115                 120                 125

Pro Asp Ile Gln Asn Pro Asp Pro Ala Val Tyr Gln Leu Arg Asp Ser
130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 24
<211> LENGTH: 310
<212> TYPE: PRT
<213> ORGANISM: Homo sapiens

<400> SEQUENCE: 24

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Pro Gly Ala Leu Tyr Glu Gln Tyr Phe Gly Pro Gly Thr Arg Leu
        115                 120                 125

Thr Val Thr Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp

```
                165                 170                 175
Trp Val Asn Gly Lys Glu Val His Ser Gly Val Ser Thr Asp Pro Gln
            180                 185                 190
Pro Leu Lys Glu Gln Pro Ala Leu Asn Asp Ser Arg Tyr Cys Leu Ser
        195                 200                 205
Ser Arg Leu Arg Val Ser Ala Thr Phe Trp Gln Asn Pro Arg Asn His
    210                 215                 220
Phe Arg Cys Gln Val Gln Phe Tyr Gly Leu Ser Glu Asn Asp Glu Trp
225                 230                 235                 240
Thr Gln Asp Arg Ala Lys Pro Val Thr Gln Ile Val Ser Ala Glu Ala
                245                 250                 255
Trp Gly Arg Ala Asp Cys Gly Phe Thr Ser Glu Ser Tyr Gln Gln Gly
            260                 265                 270
Val Leu Ser Ala Thr Ile Leu Tyr Glu Ile Leu Leu Gly Lys Ala Thr
        275                 280                 285
Leu Tyr Ala Val Leu Val Ser Ala Leu Val Leu Met Ala Met Val Lys
    290                 295                 300
Arg Lys Asp Ser Arg Gly
305                 310

<210> SEQ ID NO 25
<211> LENGTH: 270
<212> TYPE: PRT
<213> ORGANISM: Homo sapiens

<400> SEQUENCE: 25

Met Thr Ser Ile Arg Ala Val Phe Ile Phe Leu Trp Leu Gln Leu Asp
1               5                   10                  15
Leu Val Asn Gly Glu Asn Val Glu Gln His Pro Ser Thr Leu Ser Val
            20                  25                  30
Gln Glu Gly Asp Ser Ala Val Ile Lys Cys Thr Tyr Ser Asp Ser Ala
        35                  40                  45
Ser Asn Tyr Phe Pro Trp Tyr Lys Gln Glu Leu Gly Lys Arg Pro Gln
    50                  55                  60
Leu Ile Ile Asp Ile Arg Ser Asn Val Gly Glu Lys Lys Asp Gln Arg
65                  70                  75                  80
Ile Ala Val Thr Leu Asn Lys Thr Ala Lys His Phe Ser Leu His Ile
                85                  90                  95
Thr Glu Thr Gln Pro Glu Asp Ser Ala Val Tyr Phe Cys Ala Ala Thr
            100                 105                 110
Glu Asp Tyr Gln Leu Ile Trp Gly Ala Gly Thr Lys Leu Ile Ile Lys
        115                 120                 125
Pro Asp Ile Gln Asn Pro Asp Pro Ala Val Tyr Gln Leu Arg Asp Ser
    130                 135                 140
Lys Ser Ser Asp Lys Ser Val Cys Leu Phe Thr Asp Phe Asp Ser Gln
145                 150                 155                 160
Thr Asn Val Ser Gln Ser Lys Asp Ser Asp Val Tyr Ile Thr Asp Lys
                165                 170                 175
Cys Val Leu Asp Met Arg Ser Met Asp Phe Lys Ser Asn Ser Ala Val
            180                 185                 190
Ala Trp Ser Asn Lys Ser Asp Phe Ala Cys Ala Asn Ala Phe Asn Asn
        195                 200                 205
Ser Ile Ile Pro Glu Asp Thr Phe Phe Pro Ser Pro Glu Ser Ser Cys
    210                 215                 220
```

```
Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
            245                 250                 255

Ala Gly Phe Asn Leu Leu Met Thr Leu Arg Leu Trp Ser Ser
        260                 265                 270

<210> SEQ ID NO 26
<211> LENGTH: 310
<212> TYPE: PRT
<213> ORGANISM: Homo sapiens

<400> SEQUENCE: 26

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Pro Gly Ala Leu Tyr Glu Gln Tyr Phe Gly Pro Gly Thr Arg Leu
        115                 120                 125

Thr Val Thr Glu Asp Leu Lys Asn Val Phe Pro Pro Glu Val Ala Val
            130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Cys Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
290                 295                 300

Arg Lys Asp Ser Arg Gly
305                 310

<210> SEQ ID NO 27
```

```
<211> LENGTH: 275
<212> TYPE: PRT
<213> ORGANISM: Homo sapiens

<400> SEQUENCE: 27

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Leu Arg Ser Ser Gly Thr Tyr Lys Tyr Ile Phe Gly Thr Gly Thr
        115                 120                 125

Arg Leu Lys Val Leu Ala Asn Ile Gln Asn Pro Asp Pro Ala Val Tyr
130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 28
<211> LENGTH: 313
<212> TYPE: PRT
<213> ORGANISM: Homo sapiens

<400> SEQUENCE: 28

Met Gly Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Ser Leu Gly Gln Gly Leu Glu Phe
50                  55                  60
```

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Gly Ser Val Ser Thr Leu
                85                  90                  95

Thr Ile Gln Arg Thr Gln Gln Glu Asp Ser Ala Val Tyr Leu Cys Ala
            100                 105                 110

Ser Ile Arg Thr Gly Pro Phe Phe Ser Gly Asn Thr Ile Tyr Phe Gly
        115                 120                 125

Glu Gly Ser Trp Leu Thr Val Val Glu Asp Leu Asn Lys Val Phe Pro
    130                 135                 140

Pro Glu Val Ala Val Phe Glu Pro Ser Glu Ala Glu Ile Ser His Thr
145                 150                 155                 160

Gln Lys Ala Thr Leu Val Cys Leu Ala Thr Gly Phe Phe Pro Asp His
                165                 170                 175

Val Glu Leu Ser Trp Trp Val Asn Gly Lys Glu Val His Ser Gly Val
            180                 185                 190

Ser Thr Asp Pro Gln Pro Leu Lys Glu Gln Pro Ala Leu Asn Asp Ser
        195                 200                 205

Arg Tyr Cys Leu Ser Ser Arg Leu Arg Val Ser Ala Thr Phe Trp Gln
    210                 215                 220

Asn Pro Arg Asn His Phe Arg Cys Gln Val Gln Phe Tyr Gly Leu Ser
225                 230                 235                 240

Glu Asn Asp Glu Trp Thr Gln Asp Arg Ala Lys Pro Val Thr Gln Ile
                245                 250                 255

Val Ser Ala Glu Ala Trp Gly Arg Ala Asp Cys Gly Phe Thr Ser Val
            260                 265                 270

Ser Tyr Gln Gln Gly Val Leu Ser Ala Thr Ile Leu Tyr Glu Ile Leu
        275                 280                 285

Leu Gly Lys Ala Thr Leu Tyr Ala Val Leu Val Ser Ala Leu Val Leu
    290                 295                 300

Met Ala Met Val Lys Arg Lys Asp Phe
305                 310

<210> SEQ ID NO 29
<211> LENGTH: 275
<212> TYPE: PRT
<213> ORGANISM: Homo sapiens

<400> SEQUENCE: 29

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Leu Arg Ala Ser Gly Thr Tyr Lys Tyr Ile Phe Gly Thr Gly Thr

```
            115                 120                 125
Arg Leu Lys Val Leu Ala Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 30
<211> LENGTH: 275
<212> TYPE: PRT
<213> ORGANISM: Homo sapiens

<400> SEQUENCE: 30

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
                20                  25                  30

Val Gln Glu Ala Glu Thr Val Thr Leu Ser Cys Thr Tyr Asp Thr Ser
            35                  40                  45

Glu Ser Asp Tyr Tyr Leu Phe Trp Tyr Lys Gln Pro Pro Ser Arg Gln
        50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Leu Arg Ser Ala Gly Thr Tyr Lys Tyr Ile Phe Gly Thr Gly Thr
        115                 120                 125

Arg Leu Lys Val Leu Ala Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205
```

Asn Ala Phe Asn Asn Ser Ile Ile Pro Glu Asp Thr Phe Phe Pro Ser
    210                 215                 220
Pro Glu Ser Ser Cys Asp Val Lys Leu Val Glu Lys Ser Phe Glu Thr
225                 230                 235                 240
Asp Thr Asn Leu Asn Phe Gln Asn Leu Ser Val Ile Gly Phe Arg Ile
                245                 250                 255
Leu Leu Leu Lys Val Ala Gly Phe Asn Leu Leu Met Thr Leu Arg Leu
                260                 265                 270
Trp Ser Ser
    275

<210> SEQ ID NO 31
<211> LENGTH: 275
<212> TYPE: PRT
<213> ORGANISM: Homo sapiens

<400> SEQUENCE: 31

Met Ala Cys Pro Gly Phe Leu Trp Ala Leu Val Ile Ser Thr Cys Leu
1               5                   10                  15
Glu Phe Ser Met Ala Gln Thr Val Thr Gln Ser Gln Pro Glu Met Ser
                20                  25                  30
Val Gln Glu Ala Glu Thr Val Thr Leu Ser Cys Thr Tyr Asp Thr Ser
            35                  40                  45
Glu Ser Asp Tyr Tyr Leu Phe Trp Tyr Lys Gln Pro Pro Ser Arg Gln
    50                  55                  60
Met Ile Leu Val Ile Arg Gln Glu Ala Tyr Lys Gln Gln Asn Ala Thr
65                  70                  75                  80
Glu Asn Arg Phe Ser Val Asn Phe Gln Lys Ala Ala Lys Ser Phe Ser
                85                  90                  95
Leu Lys Ile Ser Asp Ser Gln Leu Gly Asp Ala Ala Met Tyr Phe Cys
            100                 105                 110
Ala Leu Arg Val Ser Gly Thr Tyr Lys Tyr Ile Phe Gly Thr Gly Thr
        115                 120                 125
Arg Leu Lys Val Leu Ala Asn Ile Gln Asn Pro Asp Pro Ala Val Tyr
130                 135                 140
Gln Leu Arg Asp Ser Lys Ser Ser Asp Lys Ser Val Cys Leu Phe Thr
145                 150                 155                 160
Asp Phe Asp Ser Gln Thr Asn Val Ser Gln Ser Lys Asp Ser Asp Val
                165                 170                 175
Tyr Ile Thr Asp Lys Thr Val Leu Asp Met Arg Ser Met Asp Phe Lys
            180                 185                 190
Ser Asn Ser Ala Val Ala Trp Ser Asn Lys Ser Asp Phe Ala Cys Ala
        195                 200                 205
Asn Ala Phe Asn Asn Ser Ile Ile Pro Glu Asp Thr Phe Phe Pro Ser
    210                 215                 220
Pro Glu Ser Ser Cys Asp Val Lys Leu Val Glu Lys Ser Phe Glu Thr
225                 230                 235                 240
Asp Thr Asn Leu Asn Phe Gln Asn Leu Ser Val Ile Gly Phe Arg Ile
                245                 250                 255
Leu Leu Leu Lys Val Ala Gly Phe Asn Leu Leu Met Thr Leu Arg Leu
            260                 265                 270
Trp Ser Ser
    275

<210> SEQ ID NO 32

```
<211> LENGTH: 271
<212> TYPE: PRT
<213> ORGANISM: Homo sapiens

<400> SEQUENCE: 32

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Leu Arg Ser Ser Gly Thr Tyr Lys Tyr Ile Phe Gly Thr Gly Thr
        115                 120                 125

Arg Leu Lys Val Leu Ala Asn Ile Gln Asn Pro Glu Pro Ala Val Tyr
    130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Thr Val Leu Asp Met Lys Ala Met Asp Ser Lys
            180                 185                 190

Ser Asn Gly Ala Ile Ala Trp Ser Asn Gln Thr Ser Phe Thr Cys Gln
        195                 200                 205

Asp Ile Phe Lys Glu Thr Asn Ala Thr Tyr Pro Ser Ser Asp Val Pro
    210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 33
<211> LENGTH: 309
<212> TYPE: PRT
<213> ORGANISM: Homo sapiens

<400> SEQUENCE: 33

Met Gly Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Ser Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80
```

Ser Asp Arg Phe Ser Ala Glu Arg Thr Gly Gly Ser Val Ser Thr Leu
            85                  90                  95

Thr Ile Gln Arg Thr Gln Gln Glu Asp Ser Ala Val Tyr Leu Cys Ala
            100                 105                 110

Ser Ile Arg Thr Gly Pro Phe Phe Ser Gly Asn Thr Ile Tyr Phe Gly
            115                 120                 125

Glu Gly Ser Trp Leu Thr Val Val Glu Asp Leu Arg Asn Val Thr Pro
        130                 135                 140

Pro Lys Val Ser Leu Phe Glu Pro Ser Lys Ala Glu Ile Ala Asn Lys
145                 150                 155                 160

Gln Lys Ala Thr Leu Val Cys Leu Ala Arg Gly Phe Phe Pro Asp His
            165                 170                 175

Val Glu Leu Ser Trp Trp Val Asn Gly Lys Glu Val His Ser Gly Val
            180                 185                 190

Ser Thr Asp Pro Gln Ala Tyr Lys Glu Ser Asn Tyr Ser Tyr Cys Leu
            195                 200                 205

Ser Ser Arg Leu Arg Val Ser Ala Thr Phe Trp His Asn Pro Arg Asn
        210                 215                 220

His Phe Arg Cys Gln Val Gln Phe His Gly Leu Ser Glu Glu Asp Lys
225                 230                 235                 240

Trp Pro Glu Gly Ser Pro Lys Pro Val Thr Gln Asn Ile Ser Ala Glu
            245                 250                 255

Ala Trp Gly Arg Ala Asp Cys Gly Ile Thr Ser Ala Ser Tyr His Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Gly Leu Val Leu Met Ala Met Val
        290                 295                 300

Lys Arg Lys Asn Ser
305

<210> SEQ ID NO 34
<211> LENGTH: 208
<212> TYPE: PRT
<213> ORGANISM: Homo sapiens

<400> SEQUENCE: 34

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Tyr
            85                  90                  95

Gly Gly Ser Tyr Ile Pro Thr Phe Gly Arg Gly Thr Ser Leu Ile Val
            100                 105                 110

His Pro Tyr Ile Gln Asn Pro Asp Pro Ala Val Tyr Gln Leu Arg Asp
            115                 120                 125

Ser Lys Ser Ser Asp Lys Ser Val Cys Leu Phe Thr Asp Phe Asp Ser

Gln Thr Asn Val Ser Gln Ser Lys Asp Ser Asp Val Tyr Ile Thr Asp
145                 150                 155                 160

Lys Thr Val Leu Asp Met Arg Ser Met Asp Phe Lys Ser Asn Ser Ala
            165                 170                 175

Val Ala Trp Ser Asn Lys Ser Asp Phe Ala Cys Ala Asn Ala Phe Asn
        180                 185                 190

Asn Ser Ile Ile Pro Glu Asp Thr Phe Phe Pro Ser Pro Glu Ser Ser
        195                 200                 205

<210> SEQ ID NO 35
<211> LENGTH: 242
<212> TYPE: PRT
<213> ORGANISM: Homo sapiens

<400> SEQUENCE: 35

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Asn
50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
            100                 105                 110

Glu Asp Leu Lys Asn Val Phe Pro Pro Glu Val Ala Val Phe Glu Pro
        115                 120                 125

Ser Glu Ala Glu Ile Ser His Thr Gln Lys Ala Thr Leu Val Cys Leu
130                 135                 140

Ala Thr Gly Phe Tyr Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175

Glu Gln Pro Ala Leu Asn Asp Ser Arg Tyr Ala Leu Ser Ser Arg Leu
            180                 185                 190

Arg Val Ser Ala Thr Phe Trp Gln Asp Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Asp

<210> SEQ ID NO 36
<211> LENGTH: 208
<212> TYPE: PRT
<213> ORGANISM: Homo sapiens

<400> SEQUENCE: 36

Met Gln Glu Val Thr Gln Ile Pro Ala Ala Leu Ser Val Pro Glu Gly
1               5                   10                  15

```
Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Tyr
                85                  90                  95

Gly Gly Ser Tyr Ile Pro Thr Phe Gly Arg Gly Thr Ser Leu Ile Val
               100                 105                 110

His Pro Tyr Ile Gln Asn Pro Asp Pro Ala Val Tyr Gln Leu Arg Asp
           115                 120                 125

Ser Lys Ser Ser Asp Lys Ser Val Cys Leu Phe Thr Asp Phe Asp Ser
    130                 135                 140

Gln Thr Asn Val Ser Gln Ser Lys Asp Ser Asp Val Tyr Ile Thr Asp
145                 150                 155                 160

Lys Cys Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205

<210> SEQ ID NO 37
<211> LENGTH: 242
<212> TYPE: PRT
<213> ORGANISM: Homo sapiens

<400> SEQUENCE: 37

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
                20                  25                  30

Trp Tyr Arg Gln Asp Pro Gly Met Gly Leu Arg Leu Ile His Tyr Ser
            35                  40                  45

Val Gly Ala Gly Ile Thr Asp Gln Gly Glu Val Pro Asn Gly Tyr Asn
        50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
            100                 105                 110

Glu Asp Leu Lys Asn Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Tyr Pro Asp His Val Glu Leu Ser Trp Trp Val Asn
145                 150                 155                 160

Gly Lys Glu Val His Ser Gly Val Cys Thr Asp Pro Gln Pro Leu Lys
                165                 170                 175

Glu Gln Pro Ala Leu Asn Asp Ser Arg Tyr Ala Leu Ser Ser Arg Leu
```

```
                180                 185                 190
Arg Val Ser Ala Thr Phe Trp Gln Asp Pro Arg Asn His Phe Arg Cys
            195                 200                 205

Gln Val Gln Phe Tyr Gly Leu Ser Glu Asn Asp Glu Trp Thr Gln Asp
        210                 215                 220

Arg Ala Lys Pro Val Thr Gln Ile Val Ser Ala Glu Ala Trp Gly Arg
225                 230                 235                 240

Ala Asp

<210> SEQ ID NO 38
<211> LENGTH: 9
<212> TYPE: PRT
<213> ORGANISM: Homo sapiens

<400> SEQUENCE: 38

Ser Leu Leu Met Trp Ile Thr Gln Cys
1               5

<210> SEQ ID NO 39
<211> LENGTH: 81
<212> TYPE: PRT
<213> ORGANISM: artificial
<220> FEATURE:
<223> OTHER INFORMATION: artificial TCR of alpha and beta chains
      separated by an internal self-cleaving porcine teschovirus 2A
      sequence that binds a human herpesvirus-5 or cytomegalovirus (CMV)
      antigen

<400> SEQUENCE: 39

Met Glu Lys Asn Pro Leu Ala Ala Pro Leu Leu Ile Leu Trp Phe His
1               5                   10                  15

Leu Asp Cys Val Ser Ile Leu Asn Val Glu Gln Ser Pro Gln Ser Leu
            20                  25                  30

His Val Gln Glu Gly Asp Ser Thr Asn Phe Thr Cys Ser Phe Pro Ser
        35                  40                  45

Ser Asn Phe Tyr Ala Leu His Trp Tyr Arg Trp Glu Thr Ala Lys Ser
    50                  55                  60

Pro Glu Ala Leu Phe Val Met Thr Leu Asn Gly Asp Glu Lys Lys Lys
65                  70                  75                  80

Gly

<210> SEQ ID NO 40
<211> LENGTH: 327
<212> TYPE: DNA
<213> ORGANISM: Homo sapiens

<400> SEQUENCE: 40
ttcagcagaa gcgccgacgc ccctgcctac cagcagggcc agaatcagct gtacaacgag      60
ctgaacctgg gcagaaggga agagtacgac gtcctggata gcggagaggc cgggaccct     120 gagatgggcg gcaagcctcg gcggaagaac ccccaggaag gcctgtataa cgaactgcag     180
aaagacaaga tggccgaggc ctacagcgag atcggcatga agggcgagcg gaggcggggc     240
aagggccacg acggcctgta tcagggcctg tccaccgcca ccaaggatac ctacgacgcc     300
ctgcacatgc aggccctgcc cccaagg                                         327

<210> SEQ ID NO 41
<211> LENGTH: 10
<212> TYPE: PRT
<213> ORGANISM: artificial
```

```
<220> FEATURE:
<223> OTHER INFORMATION: CDRH1 of variable domain of heavy chain of
      TNX-355 anti-CD4 antibody

<400> SEQUENCE: 41

Gly Tyr Thr Phe Thr Ser Tyr Val Ile His
1               5                   10

<210> SEQ ID NO 42
<211> LENGTH: 17
<212> TYPE: PRT
<213> ORGANISM: artificial
<220> FEATURE:
<223> OTHER INFORMATION: CDRH2 of variable domain of heavy chain of
      TNX-355 anti-CD4 antibody

<400> SEQUENCE: 42

Tyr Ile Asn Pro Tyr Asn Asp Gly Thr Asp Tyr Asp Glu Lys Phe Lys
1               5                   10                  15

Gly

<210> SEQ ID NO 43
<211> LENGTH: 13
<212> TYPE: PRT
<213> ORGANISM: artificial
<220> FEATURE:
<223> OTHER INFORMATION: CDRH3 of variable domain of heavy chain of
      TNX-355 anti-CD4 antibody

<400> SEQUENCE: 43

Glu Lys Asp Asn Tyr Ala Thr Gly Ala Trp Phe Ala Tyr
1               5                   10

<210> SEQ ID NO 44
<211> LENGTH: 17
<212> TYPE: PRT
<213> ORGANISM: artificial
<220> FEATURE:
<223> OTHER INFORMATION: CDRL1 of variable domain of light chain of
      TNX-355 anti-CD4 antibody

<400> SEQUENCE: 44

Lys Ser Ser Gln Ser Leu Leu Tyr Ser Thr Asn Gln Lys Asn Tyr Leu
1               5                   10                  15

Ala

<210> SEQ ID NO 45
<211> LENGTH: 7
<212> TYPE: PRT
<213> ORGANISM: artificial
<220> FEATURE:
<223> OTHER INFORMATION: CDRL2 of variable domain of light chain of
      TNX-355 anti-CD4 antibody

<400> SEQUENCE: 45

Trp Ala Ser Thr Arg Glu Ser
1               5

<210> SEQ ID NO 46
<211> LENGTH: 8
<212> TYPE: PRT
<213> ORGANISM: artificial
<220> FEATURE:
<223> OTHER INFORMATION: CDRL3 of variable domain of light chain of
      TNX-355 anti-CD4 antibody

<400> SEQUENCE: 46
```

```
Gln Gln Tyr Tyr Ser Tyr Arg Thr
1               5

<210> SEQ ID NO 47
<211> LENGTH: 7
<212> TYPE: PRT
<213> ORGANISM: artificial
<220> FEATURE:
<223> OTHER INFORMATION: CDRH1 of variable domain of heavy chain of OKT8
      anti-CD8 antibody

<400> SEQUENCE: 47

Phe Asn Ile Lys Asp Thr Tyr
1               5

<210> SEQ ID NO 48
<211> LENGTH: 6
<212> TYPE: PRT
<213> ORGANISM: artificial
<220> FEATURE:
<223> OTHER INFORMATION: CDRH2 of variable domain of heavy chain of OKT8
      anti-CD8 antibody

<400> SEQUENCE: 48

Asp Pro Ala Asn Asp Asn
1               5

<210> SEQ ID NO 49
<211> LENGTH: 9
<212> TYPE: PRT
<213> ORGANISM: artificial
<220> FEATURE:
<223> OTHER INFORMATION: CDRH3 of variable domain of heavy chain of OKT8
      anti-CD8 antibody

<400> SEQUENCE: 49

Gly Tyr Gly Tyr Tyr Val Phe Asp His
1               5

<210> SEQ ID NO 50
<211> LENGTH: 6
<212> TYPE: PRT
<213> ORGANISM: artificial
<220> FEATURE:
<223> OTHER INFORMATION: CDRL1 of variable domain of light chain of OKT8
      anti-CD8 antibody

<400> SEQUENCE: 50

Arg Ser Ile Ser Gln Tyr
1               5

<210> SEQ ID NO 51
<211> LENGTH: 7
<212> TYPE: PRT
<213> ORGANISM: artificial
<220> FEATURE:
<223> OTHER INFORMATION: CDRL2 of variable domain of light chain of OKT8
      anti-CD8 antibody

<400> SEQUENCE: 51

Ser Gly Ser Thr Leu Gln Ser
1               5

<210> SEQ ID NO 52
<211> LENGTH: 7
<212> TYPE: PRT
<213> ORGANISM: artificial
```

```
<220> FEATURE:
<223> OTHER INFORMATION: CDRL3 of variable domain of light chain of OKT8
      anti-CD8 antibody

<400> SEQUENCE: 52

His Asn Glu Asn Pro Leu Thr
1               5

<210> SEQ ID NO 53
<211> LENGTH: 5
<212> TYPE: PRT
<213> ORGANISM: artificial
<220> FEATURE:
<223> OTHER INFORMATION: CDRH1 of variable domain of heavy chain of OKT3
      anti-CD3 antibody

<400> SEQUENCE: 53

Arg Tyr Thr Met His
1               5

<210> SEQ ID NO 54
<211> LENGTH: 17
<212> TYPE: PRT
<213> ORGANISM: artificial
<220> FEATURE:
<223> OTHER INFORMATION: CDRH2 of variable domain of heavy chain of OKT3
      anti-CD3 antibody

<400> SEQUENCE: 54

Tyr Ile Asn Pro Ser Arg Gly Tyr Thr Asn Tyr Asn Gln Lys Phe Lys
1               5                   10                  15

Asp

<210> SEQ ID NO 55
<211> LENGTH: 10
<212> TYPE: PRT
<213> ORGANISM: artificial
<220> FEATURE:
<223> OTHER INFORMATION: CDRH3 of variable domain of heavy chain of OKT3
      anti-CD3 antibody

<400> SEQUENCE: 55

Tyr Tyr Asp Asp His Tyr Cys Leu Asp Tyr
1               5                   10

<210> SEQ ID NO 56
<211> LENGTH: 10
<212> TYPE: PRT
<213> ORGANISM: artificial
<220> FEATURE:
<223> OTHER INFORMATION: CDRL1 of variable domain of light chain of OKT3
      anti-CD3 antibody

<400> SEQUENCE: 56

Ser Ala Ser Ser Ser Val Ser Tyr Met Asn
1               5                   10

<210> SEQ ID NO 57
<211> LENGTH: 7
<212> TYPE: PRT
<213> ORGANISM: artificial
<220> FEATURE:
<223> OTHER INFORMATION: CDRL2 of variable domain of light chain of OKT3
      anti-CD3 antibody

<400> SEQUENCE: 57

Asp Thr Ser Lys Leu Ala Ser
```

-continued

```
<210> SEQ ID NO 58
<211> LENGTH: 9
<212> TYPE: PRT
<213> ORGANISM: artificial
<220> FEATURE:
<223> OTHER INFORMATION: CDRL3 of variable domain of light chain of OKT3
      anti-CD3 antibody

<400> SEQUENCE: 58

Gln Gln Trp Ser Ser Asn Pro Phe Thr
1               5

<210> SEQ ID NO 59
<211> LENGTH: 16
<212> TYPE: PRT
<213> ORGANISM: unknown
<220> FEATURE:
<223> OTHER INFORMATION: hydrophobic membrane translocation sequence-
      containing peptide

<400> SEQUENCE: 59

Ala Ala Val Ala Leu Leu Pro Ala Val Leu Leu Ala Leu Leu Ala Pro
1               5                   10                  15

<210> SEQ ID NO 60
<211> LENGTH: 11
<212> TYPE: PRT
<213> ORGANISM: unknown
<220> FEATURE:
<223> OTHER INFORMATION: hydrophobic membrane translocation sequence-
      containing peptide

<400> SEQUENCE: 60

Ala Ala Leu Leu Pro Val Leu Leu Ala Ala Pro
1               5                   10

<210> SEQ ID NO 61
<211> LENGTH: 16
<212> TYPE: PRT
<213> ORGANISM: Influenza virus

<400> SEQUENCE: 61

Gly Leu Phe Glu Ala Ile Ala Gly Phe Ile Glu Asn Gly Trp Glu Gly
1               5                   10                  15

<210> SEQ ID NO 62
<211> LENGTH: 11
<212> TYPE: PRT
<213> ORGANISM: Human immunodeficiency virus

<400> SEQUENCE: 62

Tyr Gly Arg Lys Lys Arg Arg Gln Arg Arg Arg
1               5                   10

<210> SEQ ID NO 63
<211> LENGTH: 16
<212> TYPE: PRT
<213> ORGANISM: Duck hepatitis B virus

<400> SEQUENCE: 63

Met Ser Gly Thr Phe Gly Gly Ile Leu Ala Gly Leu Ile Gly Leu Leu
1               5                   10                  15

<210> SEQ ID NO 64
```

```
<211> LENGTH: 16
<212> TYPE: PRT
<213> ORGANISM: Woodchuck hepatitis B virus

<400> SEQUENCE: 64

Met Ser Pro Ser Ser Leu Leu Gly Leu Leu Ala Gly Leu Gln Val Val
1               5                   10                  15

<210> SEQ ID NO 65
<211> LENGTH: 17
<212> TYPE: PRT
<213> ORGANISM: artificial
<220> FEATURE:
<223> OTHER INFORMATION: synthetic exemplary endosomal release agent

<400> SEQUENCE: 65

Gly Leu Phe Glu Ala Leu Leu Glu Leu Leu Glu Ser Leu Trp Glu Leu
1               5                   10                  15

Leu

<210> SEQ ID NO 66
<211> LENGTH: 16
<212> TYPE: PRT
<213> ORGANISM: artificial
<220> FEATURE:
<223> OTHER INFORMATION: synthetic exemplary endosomal release agent

<400> SEQUENCE: 66

Leu Lys Lys Leu Leu Lys Lys Leu Leu Lys Lys Leu Leu Lys Lys Leu
1               5                   10                  15

<210> SEQ ID NO 67
<211> LENGTH: 16
<212> TYPE: PRT
<213> ORGANISM: unknown
<220> FEATURE:
<223> OTHER INFORMATION: exemplary endosomal release agent

<400> SEQUENCE: 67

Arg Gln Ile Lys Ile Trp Phe Gln Asn Arg Arg Met Lys Trp Lys Lys
1               5                   10                  15

<210> SEQ ID NO 68
<211> LENGTH: 14
<212> TYPE: PRT
<213> ORGANISM: unknown
<220> FEATURE:
<223> OTHER INFORMATION: Tat fragment - exemplary endosomal release
      agent

<400> SEQUENCE: 68

Gly Arg Lys Lys Arg Arg Gln Arg Arg Pro Pro Gln Cys
1               5                   10

<210> SEQ ID NO 69
<211> LENGTH: 27
<212> TYPE: PRT
<213> ORGANISM: unknown
<220> FEATURE:
<223> OTHER INFORMATION: exemplary endosomal release agent

<400> SEQUENCE: 69

Gly Ala Leu Phe Leu Gly Trp Leu Gly Ala Ala Gly Ser Thr Met Gly
1               5                   10                  15

Ala Trp Ser Gln Pro Lys Lys Arg Lys Val
            20                  25
```

```
<210> SEQ ID NO 70
<211> LENGTH: 18
<212> TYPE: PRT
<213> ORGANISM: unknown
<220> FEATURE:
<223> OTHER INFORMATION: PVEC - exemplary endosomal release agent

<400> SEQUENCE: 70

Leu Leu Ile Ile Leu Arg Arg Arg Ile Arg Lys Gln Ala His Ala His
1               5                   10                  15

Ser Lys

<210> SEQ ID NO 71
<211> LENGTH: 26
<212> TYPE: PRT
<213> ORGANISM: unknown
<220> FEATURE:
<223> OTHER INFORMATION: transportan - exemplary endosomal release agent

<400> SEQUENCE: 71

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 72
<211> LENGTH: 18
<212> TYPE: PRT
<213> ORGANISM: artificial
<220> FEATURE:
<223> OTHER INFORMATION: amphiphilic model peptide - exemplary endosomal
      release agent

<400> SEQUENCE: 72

Lys Leu Ala Leu Lys Leu Ala Leu Lys Ala Leu Lys Ala Ala Leu Lys
1               5                   10                  15

Leu Ala

<210> SEQ ID NO 73
<211> LENGTH: 9
<212> TYPE: PRT
<213> ORGANISM: artificial
<220> FEATURE:
<223> OTHER INFORMATION: Arg9 - exemplary endosomal release agent

<400> SEQUENCE: 73

Arg Arg Arg Arg Arg Arg Arg Arg Arg
1               5

<210> SEQ ID NO 74
<211> LENGTH: 37
<212> TYPE: PRT
<213> ORGANISM: unknown
<220> FEATURE:
<223> OTHER INFORMATION: LL-37, exemplary endosomal release agent

<400> SEQUENCE: 74

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
            35
```

```
<210> SEQ ID NO 75
<211> LENGTH: 31
<212> TYPE: PRT
<213> ORGANISM: unknown
<220> FEATURE:
<223> OTHER INFORMATION: Cecropin P1 - exemplary endosomal release agent

<400> SEQUENCE: 75

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 76
<211> LENGTH: 30
<212> TYPE: PRT
<213> ORGANISM: unknown
<220> FEATURE:
<223> OTHER INFORMATION: alpha-defensin - exemplary endosomal release
      agent

<400> SEQUENCE: 76

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 77
<211> LENGTH: 36
<212> TYPE: PRT
<213> ORGANISM: unknown
<220> FEATURE:
<223> OTHER INFORMATION: beta-defensin - exemplary endosomal release
      agent

<400> SEQUENCE: 77

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
        35

<210> SEQ ID NO 78
<211> LENGTH: 12
<212> TYPE: PRT
<213> ORGANISM: unknown
<220> FEATURE:
<223> OTHER INFORMATION: bactenecin - exemplary endosomal release agent

<400> SEQUENCE: 78

Arg Lys Cys Arg Ile Val Val Ile Arg Val Cys Arg
1               5                   10

<210> SEQ ID NO 79
<211> LENGTH: 42
<212> TYPE: PRT
<213> ORGANISM: unknown
<220> FEATURE:
<223> OTHER INFORMATION: PR-3, amidated at the C-terminus, exemplary
      endosomal release agent

<400> SEQUENCE: 79

Arg Arg Arg Pro Arg Pro Pro Tyr Leu Pro Arg Pro Arg Pro Pro Pro
```

```
                1               5                   10                  15
Phe Phe Pro Pro Arg Leu Pro Pro Arg Ile Pro Pro Gly Phe Pro Pro
                20                  25                  30

Arg Phe Pro Pro Arg Phe Pro Gly Lys Arg
        35                  40

<210> SEQ ID NO 80
<211> LENGTH: 13
<212> TYPE: PRT
<213> ORGANISM: unknown
<220> FEATURE:
<223> OTHER INFORMATION: indolicidin - exemplary endosomal release
      agent, amidated at the C-terminus

<400> SEQUENCE: 80

Ile Leu Pro Trp Lys Trp Pro Trp Trp Pro Trp Arg Arg
1               5                   10

<210> SEQ ID NO 81
<211> LENGTH: 27
<212> TYPE: PRT
<213> ORGANISM: unknown
<220> FEATURE:
<223> OTHER INFORMATION: Microtubule-associated sequence (MTAS),
      exemplary nuclear targeting agent

<400> SEQUENCE: 81

Pro Leu Lys Thr Pro Gly Lys Lys Lys Lys Gly Lys Pro Gly Lys Arg
1               5                   10                  15

Lys Glu Gln Glu Lys Lys Arg Arg Thr Arg
            20                  25

<210> SEQ ID NO 82
<211> LENGTH: 30
<212> TYPE: PRT
<213> ORGANISM: unknown
<220> FEATURE:
<223> OTHER INFORMATION: exemplary nuclear localization signal (NLS)
      sequence

<400> SEQUENCE: 82

Gly Arg Tyr Leu Thr Gln Glu Thr Asn Lys Val Glu Thr Tyr Lys Glu
1               5                   10                  15

Gln Pro Leu Lys Thr Pro Gly Lys Lys Lys Gly Lys Pro
            20                  25                  30

<210> SEQ ID NO 83
<211> LENGTH: 44
<212> TYPE: PRT
<213> ORGANISM: unknown
<220> FEATURE:
<223> OTHER INFORMATION: exemplary nuclear targeting agent that includes
      overlapping MTAS and NLS sequences

<400> SEQUENCE: 83

Gly Arg Tyr Leu Thr Gln Glu Thr Asn Lys Val Glu Thr Tyr Lys Glu
1               5                   10                  15

Gln Pro Leu Lys Thr Pro Gly Lys Lys Lys Gly Lys Pro Gly Lys
            20                  25                  30

Arg Lys Glu Gln Glu Lys Lys Arg Arg Thr Arg
        35                  40

<210> SEQ ID NO 84
<211> LENGTH: 7
```

```
<212> TYPE: PRT
<213> ORGANISM: Simian virus 40

<400> SEQUENCE: 84

Pro Lys Lys Lys Arg Lys Val
1               5

<210> SEQ ID NO 85
<211> LENGTH: 16
<212> TYPE: PRT
<213> ORGANISM: Xenopus
<220> FEATURE:
<221> NAME/KEY: MISC_FEATURE
<222> LOCATION: (3)..(12)
<223> OTHER INFORMATION: Xaa can be any amino acid

<400> SEQUENCE: 85

Lys Arg Xaa Xaa Xaa Xaa Xaa Xaa Xaa Xaa Xaa Lys Lys Lys Leu
1               5                   10                  15

<210> SEQ ID NO 86
<211> LENGTH: 7
<212> TYPE: PRT
<213> ORGANISM: artificial
<220> FEATURE:
<223> OTHER INFORMATION: SV40 T-Ag-derived NLS peptide

<400> SEQUENCE: 86

Pro Lys Lys Lys Arg Lys Val
1               5

<210> SEQ ID NO 87
<211> LENGTH: 7
<212> TYPE: PRT
<213> ORGANISM: artificial
<220> FEATURE:
<223> OTHER INFORMATION: SV40 T-Ag-derived NLS peptide

<400> SEQUENCE: 87

Pro Lys Lys Lys Arg Met Val
1               5

<210> SEQ ID NO 88
<211> LENGTH: 10
<212> TYPE: PRT
<213> ORGANISM: artificial
<220> FEATURE:
<223> OTHER INFORMATION: SV40 T-Ag-derived NLS peptide

<400> SEQUENCE: 88

Pro Lys Lys Lys Arg Lys Val Glu Asp Pro
1               5                   10

<210> SEQ ID NO 89
<211> LENGTH: 8
<212> TYPE: PRT
<213> ORGANISM: artificial
<220> FEATURE:
<223> OTHER INFORMATION: SV40 T-Ag-derived NLS peptide

<400> SEQUENCE: 89

Pro Lys Lys Gly Ser Lys Lys Ala
1               5

<210> SEQ ID NO 90
<211> LENGTH: 7
<212> TYPE: PRT
```

```
<213> ORGANISM: artificial
<220> FEATURE:
<223> OTHER INFORMATION: SV40 T-Ag-derived NLS peptide

<400> SEQUENCE: 90

Pro Lys Thr Lys Arg Lys Val
1               5

<210> SEQ ID NO 91
<211> LENGTH: 11
<212> TYPE: PRT
<213> ORGANISM: artificial
<220> FEATURE:
<223> OTHER INFORMATION: SV40 T-Ag-derived NLS peptide

<400> SEQUENCE: 91

Cys Gly Gly Pro Lys Lys Lys Arg Lys Val Gly
1               5                   10

<210> SEQ ID NO 92
<211> LENGTH: 7
<212> TYPE: PRT
<213> ORGANISM: artificial
<220> FEATURE:
<223> OTHER INFORMATION: SV40 T-Ag-derived NLS peptide

<400> SEQUENCE: 92

Pro Lys Lys Lys Ile Lys Val
1               5

<210> SEQ ID NO 93
<211> LENGTH: 34
<212> TYPE: PRT
<213> ORGANISM: artificial
<220> FEATURE:
<223> OTHER INFORMATION: SV40 T-Ag-derived NLS peptide

<400> SEQUENCE: 93

Cys Tyr Asp Asp Glu Ala Thr Ala Asp Ser Gln His Ser Thr Pro Pro
1               5                   10                  15

Lys Lys Lys Arg Lys Val Glu Asp Pro Lys Asp Phe Glu Ser Glu Leu
            20                  25                  30

Leu Ser

<210> SEQ ID NO 94
<211> LENGTH: 13
<212> TYPE: PRT
<213> ORGANISM: artificial
<220> FEATURE:
<223> OTHER INFORMATION: SV40 T-Ag-derived NLS peptide

<400> SEQUENCE: 94

Cys Gly Tyr Gly Pro Lys Lys Lys Arg Lys Val Gly Gly
1               5                   10

<210> SEQ ID NO 95
<211> LENGTH: 7
<212> TYPE: PRT
<213> ORGANISM: Polyoma virus

<400> SEQUENCE: 95

Pro Lys Lys Ala Arg Glu Asp
1               5

<210> SEQ ID NO 96
```

```
<211> LENGTH: 13
<212> TYPE: PRT
<213> ORGANISM: Polyoma virus

<400> SEQUENCE: 96

Cys Gly Tyr Gly Val Ser Arg Lys Arg Pro Arg Pro Gly
1               5                   10

<210> SEQ ID NO 97
<211> LENGTH: 8
<212> TYPE: PRT
<213> ORGANISM: Simian virus 40

<400> SEQUENCE: 97

Ala Pro Thr Lys Arg Lys Gly Ser
1               5

<210> SEQ ID NO 98
<211> LENGTH: 11
<212> TYPE: PRT
<213> ORGANISM: Polyoma virus

<400> SEQUENCE: 98

Ala Pro Lys Arg Lys Ser Gly Val Ser Lys Cys
1               5                   10

<210> SEQ ID NO 99
<211> LENGTH: 7
<212> TYPE: PRT
<213> ORGANISM: Simian virus 40

<400> SEQUENCE: 99

Pro Asn Lys Lys Lys Arg Lys
1               5

<210> SEQ ID NO 100
<211> LENGTH: 12
<212> TYPE: PRT
<213> ORGANISM: Polyoma virus

<400> SEQUENCE: 100

Glu Glu Asp Gly Pro Gln Lys Lys Lys Arg Arg Leu
1               5                   10

<210> SEQ ID NO 101
<211> LENGTH: 7
<212> TYPE: PRT
<213> ORGANISM: Unknown
<220> FEATURE:
<223> OTHER INFORMATION: exemplary nuclear localization sequence from
      yeast histone H2B

<400> SEQUENCE: 101

Gly Lys Lys Arg Ser Lys Ala
1               5

<210> SEQ ID NO 102
<211> LENGTH: 5
<212> TYPE: PRT
<213> ORGANISM: Adenovirus E1a

<400> SEQUENCE: 102

Lys Arg Pro Arg Pro
1               5
```

```
<210> SEQ ID NO 103
<211> LENGTH: 11
<212> TYPE: PRT
<213> ORGANISM: Adenovirus type 2/5 E1a

<400> SEQUENCE: 103

Cys Gly Gly Leu Ser Ser Lys Arg Pro Arg Pro
1               5                   10

<210> SEQ ID NO 104
<211> LENGTH: 12
<212> TYPE: PRT
<213> ORGANISM: Xenopus

<400> SEQUENCE: 104

Leu Lys Asp Lys Asp Ala Lys Lys Ser Lys Gln Glu
1               5                   10

<210> SEQ ID NO 105
<211> LENGTH: 10
<212> TYPE: PRT
<213> ORGANISM: unknown
<220> FEATURE:
<223> OTHER INFORMATION: v-Rel or p59v-rel, exemplary NLS

<400> SEQUENCE: 105

Gly Asn Lys Ala Lys Arg Gln Arg Ser Thr
1               5                   10

<210> SEQ ID NO 106
<211> LENGTH: 11
<212> TYPE: PRT
<213> ORGANISM: Influenza A

<400> SEQUENCE: 106

Pro Phe Leu Asp Arg Leu Arg Arg Asp Gln Lys
1               5                   10

<210> SEQ ID NO 107
<211> LENGTH: 9
<212> TYPE: PRT
<213> ORGANISM: Homo sapiens

<400> SEQUENCE: 107

Ser Val Thr Lys Lys Arg Lys Leu Glu
1               5

<210> SEQ ID NO 108
<211> LENGTH: 9
<212> TYPE: PRT
<213> ORGANISM: Xenopus

<400> SEQUENCE: 108

Ser Ala Ser Lys Arg Arg Arg Leu Glu
1               5

<210> SEQ ID NO 109
<211> LENGTH: 11
<212> TYPE: PRT
<213> ORGANISM: Adenovirus 5

<400> SEQUENCE: 109

Pro Pro Lys Lys Arg Met Arg Arg Arg Ile Glu
1               5                   10
```

```
<210> SEQ ID NO 110
<211> LENGTH: 28
<212> TYPE: PRT
<213> ORGANISM: Rat

<400> SEQUENCE: 110

Tyr Arg Lys Cys Leu Gln Ala Gly Met Asn Leu Glu Ala Arg Lys Thr
1               5                   10                  15

Lys Lys Lys Ile Lys Gly Ile Gln Gln Ala Thr Ala
            20                  25

<210> SEQ ID NO 111
<211> LENGTH: 54
<212> TYPE: PRT
<213> ORGANISM: Homo sapiens

<400> SEQUENCE: 111

Arg Lys Asp Arg Arg Gly Gly Arg Met Leu Lys His Lys Arg Gln Arg
1               5                   10                  15

Asp Asp Gly Glu Gly Arg Gly Glu Val Gly Ser Ala Gly Asp Met Arg
            20                  25                  30

Ala Met Ile Asn Ala Cys Ile Asp Asn Leu Trp Pro Ser Pro Leu Met
        35                  40                  45

Ile Lys Arg Ser Lys Lys
    50

<210> SEQ ID NO 112
<211> LENGTH: 8
<212> TYPE: PRT
<213> ORGANISM: Rabbit

<400> SEQUENCE: 112

Arg Lys Phe Lys Lys Phe Asn Lys
1               5

<210> SEQ ID NO 113
<211> LENGTH: 8
<212> TYPE: PRT
<213> ORGANISM: unknown
<220> FEATURE:
<223> OTHER INFORMATION: from c-myb gene product, exemplary NLS

<400> SEQUENCE: 113

Pro Leu Leu Lys Lys Ile Lys Gln
1               5

<210> SEQ ID NO 114
<211> LENGTH: 8
<212> TYPE: PRT
<213> ORGANISM: unknown
<220> FEATURE:
<223> OTHER INFORMATION: from N-myc gene product, exemplary NLS

<400> SEQUENCE: 114

Pro Pro Gln Lys Lys Ile Lys Ser
1               5

<210> SEQ ID NO 115
<211> LENGTH: 7
<212> TYPE: PRT
<213> ORGANISM: unknown
<220> FEATURE:
<223> OTHER INFORMATION: from p53, exemplary NLS

<400> SEQUENCE: 115
```

```
Pro Gln Pro Lys Lys Lys Pro
1               5
```

<210> SEQ ID NO 116
<211> LENGTH: 9
<212> TYPE: PRT
<213> ORGANISM: unknown
<220> FEATURE:
<223> OTHER INFORMATION: from c-erb-A gene product, exemplary NLS

<400> SEQUENCE: 116

```
Ser Lys Arg Val Ala Lys Arg Lys Leu
1               5
```

<210> SEQ ID NO 117
<211> LENGTH: 14
<212> TYPE: PRT
<213> ORGANISM: Unknown
<220> FEATURE:
<223> OTHER INFORMATION: exemplary nuclear localization sequence from
      yeast ribosomal protein L29

<400> SEQUENCE: 117

```
Met Thr Gly Ser Lys Thr Arg Lys His Arg Gly Ser Gly Ala
1               5                   10
```

<210> SEQ ID NO 118
<211> LENGTH: 6
<212> TYPE: PRT
<213> ORGANISM: Unknown
<220> FEATURE:
<223> OTHER INFORMATION: exemplary nuclear localization sequence from
      yeast ribosomal protein L29

<400> SEQUENCE: 118

```
Arg His Arg Lys His Pro
1               5
```

<210> SEQ ID NO 119
<211> LENGTH: 6
<212> TYPE: PRT
<213> ORGANISM: Unknown
<220> FEATURE:
<223> OTHER INFORMATION: exemplary nuclear localization sequence from
      yeast ribosomal protein L29

<400> SEQUENCE: 119

```
Lys Arg Arg Lys His Pro
1               5
```

<210> SEQ ID NO 120
<211> LENGTH: 6
<212> TYPE: PRT
<213> ORGANISM: Unknown
<220> FEATURE:
<223> OTHER INFORMATION: exemplary nuclear localization sequence from
      yeast ribosomal protein L29

<400> SEQUENCE: 120

```
Lys Tyr Arg Lys His Pro
1               5
```

<210> SEQ ID NO 121
<211> LENGTH: 6
<212> TYPE: PRT
<213> ORGANISM: Unknown
<220> FEATURE:

<223> OTHER INFORMATION: exemplary nuclear localization sequence from
      yeast ribosomal protein L29

<400> SEQUENCE: 121

Lys His Arg Arg His Pro
1               5

<210> SEQ ID NO 122
<211> LENGTH: 6
<212> TYPE: PRT
<213> ORGANISM: Unknown
<220> FEATURE:
<223> OTHER INFORMATION: exemplary nuclear localization sequence from
      yeast ribosomal protein L29

<400> SEQUENCE: 122

Lys His Lys Lys His Pro
1               5

<210> SEQ ID NO 123
<211> LENGTH: 6
<212> TYPE: PRT
<213> ORGANISM: Unknown
<220> FEATURE:
<223> OTHER INFORMATION: exemplary nuclear localization sequence from
      yeast ribosomal protein L29

<400> SEQUENCE: 123

Arg His Leu Lys His Pro
1               5

<210> SEQ ID NO 124
<211> LENGTH: 33
<212> TYPE: PRT
<213> ORGANISM: Hepatitis B

<400> SEQUENCE: 124

Pro Glu Thr Thr Val Val Arg Arg Arg Gly Arg Ser Pro Arg Arg
1               5                   10                  15

Thr Pro Ser Pro Arg Arg Arg Arg Ser Pro Arg Arg Arg Ser Gln
            20                  25                  30

Ser

<210> SEQ ID NO 125
<211> LENGTH: 9
<212> TYPE: PRT
<213> ORGANISM: unknown
<220> FEATURE:
<223> OTHER INFORMATION: from viral jun, exemplary NLS

<400> SEQUENCE: 125

Ala Ser Lys Ser Arg Lys Arg Lys Leu
1               5

<210> SEQ ID NO 126
<211> LENGTH: 16
<212> TYPE: PRT
<213> ORGANISM: Human T cell leukemia virus

<400> SEQUENCE: 126

Gly Gly Leu Cys Ser Ala Arg Leu His Arg His Ala Leu Leu Ala Thr
1               5                   10                  15

<210> SEQ ID NO 127
<211> LENGTH: 18

```
<212> TYPE: PRT
<213> ORGANISM: Mouse

<400> SEQUENCE: 127

Asp Thr Arg Glu Lys Lys Phe Leu Lys Arg Leu Leu Arg Leu
1               5                   10                  15

Asp Glu

<210> SEQ ID NO 128
<211> LENGTH: 32
<212> TYPE: PRT
<213> ORGANISM: Virus

<400> SEQUENCE: 128

Val Gly Phe Pro Val Thr Pro Gln Val Pro Leu Arg Pro Met Thr Tyr
1               5                   10                  15

Lys Ala Ala Val Asp Leu Ser His Phe Leu Lys Glu Lys Gly Gly Leu
                20                  25                  30

<210> SEQ ID NO 129
<211> LENGTH: 30
<212> TYPE: PRT
<213> ORGANISM: Virus

<400> SEQUENCE: 129

His Thr Gln Gly Tyr Phe Pro Asp Trp Gln Asn Tyr Thr Pro Gly Pro
1               5                   10                  15

Gly Val Arg Tyr Pro Leu Thr Phe Gly Trp Leu Tyr Lys Leu
                20                  25                  30

<210> SEQ ID NO 130
<211> LENGTH: 19
<212> TYPE: PRT
<213> ORGANISM: Virus

<400> SEQUENCE: 130

Glu Lys Ile Arg Leu Arg Pro Gly Gly Lys Lys Tyr Lys Leu Lys
1               5                   10                  15

His Ile Val

<210> SEQ ID NO 131
<211> LENGTH: 32
<212> TYPE: PRT
<213> ORGANISM: Virus

<400> SEQUENCE: 131

Asn Pro Pro Ile Pro Val Gly Glu Ile Tyr Lys Arg Trp Ile Ile Leu
1               5                   10                  15

Gly Leu Asn Lys Ile Val Arg Met Tyr Ser Pro Thr Ser Ile Leu Asp
                20                  25                  30

<210> SEQ ID NO 132
<211> LENGTH: 31
<212> TYPE: PRT
<213> ORGANISM: Virus

<400> SEQUENCE: 132

Ala Ile Phe Gln Ser Ser Met Thr Lys Ile Leu Glu Pro Phe Arg Lys
1               5                   10                  15

Gln Asn Pro Asp Ile Val Ile Tyr Gln Tyr Met Asp Asp Leu Tyr
                20                  25                  30
```

-continued

<210> SEQ ID NO 133
<211> LENGTH: 20
<212> TYPE: PRT
<213> ORGANISM: Virus

<400> SEQUENCE: 133

Asn Ala Asn Pro Asn Ala Asn Pro Asn Ala Asn Pro Asn Ala Asn Pro
1               5                   10                  15

Asn Ala Asn Pro
            20

<210> SEQ ID NO 134
<211> LENGTH: 81
<212> TYPE: PRT
<213> ORGANISM: Virus

<400> SEQUENCE: 134

Ala Phe Thr Phe Thr Lys Ile Pro Ala Glu Thr Leu His Val Thr
1               5                   10                  15

Glu Val Gln Tyr Ala Gly Thr Asp Gly Pro Cys Lys Val Pro Ala Gln
            20                  25                  30

Met Ala Val Asp Met Gln Thr Leu Thr Pro Val Gly Arg Leu Ile Thr
        35                  40                  45

Ala Asn Pro Val Ile Thr Glu Gly Thr Glu Asn Ser Lys Met Met Leu
    50                  55                  60

Glu Leu Asp Pro Pro Phe Gly Asp Ser Tyr Ile Val Ile Gly Val Gly
65                  70                  75                  80

Glu

<210> SEQ ID NO 135
<211> LENGTH: 750
<212> TYPE: PRT
<213> ORGANISM: unknown
<220> FEATURE:
<223> OTHER INFORMATION: PSMA cancer vaccine antigen

<400> SEQUENCE: 135

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

-continued

```
Phe Ser Ala Phe Ser Pro Gln Gly Met Pro Glu Gly Asp Leu Val Tyr
                165                 170                 175
Val Asn Tyr Ala Arg Thr Glu Asp Phe Phe Lys Leu Glu Arg Asp Met
            180                 185                 190
Lys Ile Asn Cys Ser Gly Lys Ile Val Ile Ala Arg Tyr Gly Lys Val
        195                 200                 205
Phe Arg Gly Asn Lys Val Lys Asn Ala Gln Leu Ala Gly Ala Lys Gly
    210                 215                 220
Val Ile Leu Tyr Ser Asp Pro Ala Asp Tyr Phe Ala Pro Gly Val Lys
225                 230                 235                 240
Ser Tyr Pro Asp Gly Trp Asn Leu Pro Gly Gly Val Gln Arg Gly
                245                 250                 255
Asn Ile Leu Asn Leu Asn Gly Ala Gly Asp Pro Leu Thr Pro Gly Tyr
            260                 265                 270
Pro Ala Asn Glu Tyr Ala Tyr Arg Arg Gly Ile Ala Glu Ala Val Gly
        275                 280                 285
Leu Pro Ser Ile Pro Val His Pro Ile Gly Tyr Tyr Asp Ala Gln Lys
    290                 295                 300
Leu Leu Glu Lys Met Gly Gly Ser Ala Pro Pro Asp Ser Ser Trp Arg
305                 310                 315                 320
Gly Ser Leu Lys Val Pro Tyr Asn Val Gly Pro Gly Phe Thr Gly Asn
                325                 330                 335
Phe Ser Thr Gln Lys Val Lys Met His Ile His Ser Thr Asn Glu Val
            340                 345                 350
Thr Arg Ile Tyr Asn Val Ile Gly Thr Leu Arg Gly Ala Val Glu Pro
        355                 360                 365
Asp Arg Tyr Val Ile Leu Gly Gly His Arg Asp Ser Trp Val Phe Gly
    370                 375                 380
Gly Ile Asp Pro Gln Ser Gly Ala Ala Val Val His Glu Ile Val Arg
385                 390                 395                 400
Ser Phe Gly Thr Leu Lys Lys Glu Gly Trp Arg Pro Arg Arg Thr Ile
                405                 410                 415
Leu Phe Ala Ser Trp Asp Ala Glu Glu Phe Gly Leu Leu Gly Ser Thr
            420                 425                 430
Glu Trp Ala Glu Glu Asn Ser Arg Leu Leu Gln Glu Arg Gly Val Ala
        435                 440                 445
Tyr Ile Asn Ala Asp Ser Ser Ile Glu Gly Asn Tyr Thr Leu Arg Val
    450                 455                 460
Asp Cys Thr Pro Leu Met Tyr Ser Leu Val His Asn Leu Thr Lys Glu
465                 470                 475                 480
Leu Lys Ser Pro Asp Glu Gly Phe Glu Gly Lys Ser Leu Tyr Glu Ser
                485                 490                 495
Trp Thr Lys Lys Ser Pro Ser Pro Glu Phe Ser Gly Met Pro Arg Ile
            500                 505                 510
Ser Lys Leu Gly Ser Gly Asn Asp Phe Glu Val Phe Phe Gln Arg Leu
        515                 520                 525
Gly Ile Ala Ser Gly Arg Ala Arg Tyr Thr Lys Asn Trp Glu Thr Asn
    530                 535                 540
Lys Phe Ser Gly Tyr Pro Leu Tyr His Ser Val Tyr Glu Thr Tyr Glu
545                 550                 555                 560
Leu Val Glu Lys Phe Tyr Asp Pro Met Phe Lys Tyr His Leu Thr Val
                565                 570                 575
Ala Gln Val Arg Gly Gly Met Val Phe Glu Leu Ala Asn Ser Ile Val
```

```
                    580                 585                 590
Leu Pro Phe Asp Cys Arg Asp Tyr Ala Val Leu Arg Lys Tyr Ala
            595                 600                 605

Asp Lys Ile Tyr Ser Ile Ser Met Lys His Pro Gln Glu Met Lys Thr
        610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
            645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
            725                 730                 735

Phe Thr Val Gln Ala Ala Ala Glu Thr Leu Ser Glu Val Ala
            740                 745                 750

<210> SEQ ID NO 136
<211> LENGTH: 123
<212> TYPE: PRT
<213> ORGANISM: unknown
<220> FEATURE:
<223> OTHER INFORMATION: PSCA cancer vaccine antigen

<400> SEQUENCE: 136

Met Lys Ala Val Leu Ala Leu Leu Met Ala Gly Leu Ala Leu Gln
1               5                   10                  15

Pro Gly Thr Ala Leu Leu Cys Tyr Ser Cys Lys Ala Gln Val Ser Asn
            20                  25                  30

Glu Asp Cys Leu Gln Val Glu Asn Cys Thr Gln Leu Gly Glu Gln Cys
        35                  40                  45

Trp Thr Ala Arg Ile Arg Ala Val Gly Leu Leu Thr Val Ile Ser Lys
    50                  55                  60

Gly Cys Ser Leu Asn Cys Val Asp Asp Ser Gln Asp Tyr Tyr Val Gly
65                  70                  75                  80

Lys Lys Asn Ile Thr Cys Cys Asp Thr Asp Leu Cys Asn Ala Ser Gly
            85                  90                  95

Ala His Ala Leu Gln Pro Ala Ala Ala Ile Leu Ala Leu Leu Pro Ala
            100                 105                 110

Leu Gly Leu Leu Leu Trp Gly Pro Gly Gln Leu
        115                 120

<210> SEQ ID NO 137
<211> LENGTH: 622
<212> TYPE: PRT
<213> ORGANISM: unknown
<220> FEATURE:
<223> OTHER INFORMATION: Mesothelin cancer vaccine antigen

<400> SEQUENCE: 137

Met Ala Leu Pro Thr Ala Arg Pro Leu Leu Gly Ser Cys Gly Thr Pro
1               5                   10                  15
```

```
Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Phe Leu Asn Pro
        115                 120                 125

Asp Ala Phe Ser Gly Pro Gln Ala Cys Thr His Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
```

```
                435                 440                 445
Leu Ser Ser Val Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540

Pro His Val Glu Gly Leu Lys Ala Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Val Gln Glu Ala Leu Ser Gly Thr Pro Cys Leu Leu Gly Pro Gly Pro
        595                 600                 605

Val Leu Thr Val Leu Ala Leu Leu Leu Ala Ser Thr Leu Ala
    610                 615                 620

<210> SEQ ID NO 138
<211> LENGTH: 556
<212> TYPE: PRT
<213> ORGANISM: unknown
<220> FEATURE:
<223> OTHER INFORMATION: CD19 cancer vaccine antigen

<400> SEQUENCE: 138

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ser
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
```

```
                180             185             190
Gly Ser Thr Leu Trp Leu Ser Cys Gly Val Pro Pro Asp Ser Val Ser
            195                 200             205

Arg Gly Pro Leu Ser Trp Thr His Val His Pro Lys Gly Pro Lys Ser
210             215                     220

Leu Leu Ser Leu Glu Leu Lys Asp Asp Arg Pro Ala Arg Asp Met Trp
225                 230                 235                 240

Val Met Glu Thr Gly Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
            290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
                340                 345                 350

Ser Leu Pro Thr Pro Thr Ser Gly Leu Gly Arg Ala Gln Arg Trp Ala
            355                 360                 365

Ala Gly Leu Gly Gly Thr Ala Pro Ser Tyr Gly Asn Pro Ser Ser Asp
            370                 375                 380

Val Gln Ala Asp Gly Ala Leu Gly Ser Arg Ser Pro Pro Gly Val Gly
385                 390                 395                 400

Pro Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
                420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
            450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
            515                 520                 525

Asp Ser Tyr Glu Asn Met Asp Asn Pro Asp Gly Pro Asp Pro Ala Trp
            530                 535                 540

Gly Gly Gly Gly Arg Met Gly Thr Trp Ser Thr Arg
545                 550                 555

<210> SEQ ID NO 139
<211> LENGTH: 297
<212> TYPE: PRT
<213> ORGANISM: unknown
<220> FEATURE:
<223> OTHER INFORMATION: CD20 cancer vaccine antigen
```

-continued

```
<400> SEQUENCE: 139

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 140
<211> LENGTH: 937
<212> TYPE: PRT
<213> ORGANISM: unknown
<220> FEATURE:
<223> OTHER INFORMATION: ROR1 cancer vaccine antigen

<400> SEQUENCE: 140

Met His Arg Pro Arg Arg Arg Gly Thr Arg Pro Pro Leu Leu Ala Leu
1               5                   10                  15

Leu Ala Ala Leu Leu Leu Ala Ala Arg Gly Ala Ala Ala Gln Glu Thr
            20                  25                  30

Glu Leu Ser Val Ser Ala Glu Leu Val Pro Thr Ser Ser Trp Asn Ile
        35                  40                  45

Ser Ser Glu Leu Asn Lys Asp Ser Tyr Leu Thr Leu Asp Glu Pro Met
```

-continued

```
              50                  55                  60
Asn Asn Ile Thr Thr Ser Leu Gly Gln Thr Ala Glu Leu His Cys Lys
 65                  70                  75                  80

Val Ser Gly Asn Pro Pro Thr Ile Arg Trp Phe Lys Asn Asp Ala
                 85                  90                  95

Pro Val Val Gln Glu Pro Arg Arg Leu Ser Phe Arg Ser Thr Ile Tyr
                100                 105                 110

Gly Ser Arg Leu Arg Ile Arg Asn Leu Asp Thr Thr Asp Thr Gly Tyr
                115                 120                 125

Phe Gln Cys Val Ala Thr Asn Gly Lys Glu Val Val Ser Ser Thr Gly
                130                 135                 140

Val Leu Phe Val Lys Phe Gly Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
                180                 185                 190

His Met Gln Gly Glu Ile Glu Asn Gln Ile Thr Ala Ala Phe Thr Met
                195                 200                 205

Ile Gly Thr Ser Ser His Leu Ser Asp Lys Cys Ser Gln Phe Ala Ile
                210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
                260                 265                 270

Ile Leu Met Arg Leu Lys Leu Pro Asn Cys Glu Asp Leu Pro Gln Pro
                275                 280                 285

Glu Ser Pro Glu Ala Ala Asn Cys Ile Arg Ile Gly Ile Pro Met Ala
                290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
                340                 345                 350

Pro Glu Leu Asn Gly Gly His Ser Tyr Cys Arg Asn Pro Gly Asn Gln
                355                 360                 365

Lys Glu Ala Pro Trp Cys Phe Thr Leu Asp Glu Asn Phe Lys Ser Asp
                370                 375                 380

Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
                405                 410                 415

Ala Ile Ala Leu Leu Phe Phe Phe Ile Cys Val Cys Arg Asn Asn Gln
                420                 425                 430

Lys Ser Ser Ser Ala Pro Val Gln Arg Gln Pro Lys His Val Arg Gly
                435                 440                 445

Gln Asn Val Glu Met Ser Met Leu Asn Ala Tyr Lys Pro Lys Ser Lys
                450                 455                 460

Ala Lys Glu Leu Pro Leu Ser Ala Val Arg Phe Met Glu Glu Leu Gly
465                 470                 475                 480
```

```
Glu Cys Ala Phe Gly Lys Ile Tyr Lys Gly His Leu Tyr Leu Pro Gly
            485                 490                 495

Met Asp His Ala Gln Leu Val Ala Ile Lys Thr Leu Lys Asp Tyr Asn
        500                 505                 510

Asn Pro Gln Gln Trp Thr Glu Phe Gln Gln Glu Ala Ser Leu Met Ala
            515                 520                 525

Glu Leu His His Pro Asn Ile Val Cys Leu Leu Gly Ala Val Thr Gln
        530                 535                 540

Glu Gln Pro Val Cys Met Leu Phe Glu Tyr Ile Asn Gln Gly Asp Leu
545                 550                 555                 560

His Glu Phe Leu Ile Met Arg Ser Pro His Ser Asp Val Gly Cys Ser
            565                 570                 575

Ser Asp Glu Asp Gly Thr Val Lys Ser Ser Leu Asp His Gly Asp Phe
        580                 585                 590

Leu His Ile Ala Ile Gln Ile Ala Ala Gly Met Glu Tyr Leu Ser Ser
            595                 600                 605

His Phe Phe Val His Lys Asp Leu Ala Ala Arg Asn Ile Leu Ile Gly
        610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Leu Leu Pro Ile
            645                 650                 655

Arg Trp Met Pro Pro Glu Ala Ile Met Tyr Gly Lys Phe Ser Ser Asp
        660                 665                 670

Ser Asp Ile Trp Ser Phe Gly Val Val Leu Trp Glu Ile Phe Ser Phe
            675                 680                 685

Gly Leu Gln Pro Tyr Tyr Gly Phe Ser Asn Gln Glu Val Ile Glu Met
        690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
            725                 730                 735

Pro Arg Phe Lys Asp Ile His Val Arg Leu Arg Ser Trp Glu Gly Leu
        740                 745                 750

Ser Ser His Thr Ser Ser Thr Thr Pro Ser Gly Gly Asn Ala Thr Thr
            755                 760                 765

Gln Thr Thr Ser Leu Ser Ala Ser Pro Val Ser Asn Leu Ser Asn Pro
        770                 775                 780

Arg Tyr Pro Asn Tyr Met Phe Pro Ser Gln Gly Ile Thr Pro Gln Gly
785                 790                 795                 800

Gln Ile Ala Gly Phe Ile Gly Pro Pro Ile Pro Gln Asn Gln Arg Phe
            805                 810                 815

Ile Pro Ile Asn Gly Tyr Pro Ile Pro Pro Gly Tyr Ala Ala Phe Pro
        820                 825                 830

Ala Ala His Tyr Gln Pro Thr Gly Pro Pro Arg Val Ile Gln His Cys
            835                 840                 845

Pro Pro Pro Lys Ser Arg Ser Pro Ser Ser Ala Ser Gly Ser Thr Ser
        850                 855                 860

Thr Gly His Val Thr Ser Leu Pro Ser Ser Gly Ser Asn Gln Glu Ala
865                 870                 875                 880

Asn Ile Pro Leu Leu Pro His Met Ser Ile Pro Asn His Pro Gly Gly
            885                 890                 895
```

```
Met Gly Ile Thr Val Phe Gly Asn Lys Ser Gln Lys Pro Tyr Lys Ile
            900                 905                 910

Asp Ser Lys Gln Ala Ser Leu Leu Gly Asp Ala Asn Ile His Gly His
        915                 920                 925

Thr Glu Ser Met Ile Ser Ala Glu Leu
        930                 935

<210> SEQ ID NO 141
<211> LENGTH: 168
<212> TYPE: PRT
<213> ORGANISM: unknown
<220> FEATURE:
<223> OTHER INFORMATION: WT1 cancer vaccine antigen

<400> SEQUENCE: 141

Met Gly His His His His His His His His Ser Ser Gly His
1               5                   10                  15

Ile Glu Gly Arg His Met Arg Arg Val Pro Gly Val Ala Pro Thr Leu
            20                  25                  30

Val Arg Ser Ala Ser Glu Thr Ser Glu Lys Arg Pro Phe Met Cys Ala
        35                  40                  45

Tyr Pro Gly Cys Asn Lys Arg Tyr Phe Lys Leu Ser His Leu Gln Met
    50                  55                  60

His Ser Arg Lys His Thr Gly Glu Lys Pro Tyr Gln Cys Asp Phe Lys
65                  70                  75                  80

Asp Cys Glu Arg Arg Phe Phe Arg Ser Asp Gln Leu Lys Arg His Gln
                85                  90                  95

Arg Arg His Thr Gly Val Lys Pro Phe Gln Cys Lys Thr Cys Gln Arg
            100                 105                 110

Lys Phe Ser Arg Ser Asp His Leu Lys Thr His Thr Arg Thr His Thr
        115                 120                 125

Gly Glu Lys Pro Phe Ser Cys Arg Trp Pro Ser Cys Gln Lys Lys Phe
    130                 135                 140

Ala Arg Ser Asp Glu Leu Val Arg His His Asn Met His Gln Arg Asn
145                 150                 155                 160

Met Thr Lys Leu Gln Leu Ala Leu
                165

<210> SEQ ID NO 142
<211> LENGTH: 1785
<212> TYPE: DNA
<213> ORGANISM: artificial
<220> FEATURE:
<223> OTHER INFORMATION: murine codon-optimized piggyBac iPB7
      transposase cDNA

<400> SEQUENCE: 142
atgggcagca gcctggacga cgagcacatc ctgagcgccc tgctgcagag cgacgacgag      60
ctggtcggcg aggacagcga cagcgagatc agcgaccacg tgagcgagga cgacgtgcag     120
tccgacaccg aggaggcctt catcgacgag gtgcacgagg tgcagcctac cagcagcggc     180
tccgagatcc tggacgagca gaacgtgatc gagcagcccg gcagctccct ggccagcaac     240
aggatcctga ccctgcccca ggaggaccat cagggcaaga acaagcactg ctggtccacc     300
tccaagagca ccaggcggag cagggtgtcc gccctgaaca tcgtgagaag ccagggggc     360 cccaccagga tgtgcaggaa catctacgac cccctgctgt gcttcaagct gttcttcacc     420
gacgagatca tcagcgagat cgtgaagtgg accaacgccg agatcagcct gaagaggcgg     480
```

```
gagagcatga ccggcgccac cttcagggac accaacgagg acgagatcta cgccttcttc        540
ggcatcctgg tgatgaccgc cgtgaggaag gacaaccaca tgagcaccga cgacctgttc        600
gacagatccc tgagcatggt gtacgtgagc gtgatgagca gggacagatt cgacttcctg        660
atcagatgcc tgaggatgga cgacaagagc atcaggccca ccctgcggga gaacgacgtg        720 ttcaccccg tgagaaagat ctgggacctg ttcatccacc agtgcatcca gaactacacc         780
cctggcgccc acctgaccat cgacgagcag ctgctgggct tcaggggcag gtgcccttc         840 aggatgtata tccccaacaa gcccagcaag tacggcatca agatcctgat gatgtgcgac        900
agcggcacca agtacatgat caacggcatg ccctacctgg gcaggggcac ccagaccaac        960
ggcgtgcccc tgggcgagta ctacgtgaag gagctgtcca gcccgtcca cggcagctgc        1020 agaaacatca cctgcgacaa ctggttcacc agcatccccc tggccaagaa cctgctgcag       1080
gagccctaca agctgaccat cgtgggcacc gtgagaagca caagagaga gatccccgag       1140 gtcctgaaga acagcaggtc caggcccgtg ggcaccagca tgttctgctt cgacggcccc       1200
ctgaccctgg tgtcctacaa gcccaagccc gccaagatgg tgtacctgct gtccagctgc       1260
gacgaggacg ccagcatcaa cgagagcacc ggcaagcccc agatggtgat gtactacaac       1320
cagaccaagg gcggcgtgga caccctggac cagatgtgca gcgtgatgac ctgcagcaga       1380
aagaccaaca ggtggcccat ggccctgctg tacggcatga tcaacatcgc ctgcatcaac       1440
agcttcatca tctacagcca caacgtgagc agcaagggcg agaaggtgca gagccggaaa      1500
aagttcatgc ggaacctgta catgagcctg acctccagct tcatgaggaa gaggctggag      1560 gccccccaccc tgaagagata cctgagggac aacatcagca acatcctgcc caacgaggtg      1620
cccggcacca gcgacgacag caccgaggag cccgtgatga agaagaggac ctactgcacc      1680
tactgtccca gcaagatcag aagaaaggcc aacgccagct gcaagaagtg taagaaggtc      1740
atctgccggg agcacaacat cgacatgtgc cagagctgtt tctga                       1785
```